(12) United States Patent
Van Dyke

(10) Patent No.: US 9,068,162 B2
(45) Date of Patent: Jun. 30, 2015

(54) KERATIN BIOMATERIALS FOR CELL CULTURE AND METHODS OF USE

(75) Inventor: Mark E. Van Dyke, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1112 days.

(21) Appl. No.: 12/704,839

(22) Filed: Feb. 12, 2010

(65) Prior Publication Data

US 2010/0197021 A1    Aug. 5, 2010

Related U.S. Application Data

(63) Continuation-in-part of application No. 12/192,490, filed on Aug. 15, 2008.

(60) Provisional application No. 60/956,454, filed on Aug. 17, 2007, provisional application No. 61/152,562, filed on Feb. 13, 2009.

(51) Int. Cl.
  *C12N 5/00* (2006.01)
  *A61L 27/22* (2006.01)
  *A61L 27/34* (2006.01)
  *A61L 27/52* (2006.01)

(52) U.S. Cl.
  CPC ............ *C12N 5/0068* (2013.01); *A61L 27/227* (2013.01); *A61L 27/34* (2013.01); *A61L 27/52* (2013.01); *C12N 5/0075* (2013.01); *C12N 2533/50* (2013.01)

(58) Field of Classification Search
  None
  See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,236,921 A | 4/1941 | Schollkopf et al. | |
| 2,413,983 A | 1/1947 | Lustig et al. | |
| 2,434,688 A | 1/1948 | Evans | |
| 2,445,028 A | 7/1948 | Jones et al. | |
| 2,517,572 A | 8/1950 | Jones et al. | |
| 2,814,851 A | 12/1957 | Hervey | |
| 3,033,755 A | 5/1962 | Jacobi | |
| 3,464,825 A | 9/1969 | Anker | |
| 3,642,498 A | 2/1972 | Anker | |
| 3,655,416 A | 4/1972 | Vinson et al. | |
| 4,178,361 A | 12/1979 | Cohen et al. | |
| 4,357,274 A | 11/1982 | Werner et al. | |
| 4,423,032 A | 12/1983 | Abe et al. | |
| 4,495,173 A | 1/1985 | Matsunaga et al. | |
| 4,570,629 A | 2/1986 | Widra | |
| 4,751,074 A | 6/1988 | Matsunaga et al. | |
| 4,895,722 A | 1/1990 | Abe et al. | |
| 4,959,213 A | 9/1990 | Brod et al. | |
| 5,047,249 A | 9/1991 | Rothman et al. | |
| 5,300,285 A | 4/1994 | Halloran et al. | |
| 5,320,796 A | 6/1994 | Harashima et al. | |
| 5,358,935 A | 10/1994 | Smith et al. | |
| 5,634,945 A | 6/1997 | Pernia et al. | |
| 5,679,819 A | 10/1997 | Jones et al. | |
| 5,691,203 A | 11/1997 | Katsuen et al. | |
| 5,695,998 A | 12/1997 | Badylak et al. | |
| 5,763,583 A | 6/1998 | Arai et al. | |
| 5,932,552 A | 8/1999 | Blanchard et al. | |
| 5,948,432 A | 9/1999 | Timmons et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,165,496 A | 12/2000 | Timmons et al. | |
| 6,268,454 B1 | 7/2001 | Song et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,274,163 B1 | 8/2001 | Blanchard et al. | |
| 6,316,598 B1 | 11/2001 | Van Dyke et al. | |
| 6,371,984 B1 | 4/2002 | Van Dyke et al. | |
| 6,379,690 B2 | 4/2002 | Blanchard et al. | |
| 6,432,435 B1 | 8/2002 | Timmons et al. | |
| 6,461,628 B1 | 10/2002 | Blanchard et al. | |
| 6,544,548 B1 | 4/2003 | Siller-Jackson et al. | |
| 6,746,836 B1 | 6/2004 | Widra | |
| 6,783,546 B2 * | 8/2004 | Zucherman et al. | ....... 623/17.16 |
| 7,439,012 B2 * | 10/2008 | Van Dyke | ...................... 435/1.1 |
| 2001/0021389 A1 | 9/2001 | Starling et al. | |
| 2003/0049266 A1 | 3/2003 | Fearon et al. | |
| 2005/0058686 A1 * | 3/2005 | Van Dyke et al. | ............ 424/426 |
| 2006/0051732 A1 | 3/2006 | Van Dyke | |
| 2007/0166348 A1 | 7/2007 | Van Dyke | |
| 2007/0249044 A1 | 10/2007 | Desai et al. | |
| 2007/0298070 A1 | 12/2007 | Van Dyke | |
| 2008/0003676 A1 | 1/2008 | Sheridan et al. | |
| 2008/0274165 A1 | 11/2008 | Van Dyke | |
| 2009/0004242 A1 | 1/2009 | Van Dyke | |
| 2009/0047260 A1 | 2/2009 | Van Dyke | |

FOREIGN PATENT DOCUMENTS

| | | |
|---|---|---|
| DE | 184915 | 12/1905 |
| DE | 22643 | 10/1907 |

(Continued)

OTHER PUBLICATIONS

U.S. Appl. No. 11/676,072, filed Feb. 16, 2007, Van Dyke.

(Continued)

*Primary Examiner* — Allison Fox
(74) *Attorney, Agent, or Firm* — Meyers Bigel Sibley & Sajovec, P.A.

(57) ABSTRACT

Provided are keratin compositions useful in cell culture. In some embodiments the keratins are biocompatible, promote cell growth, promote cell adhesion and provide an excellent substrate for cell culture. Keratin compositions described herein may be used as coatings, gels, three-dimensional scaffolds, additives to cell culture media, microcarriers, etc. The keratin substrates may also be used to deliver cells, e.g., for cell therapy applications.

20 Claims, 12 Drawing Sheets

(56) References Cited

FOREIGN PATENT DOCUMENTS

| | | |
|---|---|---|
| EP | 0 454 600 A1 | 4/1991 |
| EP | 0468797 A2 | 1/1992 |
| EP | 0 540 357 A2 | 5/1993 |
| GB | 531446 A | 1/1941 |
| GB | 2 241 253 A | 8/1991 |
| JP | 52-148581 A | 12/1977 |
| JP | 53-016091 A | 2/1978 |
| JP | 54-137064 A | 10/1979 |
| JP | 55-051095 A | 4/1980 |
| JP | 56-030909 A | 3/1981 |
| JP | Sho 55-98256 | 2/1982 |
| JP | S57-109797 | 7/1982 |
| JP | 1-174528 | 7/1989 |
| JP | 2-051533 A | 2/1990 |
| JP | 3-011099 A | 1/1991 |
| JP | 4-082561 A | 3/1992 |
| JP | 4-091138 A | 3/1992 |
| JP | Hei 4-189833 | 7/1992 |
| JP | 5-285374 A | 11/1993 |
| JP | 5-285375 A | 11/1993 |
| JP | 5-320358 A | 12/1993 |
| JP | 6-100600 A | 4/1994 |
| JP | 6-116300 A | 4/1994 |
| JP | 6-336499 A | 12/1994 |
| JP | 9-227565 A | 9/1997 |
| JP | 10-291998 A | 11/1998 |
| JP | 10-291999 A | 11/1998 |
| JP | 10-337466 | 12/1998 |
| JP | 2000-191792 A | 7/2000 |
| JP | 2001-087754 A | 4/2001 |
| JP | 2001-114647 A | 4/2001 |
| NL | 51000577 | 12/1941 |
| RU | 2 106 154 C1 | 3/1998 |
| RU | 2 108 079 C1 | 4/1998 |
| WO | WO 91-02538 A1 | 3/1991 |
| WO | WO 93/10827 A1 | 6/1993 |
| WO | WO 93/12819 A1 | 7/1993 |
| WO | WO 98/08550 A1 | 3/1998 |
| WO | WO 99/26570 A1 | 6/1999 |
| WO | WO 99/26595 A1 | 6/1999 |
| WO | WO 99/51175 A1 | 10/1999 |
| WO | WO 00/76437 A1 | 12/2000 |
| WO | WO 01/19283 A2 | 3/2001 |
| WO | WO 01/19305 A1 | 3/2001 |
| WO | WO 01/64033 A2 | 9/2001 |
| WO | WO 02/45508 A1 | 6/2002 |
| WO | WO 03/011894 A1 | 2/2003 |
| WO | WO 03/064449 A2 | 8/2003 |
| WO | WO 03/086491 A2 | 10/2003 |
| WO | WO 2007/098114 | 8/2007 |

OTHER PUBLICATIONS

Goddard DR and Michaelis L. A study on keratin. *J Biol Chem* 1934;106:605-14.
O'Donnell IJ and Thompson EOP. Studies on oxidized wool IV. Fractionation of proteins extracted from wool on DEAE-cellulose using buffers containing 8M urea. *Aust. J. Biol. Sci.* 1961;14:461-474.
Thompson et al., Studies on Reduced Wool. *Aust. J. Biol. Sci.* 15:757-68 (1962).
Crewther WG et al., *The Chemistry of Keratins*. Anfinsen CB Jr et al., editors. Advances in Protein Chemistry 1965. Academic Press. New York:191-346.
Thomas H et al. In vitro reconstitution of wool intermediate filaments. *Int. J. Biol. Macromol.* Oct. 1986; 8: 258-264.
Yamauchi, The development of keratin: Characteristics of Polymer Films. *Fragrance J.* 1993; 21(5): 62-67. (English Translation of Entire Document).
Mitsui S, Ohuchi A, Hotta M, Tsuboi R, Ogawa H. Genes for a range or growth factors and cyclin-dependent kinase inhibitors are expressed by isolated human hair follicles. *British J Dermatol.* 1997;137: 693-698.

Lee SJ, Van Dyke ME. Tissue engineering scaffolds from self-assembled human hair keratins. *Polym Prep* 2005; 46(1): 112.
Tachibana A et al. Rapid fabrication of keratin-hydroxyapatite hybrid sponges toward osteoblast cultivation and differentiation. *Biomaterials.* 2005; 26: 297-302.
BD Matrigeln™ Basement Membrane Matrix product description. BD Biosciences. www.bdbiosciences.com. Printed Feb. 4, 2009, 4 pp.
Goddard DR and Michaelis L. Derivatives of Keratin. JBC. 1935: 361-371.
Reichl S. Keratin coated surfaces as growth substrate—a novel approach to stimulate cell proliferation in culture. 5th World Meeting on Pharmaceutics, Biopharmaceutics, and Pharmaceutical Technology, Geneva. Mar. 30, 2006: 1 page.
Sizin, T.L.; "The occurance of azelaic acid among the oxidation products of keratin." Z. Physiology Chemistry: vol. 62, 1910, pp. 226-228.
Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.
Smith, A.L.; et al; "Oxidation of Wool—The Effect of Hydrogen Peroxide." Rayon Textile Monthly; vol. 39, 1936. pp. 39, 40.
Smith, A.L.; et al; "Oxidation of Wool: The lead acetate test for hydrogen peroxide bleached wool."Journal of Research of the National Bureau of Standards, vol. 16, 1936, pp. 309-312.
Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.
Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.
Stary, Z.; "Brominated keratin and oxykeratin."; Z. Physiology Chemistry; vol. 144, 1925, pp. 147-177.
Stary, Z.; "Solubility and digestibility of the degradation products of albumoids." Z. Physiology Chemistry; vol. 136, 1924, pp. 160-172.
Steinert, P.M.; et al; "In vitro studies on the synthesis of guinea pig hair keratin proteins." Biochimica et Biophysica Acta; vol. 312, 1973, pp. 403-412.
Stenn, K.S.; "The molecular and structural biology of hair, Introduction."; Annals of New York Academy of Sciences; vol. 83, 1959, pp. 359-512.
Stenn, K.S.; et al.; "Controls of hair Follicle cycling.."; Physiological Reviews; vol. 81, No. 1, 2001, pp. 449-494.
Stenn, K.S.; et al.; "Hair follicle growth controls." Dermatologic Clinics; vol. 14, No. 4, 1996, pp. 543-558.
Stenn, K.S.; et al.; "Molecules of the cycling hair follicle—a tabulated review." Journal of Dermatalogical Science 7(Suppl.) 1994, pp. 109-124.
Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.
Stokes,G.D.; Dunson, W.A.; "Passage of water and electrolytes through natural and artificial keratin membranes." Desalination; vol. 42, 1982, pp. 321-328.
Struessmann, A.; et al.; "Specific radiolabeling of keratin proteins by amidination."; Journal of Chromatography, vol. 268, 1983, pp. 306-310.
Suzuki, E.; et al; "X-ray diffraction and infrared studies of an α-helical fragment from α-keratin." Journal of Molecular Biology; vol. 73, 1973, pp. 275-278.
Tachibana, A. et al.; "Fabrication of wool keratin sponge scaffolds for long-term cell cultivation." Journal of Biotechnology, vol. 93, 2002 pp. 165-170.
Tanabe, T.; Tachibana, A.; Yamauchi, K.; "Keratins: prospective proteinous biomaterial."; Recent Research Developments in Protein Engineering; vol. 1(Pt.2),2001, pp. 247-259.
Tazawa, T.; et al; "Anti-hair keratin monoclonal antibody (HKN-2)."; The Journal of Dermatology; vol. 12, 1985, pp. 313-317.

(56) References Cited

OTHER PUBLICATIONS

Thomas, H.; et al; "Isolation of the microfibrillar proteins of wool in the disulfide form." Melliand Textilberichte; vol. 65, No. 3, 1984, pp. 208-209.

Tsai, A.G.; et al; "High viscocity plasma expanders: Volume restitution fluids for lowering the transfusion trigger."; Biorheology, vol. 38 (2-3), 2001, pp. 229-237.

Tsai, A.G.; et al; "The unusual properties of effective blood substitutes."; Keio Journal of Medicine; vol. 51 (1), 2002, pp. 17-20.

Tsuchida, E.; "Oxygen ligation of macromolecule-porphyrin complexes."; Journal of the Chemical Society of Japan; No. 6, 1988, pp. 845-852.

Tsuchida, E.; et al; "Cobalt (II)/poly(ethyleneimine) membrane with oxygen binding ability."; Makromolekulare Chemie; vol. 3 (10), 1982, pp. 693-696.

Tucker, D.J.; et al; "Variations in goat fiber proteins."; Australian Journal of Agriculture Research vol. 40, No. 3, 1989, pp. 675-683.

Ueyama, N.; et al; "A novel method for determining the chelation ability of the cysteine-containing peptides with 3,4-toluenedithiol. Application to .cents .2Fe-2S-ferredoxin model systems."; Bulletin of the Chemical Society of Japan; vol. 60 (1), 1987, pp. 283-287.

Van Neste, D.; "The growth of human hair in nude mice."; Dermatologic Clinics; vol. 14, No. 4, 1996, pp. 609-617.

Vasak, M.; et al; "Metal thiolate clusters in cobalt (II)-metallothionein."; Proceedings of the National Academy of Sciences of the United States of America; vol. 78 (11), 1981, pp. 6709-6713.

Vogeli, G.; et al; "High-Sulfur Protein Gene Expression in a Transgenic Mouse." Annals New York Academy of Sciences; vol. 642, 1991, pp. 21-30.

Ward, K.A.; et al.; "The structure of the wool keratin microfibrillar genes." Proceedings of the Australian Biochemical Society; vol. 15, 1983, pp. 70.

Ward, K.A.; "Changes in wool follicle keratinocyte protein-biosynthesis mediated by inhibitors of follicle bulb cell-proliferation."; Proceedings of the Australian Biochemical Society; vol. 9, 1976, vol. 9, pp. 57.

Ward, K.A.; "Study of keratin biosynthesis in isolated wool follicle cells." Proceedings of the Australian Biochemical Society; vol. 7, 1974, pp. 93.

Weber, K.; Geisler, N.; "The structural relation between intermediate filament proteins in living cells and the alpha-keratins of sheep wool" The EMBO Jjournal; vol. 1 No. 10, 1982, pp. 1155-1160.

Weiss, R.A.; Guilett, Y.A,G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.

Werner, S.; et al.; "Large induction of keratinocyte growth factor expression in the dermis during wound healing." Proceedings of the National Academy of Sciences, USA; vol. 89, 1992, pp. 6896-6900.

Whitbread, L.A.; et al; "Expression of the intermediate filament gene, K15, in the basal cell layers of epithelia and the hair follicle."; Experimental Cell Research; vol. 244, 1998, pp. 448-459.

Widra, A.; "Ascoporogenesis by nannizzia grubyia on a soluble fraction of keratin." Mycopathologia et Mycologia Applicata; vol. 30, No. 2, 1966 pp. 141-144.

Wilson, B. W.; et al.; "Complete sequence of a type-I microfibrillar wool keratin gene."; Gene; vol. 73, No. 1, 1988, pp. 21-31.

Wilson, N.; et al; "The role of BMP-2 and BMP-4 in follicle initiation and the murine hair cycle."; Experimental Dermatology; vol. 8, No. 4, 1999, pp. 367-368.

Wolski, T.; Szumilo, H.; "Studies on the kinetics of dissolving feather keratin in the water-urea system." Acta Alimentaria Polinica; vol. 8, (32) No. 1-2, 1982, pp. 102-108.

Wormell, R. L.; "Regenerated fibers from wool." Brit. Rayon Silk Journal; vol. 26, No. 309, pp. 55, 1950.

Wormell, R.L.; "Regenerated protein fibres from wool and casein"; The Journal of the Textile Institute; vol. 39, 1948, T219-T224.

Wormell, R.L.; "Wool, silk and regenerated protein fibers-hemistry." Rev. Textile Progress; vol. 9, 1957, pp. 51-62.

Wortmann, F.J.; et al.; "A method for isolating the cortex of keratin fibers."; Textile Research Journal; vol. 52, 1982, pp. 479-481.

Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.

Yamamura, T.; et al; "Conformation control of peptides by metal ions. Coordination confirmation correlation observed in a model for Cys-X-Y-Cys/M2+ in proteins."; Inorganic Chemistry; vol. 36 (21), 1997, pp. 4849-4859.

Yamauchi, K. et al.; "Novel proteinous microcapsules from wool keratins." Colloids and Sudaces, B: Biointertaces; vol. 9, 1997, pp. 117-119.

Yamauchi, K.; "Dissolution of hair and wool. Keratin polymers." Kobunshi Kako; vol. 4i, No. 1, 1994, pp. 14-19.

Yamauchi, K.; "Perspective in chemistry and applications of keratins." Kobunshi; vol. 50, No. 4, 2001, pp. 240-243.

Yamauchi, K.; "Polymer films fom keratin."; Fragrance Journal; vol. 21 (5), 1993, pp. 62-67.

Yamauchi, K.; "Preparation of stable aqueous solution of keratins, and physicochemical and biochemical properties of films." Polymer Preprints-American Chemical Society, Division of Polymer Chemistry; vol. 39, No. 1, 1998, pp. 357-358.

Yamauchi, K.; et al.; "Cultivation of Mouse L929 Fibroblast Cells on Keratins."; Kobunshi Gakkai Yokoshu (Polymer Preprints), Japan; vol. 44, No. 3,1995, pp. 503.

Yamauchi, K.; et al.; "Preparation of stable aqueous solution of keratins, and physicochemical and biodegradational properties of films." Journal of Biomedical Materials Research; vol. 31, No. 4, 1996, pp. 439-444.

Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472.

Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.

Yoshimizu, H.; et al; "C CP/MAS NMR study of the conformation of stretched or heated low-sulfur keratin protein films." Macromolecules,; vol. 24, 1991, pp. 862-866.

Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230.

Zahn, H. et al.; "Reactivity of amino acid side chains. 18. Reactions of p-fluoro-m,m'-dinitrodiphenyl sulfone and p,p'-difluro-m,m'-dinotrodiphenyl sulfone with wool keratin and silk fibroin."; Kolloid Zeitschrift fuer Polymere; vol. 5, 1973 pp. 289-298.

Zahn, H. et al.; "Wool as a biological composite structure."; Industrial & Engineering Chemistry Product Research and Development; vol. 19, 1980, pp. 496-501.

Zahn, H.; "Progress report on hair keratin research."; International Journal of Cosmetic Science; vol. 24, 2002, pp. 163-169.

Zahn, H.; "Structure and chemistry of wool fibers." Kolloid-Z; vol. 100, 1942, pp. 283-298.

Zahn, H.; "The role of mohair keratin research." Melliand Textilberichte; vol. 72, 1991, pp. 926-931.

Zahn, H.; "Wool research taking part in comtemporary chemistry and physics."Arbeitsgemeinschaft Forsch. Landes Nordheim-Westfalen; vol. 75, 1957, pp. 47-80.

Zahn, H.G.; et al; "2-Dimensional keratin patterns of human hair including cosmetically treated ones."; Journal of Forensic Science Society; vol. 24, No. 4, 1984, pp. 432.

Zahn,H. et al.; "Wool as a biological compounding material." Schriftenreihe des Deautschen Wollforschungsintitutes; vol. 76, 1978, pp. 18-25.

Crewther, W.G. et al; "Helix-rich fraction from the low-sulphur proteins of wool."; Nature; vol. 207,(4994), 1965, pp. 295.

Crewther, W.G.; Effect of aftertreatment on the stability of set wool fibers. Comments; Journal of the Society of Dyers and Colourist; vol. 86, No. 5, 1970, pp. 208.

(56) References Cited

OTHER PUBLICATIONS

Crewther, W.G.; "The concept of internal pH in wool fibers and the interpretation of data relating to setting."; Journal of the Society of Dyers and Colourist; vol. 81, (4), 1965, pp. 156-158.

Crewther, W.G.; "The viscoelasticity of alpha keratin fibers."; Experimental Dermatology; vol. 8 (4), 1999, pp. 343-344.

Crewther, W.G.; "Preparation and properties of large peptides from the helical regiones of the low-sulfur proteins of wool."; Applied Polymer Symposia; vol. 18, No. 1, 1971, pp. 1-20.

Crewther, W.G.; "Structure of .alpha-keratin."; Textile Research Journal; vol. 42, No. 4, 1972, pp. 251-252.

Crewther, W.G.; "The stress-strain characteristics of animal fibers after reduction and alkylation."; Textile Research Journal; vol. 35, No. 10, 1965, pp. 867-877.

Crewther, W.G.; "Thiol-disulfide interchange reactions in the setting of single wool fibers." Journal of the Society of Dyers and Colourist; vol. 82, No. 1, 1966, pp. 54-58.

Crewther, W.G.; et al; "Effect of S-carboxymethylation of wool proteins on the iodination of tyrosine residues."; Textile Research Journal; vol. 41, No. 3, 1971, 99.267.

Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.

Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.

Crewther, W.G.; et al; "Amino acid sequences of α-helical segments from S-carboxymethlykerateine-A. Tryptic and chymotryptic peptides from a type-II segment."; Biochemistry Journal; vol. 173, 1978 pp. 353-363.

Crewther, W.G.; et al; "Formation of various crosslinkages in wool and their effect on the supercontraction properties of the fibers."; Textile Research Journal; vol. 37, No. 9, 1967, pp. 736-745.

Crewther, W.G.; et al; "Low-sulfur proteins from α-keratins. Interrelationship between their amino acid compositions, α-helix contents, and the supercontraction of the parent keratin." Biopolymers, vol. 4, 1966, pp. 905-916.

Crewther, W.G.; et al; "Reduction of S-carboxymethlycysteine and methionine with sodium in liquid ammonia." Biochimica et Biophysica Acta; vol. 164, 1969, pp. 606-609.

Crewther, W.G.; et al; "Structure of intermediate filaments."; International Journal of Biological Macrmolecules; vol. 5, No. 5, 1983, pp. 267-274.

Crewther, W.G.; et al; "The chemistry of keratins."; Advance Protein Chemistry; vol. 20, 1965 pp. 191-346.

Crewther, W.G.; et al; "The preparation and properties of a helix-rich fraction obtained by partial proteolysis of low sulfur S-Carboxymethylkerateine from wool." The Journal of Biological Chemistry; vol. 242, No. 19, 1967, pp. 4310-4319.

Dale, H.N.; "Keratin and other coatings for pills."; Pharmacology Journal; vol. 129, 1932, pp. 494-495.

Damaglou, A.P.; et al; "The hydrolysis by thermolysin of dipeptide derivatives that contain substituted cysteine" Biochemical Journal; vol. 123, No. 3, 1971, pp. 379-384.

Darskus, R.L.; et al.; "Breed and species differences in the hair proteins of four genera of caprini." Australian Journal of Biological Sciences; vol. 24, 1971, pp. 515-524.

Darskus, R.L.; et al; "The possibility of common amino acid sequences in high sulphur protein fractions from wool." Australian Journal of Biological Sciences; vol. 22, 1969, pp. 1197-1204.

De Sanctis, G.; et al; "Mini-myoglobin—Electron paramagnetic resonance and reversible oxygenation of the cobalt derivative."; Journal of Molecular Biology; vol. 222, 1991, pp. 637-643.

Dedeurwaerder, R.A.; et al; "Selective extraction of protein fraction from wool keratin." Nature vol. 203, 1964, pp. 48, 49.

Dobb, M.G.; et al; "Electron microscopy of fibrous keratins."; Symposuim of fibrous protein, Int Conf.; 1967, pp. 267-278.

Dowling, L.M.; Crewther, W.G.; Inglis, A.S.; "The primary structure of component 8c-1, a subunit protein of intermediate filaments in wool keratin."; Biochemistry Journal vol. 236, 1986, pp. 695-703.

Dowling, L.M.; Crewther, W.G.; Parry, D.A.D.; "The secondary structure of component 8c-1, of alpha-keratin."; Biochemistry Journal; vol. 236, 1986, pp. 705-712.

Dowling, L.M.; et al; "Effect of the solvent on the iodanation of a tyrosine derivative and its relation to iodination of wool."; Textile Research Journal; vol. 41, No. 1, 1971, pp. 65-69.

Dowling, L.M.; et al; "Isolation of components from the low sulphur proteins of wool by fractional precipitation."; Preparative Biochemistry, vol. 4(3), 1974, pp. 203-226.

Downes, A.M.; et al; "Evaluation of modified [35S] methionine and [35S] casein preparations as supplements for sheep"; British Journal of Nutrition; vol. 24, No. 4, 1970, pp. 1083-1089.

Downes, A.M.; et al; "Matabolic fate of parenterally administered sulphur containing amino acids in sheep and the effects on growth and composition of wool" ; Australian Journal of Biological Sciences; vol. 23, No. 5, 1970, pp. 1077-1088.

Downes, A.M.; Ferguson,K.A.; Gillespie, J.M.; Harrap, B.S.; "A study of the proteins of the wool follicle." Australian Journal of Biological Science; vol. 19. 1966, pp. 319-333.

Dunn, S.M.; et al; "Regulation of hair gene expression."; Experimental Dermatology, vol. 8, 1999, pp. 341-342.

Earland, C.; et al; "Structure of keratin. II. Amino acid content of fractions isolated from oxidized wool."; Biochimica et Biophysica Acta; vol. 22, 1956, pp. 405-411.

Ebright, Y.W.; et al; "N-(Iodoacetyl)-p-phenylenediamine-EDTA: A regent for high-efficiency incorporation of an EDTA-metal complex at a rationally selected site within a protein."; Bioconjugate Chemistry; vol. 4 (3), 1993, pp. 219-225.

Edwards, B.; et al; "Chemical studies on powdered keratins." Journal of Biological Chemistry; vol. 154, 1944, pp. 593-596.

Elleman, T.C.; et al; Amino acid sequences of alpha-helical segments from S-carboxymethylkerateine-A. Statistical analysis; Biochemical Journal; vol. 173 (2), 1978, pp. 387-391.

Elleman, T.C.; et al; "Periodicity in high sulphur proteins from wool"; Nature; vol. 246, 1973, pp. 530-531.

Elod, E.: et al.; "Reactions of wool fiber and alterations in the fine structure."; Melliand Textillber; vol. 21, 1940, pp. 385-388.

Elod, E.; et2 al.; The nature of the reactivity of wool. Melliand Textilber; vol. 21, 1940, pp. 617-622.

Elod, E; et al; "The structure and reactivity of the woolen fiber. IX. The effect of H2O2 on wool."; Melliand Textilber; vol. 23, 1942, pp. 313-316.

Elod,E. et al.; "The infiltration of heavy metal sulfides in the keratin fiber." Chem Ber. vol. 74B, 1941, pp. 1759-1762.

Eriksson, A.; et al.; "PDGF α- and β-receptors activate unique and common signal transduction pathaways."; The EMBO Journal; vol. 11, 1992, pp. 543-550.

Filshie, B.K. et al; "The Fine Structure of α—Keratin." Journal of Molecular Biology; vol. 3, 1961, pp. 784-786.

Filshie, B.K.; Rodgers, G.E.; "An electron microscope study of the fine structure of feather keratin."; The Journal of Cell Biology; vol. 13, 1962, pp. 1-12.

Frank, S.; et al.; "Transforming growth factors β1, β2, and β3 and their receptors are differentially regulated during normal and impaired wound healing." The Journal of Biological Chemistry; vol. 271, 1996, pp. 10188-10193.

Frankel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.

Fraser, B.R.D, et al; "Intermediate Filaments in α-keratins." Proceeedings of the National Academy of Sciences, USA.; Biochemistry; vol. 83, 1986, pp. 1179-1183.

Fraser, R.D.B.; et al; "Disulphide bonding in α-keratin."; International Journal of Biological Macromolecules; vol. 10, issue 2, 1988, pp. 106-112.

Fraser, R.D.B.; et al; "Microscopic Observations of the Alkaline-Thioglycollate Extraction of Wool."Short Communications, Wool Textile Research Laboratory; vol. 12, 1953, pp. 484-485.

(56) References Cited

OTHER PUBLICATIONS

Fraser, R.D.B.; et al; "Molecular organization in Alpha-Keratin."; Nature; vol. 193, 1962, pp. 1052-1055.
Fraser, R.D.B.; Gillispie, J.M.; "Wool structure and biosysnthesis." Nature vol. 126 1976, pp. 650-654.
Fraser, R.D.B.; Macrae, T.P.; "Helical models of feather keratin structure." Nature; vol. 195, No. 4847, 1962, pp. 1167, 1168.
Fraser, R.D.B.; MaCrae, T.P.; Rogers, G.E.; "Structure of Alpha-Keratin." Nature; vol. 183, 1959, pp. 592-594.
Fraser,R.D.B.; Gillespie, J.M.; Macrae,T.P.; "Tyrosine-rich proteins in keratins."; Comparative Biochemistry and Physiology; vol. 44B, 1973, pp. 943-949.
Fratini, A.; et al; "Dietary cysteine regulates the levels of mRNAs encoding a family of cysteine-rich proteins of wool."; Journal of Investigative Dermatology; vol. 102, 1994, pp. 178-185.
Frenkel, M.J. et al.; "Heterogeneity of tyrosine-rich proteins of wool."; Proceedings of the Australian Biochemical Society; vol. 7, 1974, p. 4.
Frenkel, M.J.; "Alkali susceptible amides in tyrosine-rich proteins of wool."; Proceedings of the Australian Biochemical Society; vol. 10, 1977, p. 21.
Frenkel, M.J.; et al.; "Studies of the ribonucleic-acids coding for the keratin complex of hair."; Proceedings of the Australian Biochemical Society; vol. 12, 1979, pp. 87.
Frenkel, M.J.; et al; "Factors influencing biosynthesis of tyrosine-rich proteins of wool."; Australian Journal of Biological Sciences; vol. 27, 1974, pp. 31-38.
Frenkel, M.J.; et al; "The keratin BIIIB gene family: isolation of cDNA clones and structure of a gene and a related pseudogene."; Genomics; vol. 4, No. 2, 1989, pp. 182-191.
Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.
Frenkel, M.J.; Gillespie, J.M.; Woods, E.F.;"The isolation and properties of a tyrosine-rich protein from wool: component 0.62."; European Journal Biochemistry; vol. 34, 1973, pp. 112-119.
Fujisawa, K.; et al; "Synthesis and characterization of zinc family thiolato complexes.";Abstracts, Symposium on Biofunctional Chemistry, vol. 14, 1999, pp. 52-53.
Gillespie, J.M. et al; "Evidence of homology in a high-sulphur protein fraction (SCMK-B2) of wool and hair α-keratins."; Biochemistry Journal; vol. 110, No. 2, 1968, pp. 193-198.
Gillespie, J.M. et al; "A comparative study of high-sulphur proteins from α-karatins." Comparative Biochemistry and Physiology; vol. 15, 1965, pp. 175-185.
Gillespie, J.M.; "Reaction of Sodium Borohydride with wool." Nature; vol. 183 No. 4657, 1959, pp. 322, 323.
Gillespie, J.M.; "Swelling of keratins in formic acid." Textile Research Journal; vol. 40, No. 9, 1970, pp. 853-855.
Gillespie, J.M.; "The isolation and properties of some soluble proteins from wool. (II) The preferential extracation of high-sulphur proteins."; Australian Journal of Biological Sciences; vol. 15, No. 1, 1962, pp. 262-277.
Gillespie, J.M.; "The isolation from wool of a readily extractable protein of low sulphur content." Biochimica et Biophysica Acta; vol. 27, 1958, pp. 225, 226.
Gillespie, J.M.; "The probable role and location of high-glycine-tyrosine proteins in the structure of keratins." Biopolymers, vol. 17, 1978, pp. 2743-2745.
Gillespie, J.M.; "The relation between the crimp of wool and its content of high-sulfur proteins."; Textile Research Journal; vol. 35, No. 12, 1965, pp. 1128-1129.
Gillespie, J.M.; "Keratin structure and changes with copper deficiency."; *Australian Journal of Dermatology*; vol. 14, No. 3, 1973, pp. 127-131.
Gillespie, J.M.; Broad, A.; "A further study on the dietary-regulated biosynthesis of high-sulphur wool proteins." Biochemistry Journal; vol. 112, 1969, pp. 41-49.

Gillespie, J.M.; Darskus, R.L.; "Relation between the tyrosine content of various wools and their content of a class of protiens rich in tyrosine and glycine,"; Australian Journal Biological Science; vol. 24, 1971, pp. 1189-1197.
Gillespie, J.M.; et al.; "Changes in the matrix proteins of wool and mouse hair following the administration of depilatory compounds." Australian Journal of Biological Sciences; vol. 33, 1980, pp. 125-136.
Gillespie, J.M.; et al.; "Proteins of the hard keratins of Echidna, Hedgehog, Rabbit, Ox and Man."; Australian Journal of Biological Sciences, vol. 30, 1977, pp. 401-409.
Gillespie, J.M.; et al; "The Diversity of Keratins"; Comparative Biochemistry and Physiology; vol. 47, No. 2,1974, pp. 339-346.
Gillespie, J.M.; et al; "Variable composition of hair and high-sulfur proteins in trichothiodystrophy."; Journal of Applied Cosmetology; vol. 7, No. 2, 1989, pp. 39-48.
Gillespie, J.M.; Frenkel, M.J.; "The macroheterogeneity of type I tyrosine-rich proteins of merino wool."; Australian Journal Biological Science; vol. 27, 1974, pp. 617-627.
Gillespie, J.M.; Inglis, A.S.; "High-sulphur proteins as a major cause of variation in sulphur content between α-keratins." Nature; vol. 207, 1965, pp. 1293, 1294.
Gillespie, J.M.; Marshall, R.C.; "A comparision of the proteins of normal and trichothiodystrophic human hair." The Journal of Investigative Dermatology; vol. 80, 1983, pp. 195-202.
Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.
Gillespie, J.M.; Reis, P.J.; "The dietary regulated biosynthesis of high-sulphur wool proteins."; Biochemistry Journal; vol. 98, 1966, pp. 669-677.
Gillespie, J.M.; Simmonds, D.H.; "Amino acid composition of a sulphur-rich protein from wool."; Biochimica et Biophysica Acta; vol. 39, 1960, pp. 538-539.
Gillespie,J.M.; "Proteins rich in glycine and tyrosine from keratins."; Comparative Biochemistry and Physiology; vol. 41B, 1972, pp. 723-734.
Gillis, J.N.; et al; "Selective retention of oxygen using chromatographic columns containing metal chelate polymers."; Analytical Chemistry; vol. 57(8), 1985, pp. 1572-1577.
Goddard, D.R. et al; "A Study on Keratin."; Journal of Biological Chemistry; vol. 106, 1934, pp. 605-614.
Gough, K.H. et al; "Amino acid sequences of alpha-helical segments from S-carboxymethylkerateine-A. Complete sequence of a type-I segment."; Biochemical Journal; vol. 173 (2), 1978, pp. 373-385.
Green, M.R.; Basketter, D.A.; Couchman, J.R.; Rees, D.A.; "Distribution and number of epidermal growth factor receptors in skin is related to epithelial cell growth.";Developmental Biology; vol. 100, 1983, pp. 506-512.
Greven, R.; et al.; "Morphological origin of the S-carboxymethyl kerateines of wool."; Textile Research Journal vol. 56; 1986, pp. 523-526.
Grotendorst, G.R.; et al.; "Novel transforming growth factor β response element controls the expression of the connective tissue growth factor gene."; Cell Growth and Differentiation; vol. 7, 1996, pp. 469-480.
Han, C.H.; et al; "Effect of glycerol addition on the structure and properties of soluble wool keratose films."; Journal of the Korean Fiber Society; vol. 37,No. 8, 2000, pp. 442-447.
Hanukoglu, I.; et al.; "The cDNA sequence of a human epidermal keratin: Divergence of the sequence but conservation of structure among intermediate filament proteins." Cell; vol. 31, 1982, pp. 243-252.
Happey, F.; "Polycrystralline structure of wool." Nature; No. 4218, 1950, pp. 397-398.
Happey, F.; Wormell, R. L.; "Regenerated keratin fibers from wool." Journal Textile Inst.; vol. 40, 1949, pp. T855-T869.
Happey, F.; Wormell, R. L.; "Regenerated keratin fibers."; Nature ; vol. 163, 1949, p. 18.
Harding, H.W.J.; et al; "Enzymic conversion of arginine to citrulline in a hair protein precursor."; Proceedings of the Australian Biochemical Society; ; vol. 9, 1976, pp. 18.

(56) References Cited

OTHER PUBLICATIONS

Harding, H.W.J.; Rogers, G.E.; "Formation of e (γ- Glutamyl) lysine cross-link in hair proteins. Investigation of transamidases in hair follicles." The Journal of Biochemistry; vol. 11, No. 15, 1972 pp. 2858-2863.

Hardy, M.H.; "The Secret life of the hair follicle."; Trends in Genetics; vol. 8, No. 2, 1992, pp. 55-60.

Harrap, B.S.; et al; "Soluble derivatives of feather keratin. (I) Isolation, fractionation and amiino acid composition." Biochemistry Journal; vol. 92, 1964, pp. 8-18.

Harris, M.; et al.; "Testing for oxidation damage of wool by alkali solubility." The Textile Manufacturer; vol. 63, 1937, pp. 36, 37.

Hewish, D.R.; et al; "In vitro growth and differentiation of epithelial cells derived from postembryonic hair follicles."; Australian Journal of Biological Sciences; vol. 35, No. 1, 1982, pp. 103-109.

Hiroshi, S.; et al; "Differential Thermal Analysis of component proteins from wool." Institute for Chemical Research, Kyoto University, Uji, Kyoto; vol. 38, 1982, pp. 517-522.

Hogg, D.M.; et al; "Amino acid sequences of alpha-helical segments from S-carboxymethylkerateine-A. Tryptic and chymotryptic peptides from a type II segment."; Biochemical Journal; vol. 173(2), 1978, pp. 353-363.

Horn, J.C.; Speakman, P.T.; "Relative molecular masses of reduced wool keratin polypeptides" Biochemistry Society Transcript, vol. 14, 1986, pp. 333, 334.

Hu, J.; et al; "Preparation of stable solution of keratin from human hair and structure and properties of the cast film."; Gaofenzi Cailiao Kexue Yu Gongcheng; vol. 18 (2), 2002, pp. 131-133.

Humphries, M.; "Protein-silicone copolymers."; Cosmetics News; vol. 16, No. 92, 1993, pp. 313-318.

Hynd, P.I., et al; "Amino acid transport in wool and hair follicles."; Experimental Dermatology; vol. 8, 1999, pp. 325-326.

Hübner, G.; et al.; "Strong induction of activin expression after injury suggests an important role of activin in wound repair."; Developmental Biology; vol. 173, 1996, pp. 490-498.

Igarashi, A.; et al.; "Regulation of connective tissue growth factor gene expression in human skin fibroblasts and during wound repair." Molecular Biology of the Cell; vol. 4, 1993, pp. 637-645.

Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.

Ito, H.; et al; "Biocompatability of denatured keratins from wool."; Kobunshi Ronbunshu; vol. 39(4), 1982, pp. 249-256.

Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.

Jahoda, C.A.B.; et al.; "Dermal-Epidermal Interactions: Adult Follicle-derived cell populations and hair growth."; Dermatologic Clinics; vol. 14, No. 4 1996, pp. 573-583.

Jenkins, B.J. ; et al; "Isolation and characterization of a sheep cysteine-rich cuticle keratin pseudogene."; DNA Sequence; vol. 3, 1992, pp. 181-184.

Jenkins, B.J.; et al; "Differential expression of genes encoding a cysteine-rich keratin in the hair cuticle."; Journal of Investigative Dermatology; vol. 103, 1994, pp. 310-317.

Jezowska-Trezebiatowska, B.; et al; "New cobalt (II) complexes, reversibly binding oxygen in aqueous solution."; Bulletin de l'Academie Polonaise des Sciences, Serie des Sciences Chimiques; vol. 20 (3), 1972, pp. 187-192.

Johnson, P.C.; et al.; "Oxidative metabolism and blood flow regulation: The search for the missing link."; Journal of Vascular Research; vol. 37 (1) 2000, pp. 83.

Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.

Jones, L.N.; "Studies on Microfibrils from alpha-Keratin."; Biochimica et Biophysica Acta ; vol. 446. 1976, pp. 515-524.

Jones, L.N.; et al; "Studies of developing human hair shaft cells in vitro."; Journal of Investigative Dermatology; vol. 90, No. 1, 1988, pp. 58-64.

Jozefowicz, M.; Jozefonvicz, J; "Functional Polymers and Cells"; Biomaterials; vol. 16, No. 4, 1988, pp. 831-870.

Katoh, K.; et al; "Multi-functionalization of fiber made of natural polymer."; Aichi-ken Sangayo Gijutsu Kenkyusho Kenkyu Hokoku; vol. 1, 2002, pp. 174-177.

Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.

Kawano, Y.; et al; "Film and gel of keratins."; Kagaku to Seibutsu; vol. 13 (5), 1975, pp. 291-292.

Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.

Kemp, D.J.; Rodgers, G.E.; "Immunological and immunofluorescent studies on keratin of the hair follicle."; Journal of Cell Science; vol. 7, 1970, pp. 273-283.

Kikkawa, M.; et al; "Solubilization of keratin. Solubilization of feather keratin by oxidation with performic acid."; Hikaku Kagaku,(Leather Chemistry) vol. 20(3), 1974, pp. 151-162.

Klement, V.; et al; "The use of computer-analysis for the quantification of 2-D electrophoretic hair keratin patterns—a pilot study."; Journal of the Forensic Science Society; vol. 24, No. 4, 1984, pp. 440.

Koga, J. et al.; "FTIR study on structural transformation of keratin films induced by stretching."; Journal of Applied polymer Science; vol. 37, 1989, pp. 2131-2140.

Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.

Kowalska, K.; et al; "New bacterial peptides isolated from structural proteins (keratin of porcine bristle)."; Peptides; Proceedings of the European Peptide Symposium, 25th, 1998, pp. 792-793.

Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.

Kuczek, E.S.; et al; "Sheep wool (glycine+tyrosine)-rich keratin genes: a family of low sequence homology."; European Journal of Biochemistry; vol. 166, 1987, pp. 79-85.

Kulkarni, V.G.; "Further studies on the microfibrils from wool keratin. Part I: the isolation of microfibrils."; Textile Research Journal; vol. 46, No. 11, 1976, pp. 833-835.

Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, pp. 818.

Kvedar, J.C.; et al.; "Cytokeratins of the bovine hoof : classification and studies on expression."; Biochimica et Biophysica Acta; vol. 884, 1986, pp. 462-473.

Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.

Laplaza, C.E.; et al; "Helix-loop-helix-peptide as scaffolds for the construction of bridged metal assemblies in proteins: the spectroscopic A- cluster structure in carbon monoxide dehydrogenase."; Journal of the American Chemical Society, vol. 123, (42), 2001, pp. 10255-10264.

Lee, K.Y.; "Characterization of Silk Fibroin/S-carboxymethyl kerateine surfaces: Evaluation of the biocompatibility by contact angle measurement."; Fibers and Polymers; vol. 2, No. 2, 2001, pp. 71-74.

Leeder, J.D.; et al; "Readily extracted proteins from Merino wool."; Textile Research Journal; vol. 52, No. 4, 1982, pp. 245-249.

Lennox, F.G.; "Protein fibers. Chemistry."; Review of Textile Progress Journal; vol. 17, 1967, pp. 81-97.

Lennox, F.G.; et al.; "Photochemical degradation of keratins."; Photochemistry and Photobiology; vol. 9, No. 4, 1969, pp. 359-367.

(56) References Cited

OTHER PUBLICATIONS

Leon, N.H.; "The chemical reactivity and modification of keratin fibres." Textile Progress vol. 7, No. 1975, pp. 1-81.
Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.
Ley, K.; et al; "Release of cuticle from wool by agitation in solutions of detergents."; Australian Journal of Biological Sciences; vol. 41, No. 2, 1988, pp. 163-176.
Ley, K.F.; et al; "Wool cuticle -new approaches to its production and protein characterization."; Proceedings of the Australian Biochemical Society; vol. 14, 1981, pp. 14.
Li, C-X.; et al; "Purification of natural antikeratin autoantibodies from natural human serum and their effect on human keratinocytes cultured in vivo."; British Journal of Dermatology; vol. 145, No. 5, 2001, pp. 737-748.
Lindley, H. et al.; "High-sulfur protein fractions of keratins."; *Applied Polymers Symposium;* vol. 18, No. 1, 1971, pp. 21-35.
Lindley, H.; et al; "The occurance of the Cys-Cys sequence in keratins."; Journal of Molecular Biology; vol. 30, No. 1, 1967, pp. 63-67.
Lindley, H.; et al; "The preparation and properties of a group of proteins from the high sulphur fraction of wool"; Biochemical Journal; vol. 128, No. 4, 1972, pp. 859-867.
Lindley, H.; et al; "The reactivity of the disulphide bonds of wool"; Biochemical Journal; vol. 139, No. 3, 1974, pp. 515-523.
Lindley,, H.; et al; "Disulphide interchange reactions involving cyclosystine and their relevance to problems of $\alpha$-keratin structure" Biochemical Journal; vol. 108, No. 4, 1968, pp. 701-703.
Lissizin, Th.; "Behavior of keratin sulfur and cystin sulfur, in the oxidation of these proteins by potassium permanganate." Biochemistry Bulletin vol. 4, 1915, pp. 18-23.
Lissizin, Th.; "The oxidation products of keratin by oxidation with permanganate." Z. Physiology Chem. vol. 173, 1928, pp. 309-311.
Liu, S.M.; et al; "Transsulfuration, protein synthesis rate and follicle mRNA in the skin of young Merino lambs in response to infusions of methionine and serine."; British Journal of Nutrition; vol. 83, No. 4, 2000, pp. 401-409.
Lotay, S.S.; Speakman, P.T.; "Three-chain merokeratin from wool may be a fragment of the microfibril component macromolecule"; Nature; vol. 265, 1977, pp. 274-277.
Lyons, K.M.; et al.; "Patterns of expression of murine Vgr-1 and BMP-2a RNA suggest that transforming growth factor-$\beta$-like genes coordinately regulate aspects of embryonic development." Genes & Development; vol. 3, 1989, pp. 1657-1668.
Mack, J.W.; Torchia, D.A.; Steinert, P.M.; "Solid-State NMR Studies of the Dynamics and Stucture of Mouse Keratin Intermediate Filaments."; Biochemistry; vol. 27, No. 15. 1988, pp. 5418-5426.
MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.
MacLaren, J.A.; "The extent of reduction of wool proteins by thiols." The Australian Journal of Chemistry; vol. 15,No. 4, 1962, pp. 824-831.
Marikovsky, M.; et al.; "Appearance of heparin-binding EGF-like growth factor in wound fluid as a response to injury."; Proceedings of the National Academy of Sciences, USA; vol. 90, 1993, pp. 3889-3893.
Marshall, R.C. et al; "High-sulfur proteins in mammalian keratins: a possible aid in classification."; Australian Journal of Zoology; vol. 25, No. 1, 1977, pp. 121-132.
Marshall, R.C.; "Successful isoelectric-focusing of wool low-sulphur proteins.";Journal of Chromatography; vol. 172, 1979, pp. 351-356.
Marshall, R.C.; "Analysis of the proteins from single wool fibers by two-dimensional polyacrylamide-gel electrophoresis."; Textile Research Journal; vol. 51, No. 2, 1981, pp. 106-108.

Marshall, R.C.; "Changes in wool low-sulphur and high-sulphur protein-components following chemical defleecing."; Textile Research Journal; vol. 51, No. 6, 1981, pp. 384-388.
Marshall, R.C.; "Characterization of the proteins of human hair and nail by electrophoresis."; Journal of Investigative Dermatology; vol. 80, No. 6, 1983, pp. 519-524.
Marshall, R.C.; "Cysteine-rich proteins of mouse hair."; Proceedings of the Australian Biochemical Society; vol. 8, 1975, pp. 4.
Marshall, R.C.; "Forensic identification of hairs by electrophoresis."; Journal of the Forensic Society; vol. 24, No. 4, 1984, pp. 340.
Marshall, R.C.; "Genetic variation in the proteins of human nail."; Journal of Investigative Dermatology; vol. 75, No. 3, 1980, pp. 264-269.
Marshall, R.C.; et al; "An investigation of the relationship of wool textile properties to fiber protein composition."; Proceedings of the International Wool Textile Research Conf.; vol. 1, 1990, pp. 266-275.
Marshall, R.C.; et al; "Examination of proteins of wool cuticle by two-dimensional gel-electrophoresis."; Textile Research Journal; vol. 56, No. 12, 1986, pp. 772-774.
Marshall, R.C.; et al; "High sulphur proteins and a-keratins II. lsolatioin and partial characterization of purified components from mouse hair."; Australian Journal of Biological Sciences.; vol. 29, 1976, pp. 11-20.
Marshall, R.C.; et al; "High sulphur proteins from $\alpha$-keratins I. Heterogeneity of the proteins from mouse hair."; Australian Journal of Biological Sciences; vol. 29, 1976, pp. 1-10.
Marshall, R.C.; et al; "Possible identification of specialty fibers y electrophoresis."; Textile Research Journal; vol. 54, No. 2, 1984, pp. 126-128.
Marshall, R.C.; et al; "Protein changes after short thermal treatments of wool fibrics."; Textile Research Journal; vol. 53, No. 12, 1983, pp. 792-794.
Marshall, R.C.; et al; "Sequence studies of wool proteins rich in glycine and aromatic residues."; Proceedings of the Australian Biochemical Society; vol. 12, 1979, pp. 12.
Marshall, R.C.; Gillespie, J.M.; "The keratin proteins of wool, horn and hoof from sheep." Australian Journal of Biological Sciences; vol. 30, 1977, pp. 389-400.
Marshall, R.C; et al.; "Heterogeneity and incomplete disulfide reduction in the high sulphur proteins of wool." Australian Journal of Biological Sciences; vol. 31, 1978, pp. 219-229.
Martin, P. "Wound Healing-Aiming for Perfect Skin Regeneration."; Science; vol. 276, 1997, pp. 75-81.
Mason, E.D.; et al.; "Dorsal midline fate in Drosophila embryos requires twisted gastrulation, a gene encoding a secreted protein related to human connective tissue growth factor." Genes and Development vol. 8, 1994, pp. 1489-1501.
Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29.
Mazzoni, M.C.; et al; "Blood and plasma viscocity and microvascular function in hemodilution. A perspective from LaJolla, California."; European Surgical Research; vol. 34, (1-2), 2002 Ref. 35.
McCloghry, C.E.; et al; "Wool follicles initiate, develop and produce fibres in ovine foetal skin grafts."; Proceedings of the Australian Society of Animal Production; vol. 18, 1990, pp. 518.
McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.
McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.
Mies, H.H.; et al.; "Preparation of soluble proteins from wool."; Leder; vol. 39, 1988, pp. 1-9.
Mies, H.H.; Zahn, H.; "Chromatographic and electrophoretic investigations of the properties of unprotected low-sulphur wool keratins."; Journal of Chromatography; vol. 405, 1987, pp. 365-370.
Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.

(56) References Cited

OTHER PUBLICATIONS

Miwa, M.; et al; "Effects of fiber length on the tensile strength of epoxy/glass fiber and polyester/glass fiber composites." Journal of Applied Polymer Science; vol. 25, 1980, pp. 795-807.

Miyamoto, T.: et al; "Sorption Behavior of Heavy Metal Ions on S-Subtituted Kerateine Gels." Institute for Chemical Research; vol. 34, No. 10, 1978, pp. T-447-T-454.

Moll, R.; et al.; "The catalog of humans cytokeratins: Patterns of expression in normal epithelia, tumors and cultured cells." Cell; vol. 31, 1982, pp. 11-24.

Mueller, R.V.; et al.; "The effect of insulinlike growth factor I on wound healing variables and macrophages in rats." Archives of Surgery; vol. 129, 1994, pp. 262-265.

Nakamura, A.; et al; "Cysteine-containing oligopepetide model complexes of iron-sulfur proteins.", Advances in Inorganic Chemistry; vol. 33, 1989, pp. 39-67.

Nakamura, Y.; et al; "Cystine in wool. Relation between sulfhydryl group and supercontraction." Sen-i Gakkaishi, vol. 16, 1960, pp. 852-858.

Nancarrow, M.J. et al; "Expression of ornithine decarboxylase during embryonic development of wool follicles."; Experimental Dermatology; vol. 8, 1999, pp. 362-368.

Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227.

Norman, J.A.T.; et al; "Reversible complexes for the recovery of dioxygen."; Procedings of the Annual IUCCP Symposium; 1987, pp. 107-125.

Okamoto, S.; "Formation of films from some proteins."; Nippon Shokuhin Kogyo Gakkaishi; vol. 24(1), 1977, pp. 40-50.

O'Shea, J.M.; et al; "The effect of ultrasonic irradiation on proteins." Australian Journal of Biological Sciences; vol. 26,1973, pp. 583-590.

Osterberg, R.; "Metal complexes of peptides."; Metal Catalog Lipid Oxidation; Sv. Inst. Konserveringsforsk, Symposium, Goteberg Sweden, 1967, pp. 119-127.

Panteleyev, A.A.; et al.; "Hair follicle predetermination."; Journal of Cell Science; vol. 114, 2001, pp. 3419-3431.

Parry, D.A.D.; et al; "Fibrous proteins: Scientific, Industrial and Medical aspects."; An Academic Press Fast Publication; vol. 1, 1979, pp. 1-132.

Parry, D.A.D.; et al; "Structure of α-keratin: Structural implication of the amino acid sequences of the type I and type II chain segments."; Journal of Molecular Biology; vol. 113, 1977, pp. 449-454.

Pauling, L.; Corey, R.B.; "The structure of feather rachis keratin." Proceedings of the National Academy of Sciences; vol. 37,No. 5, 1951, pp. 256-261.

Pauling, L.; Corey, R.B.; "The structure of hair, muscle, and related proteins."; Proceedings of the National Academy of Sciences; vol. 37, No. 5, 1951, pp. 261-271.

Peters, L.; "Affinity of ions for keratin."; Journal of Textile Institute; vol. 58, No. 4, 1967, pp. 179-180.

Peus, D., et al.; "Growth factors in hair organ development and the hair growth cycle." Dermatologic Clinins; vol. 14, No. 4, 1996, pp. 559-572.

Philpott, M.P.; et al.; "Whole hair follicle culture." Dermatologic Clinics; vol. 14, No. 4, 1996, pp. 595-607.

Powell, B.C.; "The keratin proteins and genes of wool and hair."; Wool Technology and Sheep Breeding; vol. 44, No. 2, 1996, pp. 100-118.

Powell, B.C.; et al; "The Notch signalling pathway in hair growth."; Mechanisms of Development; vol. 78, 1988, pp. 189-192.

Powell, B.C.; et al; "Characterization of a gene encoding a cysteine-rich keratin associated protein synthesized late in rabbit hair follicle differentiation."; Differentiation; vol. 58, 1995, pp. 227-232.

Powell, B.C.; et al; "Characterization of hair (wool) keratin intermediate filament gene domain."; Journal of Investigative Dermatology; vol. 102, 1994, pp. 171-177.

Powell, B.C.; et al; "Mammalian keratin gene families: organization of genes coding for the B2 high sulphur proteins of sheep wool."; Nucleic Acids Research; vol. 11, 1983, pp. 5327-5346.

Powell, B.C.; et al; "Regulation of Keratin Gene Expression in Hair Follicle Differentiation." Annals New York Academy of Sciences; vol. 642, 1991, pp. 1-20.

Powell, B.C.; et al; "The role of keratin proteins and their genes in the growth, structure and properties of hair."; EXS; vol. 78, 1997, pp. 59-148 Ref: 284.

Powell, B.C.; et al; "Transgenic sheep and wool growth: possibilities and current status."; Reproduction, Fertility, and Development; vol. 6, 1994, pp. 615-623.

Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.

Powell, B.C.; Rodgers, G.E.; "Cyclic hair-loss and regrowth in the transgenic mice overexpressing and intermediate filament gene."; The Embo Journal vol. 9, No. 5, 1990, pp. 1485-1493.

Rana, T.M.; et al; "Specific cleavage of a protein by an attached iron chelate."; Journal of the American Chemical Society; vol. 112 (6), 1990, pp. 2457-2458.

Randall, V.A.; "The use of dermal papilla cells in studies of normal and abnormal hair follicle biology."; Dermatologic Clinics; vol. 14, No. 4 1996 pp. 585-594.

Ranford, J.D.; et al; "Matallodrugs. The role of thiolate proteins and metal-thiolate complexes."; Metallothioneins, Conference General Review; 1992, pp. 408-435.

Ranshoff, S.; et al; "Synthesis and characterization of new dioxygen carriers: a reexamination of the fly-over ligand system."; Inorganic Chemistry; vol. 29(16), 1990, pp. 2945-2947.

Raphael, K.A.; et al; "Protein and amino acid composition of hair from mice carrying the naked (N) gene."; Genetic Research, vol. 44, No. 1, 1984, pp. 29-38.

Rappolee, D.A.; et al.; "Wound macrophages express TGF-α and other growth factors in vivo: Analysis by mRNA phenotyping."; Science; vol. 241, 1988, pp. 708-712.

Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.

Reis, P.J.; "Influence of dietary protein and methionine on the sulphur content and growth rate of wool in the millk fed lambs" Australian Journal of Biological Science; vol. 23, No. 1, 1970, pp. 193-200.

Reis, P.J.; "The growth and composition of wool—III. Variations in the sulphur content of wool."; Australian Journal of Biological Sciences; vol. 18, 1965, pp. 671-687.

Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.

Reis, P.J.; et al; "The utilization of abomasal supplements of proteins and amino acids by sheep with special reference to wool growth"; Australian Journal of Biological Sciences; vol. 25, 1972, pp. 1057-1071.

Reis, P.J.; et al; "The influence of abomasal and intervenous supplements of sulphur containing amino acids on wool growth rate"; Australian Journal of Biological Sciences; vol. 26, No. 1, 1973, pp. 249-258.

Reis, P.J.; et al; "The nutritional control of the growth and properties of mohair and wool fibers: a comparative review"; Journal of Animal Science; vol. 72, No. 7, 1994, pp. 1899-1907.

Reis, P.J.; Gillespie, J.M.; "Effects of phhenylalanine and the analogues of methionine and phenylalanine on the composition of wool and mouse hair."Australian Journal of Biological Sciences; vol. 38, No. 2 pp. 151-163.

Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.

Reis, P.J.; "Variations in the S content of wool."; Biology Skin Hair Growth, Proceedings Symposium; 1964, pp. 365-375.

(56) References Cited

OTHER PUBLICATIONS

Rogers, G.E.; "Some observations on the proteins of the inner root sheath cells of hair follicles." Biochimica et Biophysica Acta; vol. 29. 1958, pp. 33-43.
Rogers, G.E.; et al; "Keratin protofilaments and ribosomes from hair follicles."; Nature, vol. 205, 1965, pp. 77-78.
Rogers, G.E. et al.; "An approach to the investigation of protein biosynthesis in hair follicles." *Biology of Skin Hair Growth*, Proceedings, 1965, pp. 329-343.
Rogers, G.E.; "Genetic engineering for novel fibres."; Journal of the Textile Institute; vol. 91, part 3, Special Issue, 2000, pp. 24-31.
Rogers, G.E.; "Improvement of wool production through genetic engineering."; Trends in biotechnology (Personnal edition); vol. 8, 1990, pp. 6-11, 32 references.
Rogers, G.E.; "Proteins of the inner-root-sheath cells of hair follicles."; Biochimica et Biophysica Acta; vol. 29, 1958, pp. 33-43.
Rogers, G.E.; "Structural and biochemical features of the hair follicles."; Epidermis; 1964, pp. 179-236.
Rogers, G.E.; "Structure and biochemistry of keratin."; The Biological Basis of Medicine.; vol. 6, 1969, pp. 21-57.
Rogers, G.E.; "Synthesis and cross-linking in the structure and growth of hair keratins." Clinics in Dermatology; vol. 6, No. 4, 1988, pp. 26-31.
Rogers, G.E.; et al; "Protein biosynthesis in hair follicles."; Biology of Skin Hair Growth., Proceedings ; 1965, pp. 329-343.
Rogers, G.E.; et al; "A procedure for the culture of hair follicles as functionally intact organoids."; Clinics in Dermatology; vol. 6, No. 4, 1988. pp. 36-41.
Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184.
Rogers, G.E.; et al; "Organization and expression of hair follicle genes."; Journal of Investigative Dermatalogy; vol. 101, 1993, pp. 50 S-55 S.
Rogers, G.E.; et al; "Themes in the molecular structure of hair—discussion." Annals New York Academy Science; vol. 642, 1991, pp. 100-106.
Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.
Ross, S.A.; et al; "Nickel complexes of cysteine—and cystine-containing peptides: Spontaneous formation of disulfide-bridged dimers at neutral pH."; Inorganic Chemistry, vol. 37 (20), 1998, pp. 5358-5363.
Rouse, J.G.; et al; "A review of keratin-based biomaterials for biomedical applications." Materials; vol. 3, 2010, pp. 999-1014.
Rowlands, R.J.; "Periodicity in high-sulphur proteins from wool."; Nature; vol. 246, No. 5434, 1973, pp. 530-531.
Sadova, S. F.; et al; "Grafting of vinyl monomers onto wool keratin in an oxidation-reduction system."; Zh. Vses. Khim. O-va, vol. 12(5), 1967, pp. 596-597.
Sander, G.; et al; "Expresssion of the homeobox gene, Barx2, in wool follicle development."; Journal of Investigative Dermatology; vol. 115, No. 4, 2000, pp. 753-756.
Sauk, J.J. et al; "Reconstitution of cytokeratin filaments in vitro: Further evidence for the role of nonhelical peptides in filament assembly."; The Journal of Cell Biology; vol. 99, 1984, pp. 1590-1597.
Schaller, J.; et al; "Membranes prepared from keratin-polyacrylonitrile graft copolymers." Journal of Applied Polymer Sciences; vol. 25(5), 1980, pp. 783-794.
Schornig, M.; Neumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, p. 1471-1479.
Schrooyen, P.M.M.; et al; "Biodegrable films from selectively modified feather keratin dispersions."; Polymer Preprints; vol. 39, No. 2, 1998, pp. 160.
Schrooyen, P.M.M.; et al; "Polymer films from chicken feather keratin."; Book of Abstracts, American Chemical Society National Meeting Boston, 1998.
Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.
Alexander, P.; Earland, C.; "Structure of wool fibers—Isolation of an $\alpha$and $\beta$-protein in wool." Nature; vol. 166, 1950.
Almog, J.; et al; "Reversible binding of dioxygen to mesoporphyrin IX derivatives at low temperatures."; Journal of the American Chemical Society; vol. 96(17), 1974, pp. 5600-5501.
Almog, J.; et al; "Reversible oxygenation and autoxidation of a capped porphyrin iron (II) complex."; Journal of the American Chemical Society; vol. 97(1), 1975, pp. 227-228.
Amiya, T.; et al; "Conformational studies of the $\alpha$-helical proteins from wool keratins by c.d." International Journal of Biological Macromolecules; vol. 4, 1982, pp. 165-172.
Ando, H. ; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.
Ashkenasy, G.; et al; "Assemblies of "hinged" iron-porphyrins as potential oxygen sensors."; Journal of the American Chemical Society; vol. 122, No. 6, 2000, pp. 1116-1122.
Baldwin, J.E.; et al; "Binding of dioxygen to iron (II), Reversible behavior in solution."; Journal of the American Chemical Society; vol. 95 (17), 1973, pp. 5757-5759.
Barr, M.; "Oxidation, reduction and hydroysis of wool keratin."; Iowa State Coll. Journal of Science, vol. 12, 1937, pp. 106-107.
Bawden, C.S.; et al; "Expression of bacterial cysteine biosynthesis genes in transgenic mice and sheep: toward a new in vivo acid biosynthesis pathway and improved wool growth." Transgenic Research; vol. 4,1995, pp. 87-104.
Bawden, C.S.; et al; "Expression of wool intermediate filament keratin transgene in sheep fibre alters structure."; Transgenic Research; vol. 7, 1998, pp. 273-287.
Bawden, C.S.; et al; "Improvement of wool quality by transgenesis."; Science Update, Conf: OECD, 2001, pp. 67-76.
Bawden, C.S.; et al; "Sheep transgenesis with keratin and non-keratin genes: expression in the wool follicle for the modified fibre properties and growth rates."; Experimental Dermatology; vol. 8, 1999, pp. 342-343.
Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.
Besse, D.; et al; "Synthesis of selenocysteine peptides and their oxidation to diselenidebridged compounds."; Journal of Peptide Science; vol. 3 (6), 1997, pp. 442-453.
Bettex-Galland, M. et al.; "Advances in Protein Chemistry." Academic Press, vol. 20, 1965.
Bhatnagar, G.M. et al.; "Difference sprectra of kerateine-B."; *International Journal of Protein Research*; vol. 1 No. 3, 1969, pp. 213-219.
Bhatnagar, G.M.; et al; "Assessment of confirmational changes in low-sulfur S-(carboxymethyl)keratin from wool."; Australian Journal of Biological Sciences; vol. 20, No. 4, 1967, pp. 827-836.
Bhatnagar, G.M.; et al; "The conformation of the high sulphur proteins of wool. I the preparation and properties of a water soluble metakeratin."; International Journal of Protein Research; vol. 1 (3), 1969, pp. 199-212.
Bhatnagar, G.M.; et al; "The conformation of the high-sulphur proteins of wool. II—Difference spectra of kerateine-B." International Journal of Protein Research I; 1969, pp. 213-219.
Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.
Blessing, M.; et al.; "Transgenic mice as a model to study the role of TGF-$\beta$-related molecules in hair follicles." Genes and Development; vol. 7, 1993, pp. 204-215.
Bradbury, J.H.; "The structure and chemistry of keratin fibers." Advanced Protein Chemistry; vol. 27, 1973, pp. 111-211.

(56) References Cited

OTHER PUBLICATIONS

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histiological components of keratin fibers and analyses of cuticles."; Nature; vol. 210, No. 5043, 1966, pp. 1333-1334.

Breinl, F.; et al; "The oxidative breaking up of keratin through treatment with hydrogen peroxide." Z.Physiol. Chemistry; vol. 52, 1907, pp. 158-169.

Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.

Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.

Brunner, H.; Brunner, A.; "Fractionation of tyrosine-rich proteins from oxidized wool by ion-exchange chromotography and preparative electrophoresis."; European Journal Biochemistry; vol. 32, 1973, pp. 350-355.

Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260.

Cameron, J.H.; et al; "Nickel (II) and cobalt (II) complexes of potentially quinquedentate macrobicyclic ligands. Reversible binding to dioxygen to a cobalt (II) complex."; Journal of the Chemical Society, Dalton Transactions: Inorganic Chemistry; vol. 3, 1993, pp. 397-402.

Campbell, M.E.; Whiteley, K.J.; Gillespie, J.M.; "Compositional studies of high and low-crimp wools."; Australian Journal of Biological Sciences; vol. 25, 1972, pp. 977-987.

Carey, J.R.; et al; "Design and synthesis of novel metalloproteins through reversible encapsulation of metal complexes by proteins." Abstract of Papers, 222nd ACS National Meeting, 2001.

Chatani, E.; et al; "A film formation technology of wool keratin."; Textile and Fashion; vol. 14(5), 1997,pp. 227-235.

Chatani, E.; et al; "Research on merchandizing technology of wool keratin. Film formation technology of wool keratin."; Owari Textile Research Annual Report No. 93, 1998, pp. 93-101.

Clark, R.A.F. Editor; "The Molecular and Cellular Biology of Wound Repair."; Plenum Press 2nd Edition, 1996, 1988.

Japanese Office Action Corresponding to Japanese Patent Application No. 2008-555408; Dispatch Date: Apr. 24, 2012; 3 pages (Foreign Text Only).

International Search Report and Written Opinion, PCT/US10/24041, mailed Mar. 23, 2010.

* cited by examiner

KERATIN BIOMATERIALS FOR CELL CULTURE AND METHODS OF USE

RELATED APPLICATION

This application claims the benefit under 35 U.S.C. §120 and is a continuation-in-part of U.S. application Ser. No. 12/192,490, filed Aug. 15, 2008, and published as US 2009/0047260 A1 on Feb. 19, 2009, which claims the benefit under 35 U.S.C. §119(e) of U.S. Provisional Patent Application Ser. No. 60/956,454, filed Aug. 17, 2007, the disclosure of each of which is incorporated herein by reference in its entirety.

This application also claims the benefit under 35 U.S.C. §119(e) of U.S. Provisional Patent Application Ser. No. 61/152,562, filed Feb. 13, 2009, the disclosure of which is incorporated herein by reference in its entirety.

FIELD OF THE INVENTION

The present invention is generally related to keratin-based biomaterials and the use thereof for culture and delivery of cells.

BACKGROUND OF THE INVENTION

Cell culture of mammalian cells has long been used for the production of many vaccines and genetically engineered proteins. Attachment-dependent cells have historically been cultivated on the walls of roller bottles or non-agitated vessels such as tissue culture flasks, which are used in many laboratories. As the need has developed to provide large amounts of certain antiviral vaccines, genetically engineered proteins, and other cell-derived products, attempts have been made to develop new systems for large-scale production of cells. One solution has been to increase the growth surface area per unit vessel volume and to implement convenient and appropriate environmental controls. Some of these technologies involved the use of packed-glass beads, stacked plates, rotating multiple tubes, and roller bottles with spiral films inside.

Using microcarriers for cell culture increases the surface area of growth by allowing cells to grow as monolayers on the surface of small spheres or other globular micro-structures, or as multilayers in the pores of macroporous structures. First described in 1967 by van Wezel (van Wezel, A. L. "Growth of Cell-Strains and Primary Cells on Micro-carders in Homogeneous Culture" (1967) Nature 216:64-65), early microcarriers consisted of positively charged DEAE-dextran beads suspended in culture media in a stirred vessel. Cells would attach to the bead surface and grow as a monolayer.

Various other materials have been used for microcarriers and microcarrier and cell culture substrate coatings since van Wezel's DEAE-dextran beads (see, e.g., review in van der Velden-de Groot, Cytotechnology (1995) 18:51-56). However, new materials are needed in order to provide optimal cell culture conditions for various applications. Additionally, biocompatible microcarriers are needed that may be used directly in methods of treatment, without the need for cell harvesting.

The ability of complex substrates to support cell growth in vitro has been reported, and matrix products supporting such growth are commercially available. For example, there is Human Extracellular Matrix and BD Matrigel™ Basement Membrane Matrix (BD Biosciences). Human Extracellular Matrix is a chromatographically partially purified matrix extract derived from human placenta and comprises laminin, collagen IV, and heparin sulfate proteoglycan. (See U.S. Pat. No. 4,829,000 to Kleinman et al.). BD Matrigel™ is a soluble basement membrane extract of the Engelbreth-Holm-Swarm (EHS) tumor, gelled to form a reconstituted basement membrane. Both of these matrix products require costly biochemical isolation, purification, and synthesis techniques and thus production costs are high.

Therefore, alternative compositions are needed which can support cell growth in vitro. Alternative materials with improved characteristics and/or lower cost would be beneficial.

SUMMARY OF THE INVENTION

Provided herein is a cell culture substrate comprising a keratin coating, said keratin optionally in the form of a gel or a freeze dried scaffold. In some embodiments, the substrate comprises polystyrene or polypropylene. In some embodiments, the substrate is a petri dish, a 2-well plate, 6-well plate, a 12-well plate, a 24-well plate, or a 96-well plate. In some embodiments, the substrate is an insert configured to be placed into a cell culture dish (e.g., a petri dish, a 6-well plate, a 12-well plate, or a 24-well plate), and in some embodiments the substrate comprises polycarbonate or polyester.

In some embodiments, the keratin is selected from the group consisting of: keratose, kerateine, and combinations thereof. In some embodiments, the keratin is selected from the group consisting of: acidic keratose, basic keratose, acidic kerateine, basic kerateine, and combinations thereof. In some embodiments, the keratin is selected from the group consisting of: $\alpha+\gamma$-keratose, $\alpha$-keratose, $\gamma$-keratose, basic $\alpha$-keratose, acidic $\alpha$-keratose, basic $\gamma$-keratose, acidic $\gamma$-keratose, $\alpha+\gamma$-kerateine, $\alpha$-kerateine, $\gamma$-kerateine, basic $\alpha$-kerateine, acidic $\alpha$-kerateine, basic $\gamma$-kerateine, acidic $\gamma$-kerateine, and combinations thereof.

Further provided is a method for growing cells in vitro including the steps of: contacting said cells to a cell culture substrate comprising a keratin coating, said keratin optionally in the form of a gel or a freeze dried scaffold, wherein said cells adhere to said keratin coating; and growing said cells in vitro under conditions conducive to the proliferation of said cells. In some embodiments, the cells are stem cells. In some embodiments, the cells are embryonic stem cells, amniotic fluid stem cells, or multipotent stem cells. In some embodiments, the cells are pancreatic islet cells. In some embodiments, the cells are primary cells isolated from tissue.

In some embodiments, the keratin is selected from the group consisting of: keratose, kerateine, and combinations thereof. In some embodiments, the keratin is selected from the group consisting of: acidic keratose, basic keratose, acidic kerateine, basic kerateine, and combinations thereof. In some embodiments, the keratin is selected from the group consisting of: $\alpha+\gamma$-keratose, $\alpha$-keratose, $\gamma$-keratose, basic $\alpha$-keratose, acidic $\alpha$-keratose, basic $\gamma$-keratose, acidic $\gamma$-keratose, $\alpha+\gamma$-kerateine, $\alpha$-kerateine, $\gamma$-kerateine, basic $\alpha$-kerateine, acidic $\alpha$-kerateine, basic $\gamma$-kerateine, acidic $\gamma$-kerateine, and combinations thereof.

Also provided is a cell culture media comprising a keratin, e.g., a keratose, a kerateine, or combinations thereof. In some embodiments, the media further includes serum. In other embodiments, the media is serum-free.

In some embodiments, the keratin is selected from the group consisting of: keratose, kerateine, and combinations thereof. In some embodiments, the keratin is selected from the group consisting of: acidic keratose, basic keratose, acidic kerateine, basic kerateine, and combinations thereof. In some embodiments, the keratin is selected from the group consisting of: $\alpha+\gamma$-keratose, $\alpha$-keratose, $\gamma$-keratose, basic $\alpha$-keratose, acidic $\alpha$-keratose, basic $\gamma$-keratose, acidic $\gamma$-keratose, α+γ-kerateine, α-kerateine, γ-kerateine, basic α-kerateine, acidic α-kerateine, basic γ-kerateine, acidic γ-kerateine, and combinations thereof.

DETAILED DESCRIPTION OF THE PREFERRED EMBODIMENTS

Figure 1:
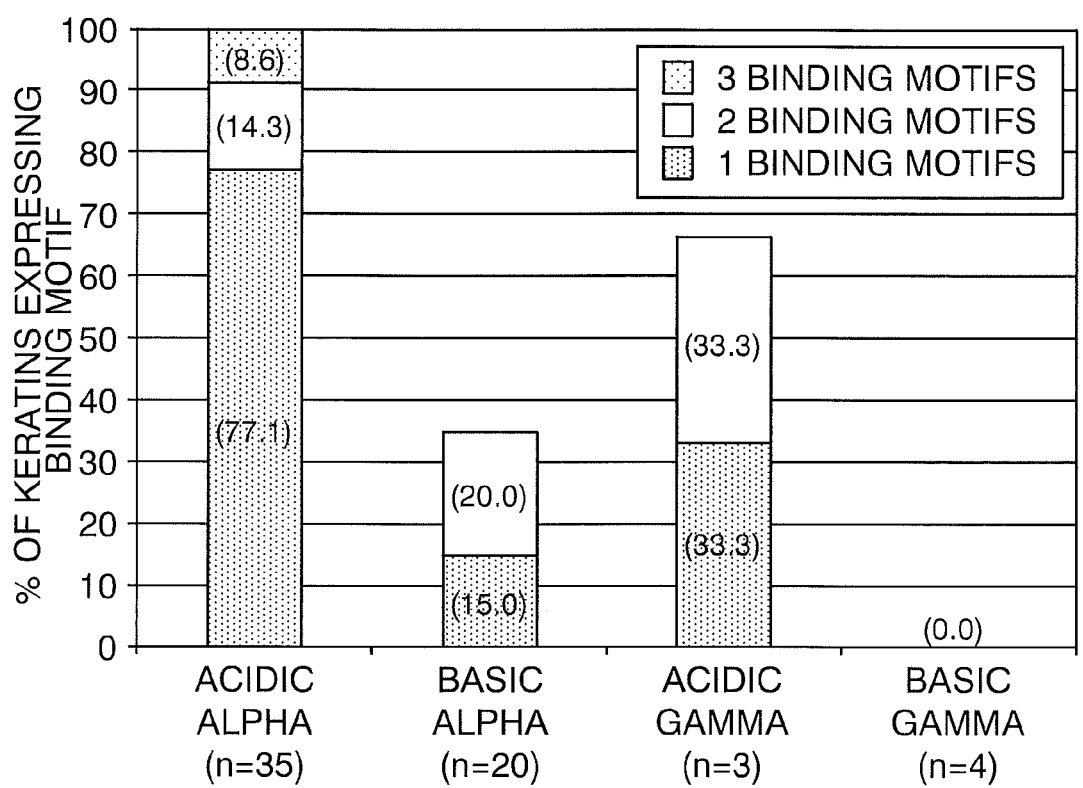
FIG. 1. Select binding domains found in known keratins. Peptide binding motifs are concentrated in the alpha keratins, particularly the acidic form.
Figure 2:
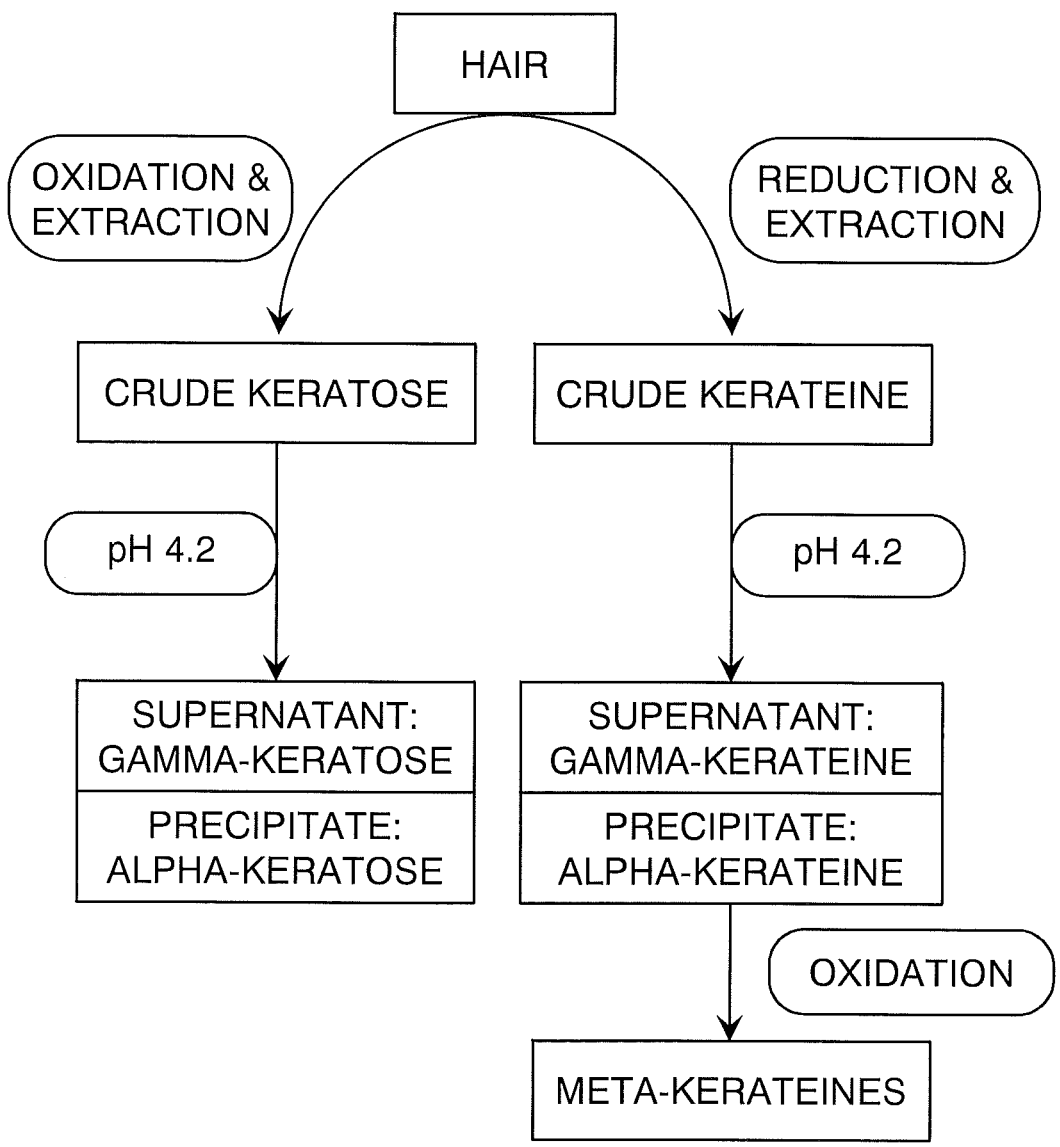
FIG. 2. General schematic illustrating the production of various keratin derivatives from hair.

Described herein are keratin compositions useful in cell culture. In some embodiments the keratins are biocompatible, promote cell growth, promote cell adhesion and provide an excellent substrate for cell culture. Keratin compositions described herein may be used as coatings, gels, three-dimensional scaffolds, additives to cell culture media, microcarriers, etc. The keratin substrates may also be used to deliver cells, e.g., for cell therapy applications.

The disclosures of all cited United States patent references are hereby incorporated by reference to the extent they are consistent with the disclosure herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

Keratins are a family of proteins found in the hair, skin, and other tissues of vertebrates. Hair is a unique source of human keratins because it is one of the few human tissues that is readily available and inexpensive. Although other sources of keratins are acceptable feedstocks for the present invention, (e.g. wool, fur, horns, hooves, beaks, feathers, scales, and the like), human hair is preferred for use with human subjects because of its biocompatibility. The human hair can be end-cut, as one would typically find in a barber shop or salon.

"Keratin derivative" as used herein refers to any keratin fractionation, derivative, subfamily, etc., or mixtures thereof, alone or in combination with other keratin derivatives or other ingredients, including, but not limited to, alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure.

I. Cells

"Cell" or "cells" as used herein may be any type of eukaryotic or prokaryotic cell, without limitation. Mammalian cells (including mouse, rat, dog, cat, monkey and human cells) are in some embodiments preferred. "Isolated" as used herein signifies that the cells are placed into conditions other than their natural environment. Tissue or cells are "harvested" when initially isolated from a subject, e.g., a primary explant. "Cell culture" is the growth or proliferation of cells in vitro.

Cells that can be cultured on the keratin coating and/or substrates disclosed herein include, but are not limited to, eukaryotic cells and other microorganisms (e.g., yeast cells) such as stem and progenitor cells (whether embryonic, fetal, or adult), germ cells, somatic cells, cells strains or cell lines, etc., without limitation (See, e.g., U.S. Pat. No. 6,808,704 to Lanza et al.; U.S. Pat. No. 6,132,463 to Lee et al.; and U.S. Patent Application Publication No. 2005/0124003 to Atala et al.), as well as prokaryotic cells, including, but not limited to, bacteria (e.g., those that are genetically modified to produce specific biological molecules of interest such as therapeutic compounds). Similarly, "cells of interest" are cells which are, or are intended to be, cultured using the methods disclosed herein. For example, cells of interest may be a particular type of cell isolated from a tissue or culture.

Cells may be identified by methods known in the art, e.g., based upon properties that distinguish one cell type from another, e.g., density, size, unique markers, unique metabolic pathways, nutritional requirements, protein expression, protein excretion, etc. Unique markers may be selected with fluorescent activated cell sorting (FASC), immunomagnetic bead sorting, magnetic activated cell sorting (MASC), panning, etc. Unique metabolic pathways and nutritional requirements may be assessed by varying the makeup and/or quantity of nutritional ingredients of the medium on which cells are grown, particularly in a serum-free environment. Protein expression and/or excretion may be detected with various assays, e.g., ELISA.

"Pancreatic cells" include those cells normally found in the pancreas, and include pancreatic islet cells, e.g., glucagon-synthesizing A ($\alpha$) cells, insulin-producing B ($\beta$) cells, D ($\delta$) cells, etc., and any combination thereof. Pancreatic islet cells cultured by the processes described herein are useful for, among other things, production of insulin, implantation into a subject to treat diabetes (including type I and type II diabetes), etc.

"Kidney cells" include those cells normally found in the kidney, and include interstitial cells (e.g., interstitial peritubular cells which secrete erythropoietin), endothelial cells, etc., or any combination thereof. Kidney cells cultured by the processes described herein are useful for, e.g., production of erythropoietin, implantation into a subject to treat anemia, etc.

"Nervous system cells" or "nerve cells" include those cells normally found in the central and/or peripheral nervous system, including neuronal cells (e.g., cortical neurons, hippocampal neurons, dopaminergic neurons, cholinergic neurons, adrenergic neurons, noradrenergic neurons, etc., including any combination thereof), and glial cells (e.g., neuroglia, astrocytes, oligodendrocytes, Schwann cells, etc., including any combination thereof). Nerve cells cultured by the processes described herein are useful, among other things, for implantation into a subject to treat nerve injury or degenerative diseases such as Parkinson's disease and Alzheimer's disease.

"Liver cells" include those cells normally found in the liver, and include hepatoblasts, hepatocytes, hepatic stellate cells, Kupffer cells, sinusoidal endothelial cells, etc., including any combination thereof. Livers cells cultured using the processes described herein are useful, among other things, for implantation into a subject to treat acute or chronic liver disease.

"Bone cells" include those cells normally found in bone, and include osteoblasts, osteoclasts, osteocytes, and any combination thereof. Bone cells cultured using the processes described herein are useful for, among other things, implantation into a subject to treat bone fractures or defects, and/or promote bone healing.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular joints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity. Cartilage cells cultured using the processes described herein are useful for, among other things, implantation into a subject to treat cartilage injury or disease.

"Muscle cells" include those cells normally found in muscle tissue, including smooth muscle cells, cardiac muscle cells, skeletal muscle cells, and any combination thereof. Muscle cells cultured with the processes described herein are useful for, among other things, implantation into a subject to treat muscle injuries or defects, and/or promote muscle healing.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin cultured with the processes described herein are useful for, e.g., implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

Cells that may be cultured using the procedures disclosed herein include stem cells. "Stem cell" as used herein refers to a cell that has the ability to replicate through numerous population doublings (e.g., at least 10-20, or 25-50, or 60-80 doublings), in some cases essentially indefinitely, and to differentiate into multiple cell types or lineages, including at least one of osteogenic, adipogenic, myogenic, neurogenic, hematopoietic, and endothelial cells. Stem cells include, but are not limited to, embryonic stem cells, amniotic fluid stem cells, and multipotent stem cells.

Embryonic stem (ES) cells as used herein refers to cells that are isolated from the inner cell mass of the blastocyst of an embryo and have the potential to develop into any type of cell (i.e., they are "totipotent"). Embryonic stem cells useful for carrying out the present invention are known and described in, for example, U.S. Pat. No. 6,200,806 to Thomson and U.S. Pat. No. 5,843,780 to Thomson.

Amniotic fluid stem cells (AFSC) useful for carrying out the present invention are known and described in, for example, U.S. Patent Application Publication 2005/0124003 to Atala and DeCoppi. AFSC are "pluripotent," i.e., they can differentiate upon appropriate stimulation into osteogenic, adipogenic, myogenic, neurogenic, hematopoietic, and endothelial cells. Appropriate stimulation, for example, may be as follows: Osteogenic induction: The cKit$^+$ cells were cultured in DMEN low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.); Adipogenic induction: To promote adipogenic differentiation, we cultured c-Kit$^+$, seeded at density of 3000 cells/cm$^2$ in DMEN low glucose medium with 10% FBS supplemented with 1 µM dexamethasone, 1 mM 3-isobutyl-1-methylxantine, 10 µg/ml insulin and 60 µM indomethacin (all from Sigma-Aldrich); Myogenic induction: c-Kit$^+$ cells were plated into Matrigel-precoated dish (1 mg/ml, Collaborative Biomedical Products) and cultured in myogenic medium (DMEM low glucose supplemented with 10% horse serum, and 0.5% chick embryo extract from Gibco) followed by treatment of 5-azacytidine (10 µM, Sigma) added in myogenic medium for 24 h; Endothelial induction: c-Kit$^+$ cells were plated into gelatin-precoated dish and cultured in endothelial basal medium-2 (EBM-2, Clonetics BioWittaker) supplemented with 10% FBS and 1% glutamine (Gibco). In preferred embodiments, no feeder layer or leukaemia inhibitory factor (LIF) are required either for expansion or maintenance of AFSCs in the entire culture process.

"Multipotent stem cell" as used herein refers to a cell that has the capacity to grow into any of a subset of the corresponding animal cell types. Unlike a pluripotent cell, a multipotent cell does not have the capacity to form all of the cell types of the corresponding animal. Multipotent stem cells include, but are not limited to, hematopoietic stem cells, neural stem cells, mesenchymal stem cells (e.g., from adipose tissue, bone marrow, etc.), etc.

Proteins (such as growth factors) or other additives (such as antibiotics, anti-inflammatories, and modulators of the immune response) may also be added to the cell and/or keratin preparations at any time. Also, various treatments may be applied to enhance adherence of cells to the substrate and/or to each other. Appropriate treatments are described, for example, in U.S. Pat. No. 5,613,982. For example, collagen, elastin, fibronectin, laminin, or proteoglycans may be applied to the keratin substrates or microcarriers. The substrate or microcarrier can be impregnated with growth factors such as nerve growth factor (NGF), aFGF, bFGF, PDGF, TGFβ, VEGF, GDF-5/6/7, BMP-1/2/3/4/5/6/7/13/12/14, IGF-1, etc., or these agents may be provided in the liquid carrier (e.g., the culture medium).

Cells may be "attachment-dependent" (proliferating only after adhesion to a suitable culture surface or substrate), "attachment-independent" (able to proliferate without the need to attach to a surface or substrate), or contain both types, and growth parameters may be adapted accordingly. For example, some animal cell types, such as lymphocytes, can grow in suspension, while others, including fibroblasts and epithelial and endothelial cells, are attachment-dependent and must attach to a surface and spread out in order to grow. Other cells can grow either in suspension or attached to a surface.

Cells also include cell strains or cell lines, as known in the art, which are typically derived from cells found naturally in tissues. Cell lines differ from cell strains in that they have exceeded the Hayflick's limit and have become immortalized. Cell lines include, but are not limited to, cell lines of the cell types listed above, e.g., the liver cell line HepG, cancer cell lines such as prostate cancer cell lines, breast cancer cells lines, cervical cancer cell lines (e.g., HeLa cells), mouse 3T3 cells, etc.

In some embodiments, cells are provided in or further include a liquid carrier. The liquid carrier can be in the form of a suspension, solution, or any other suitable form, and may or may not include a keratin derivative as described herein. Examples of suitable liquid carriers include, but are not limited to, water, aqueous solutions (e.g., phosphate buffer solution, citrate buffer solution, etc.), liquid media (e.g., modified Eagle's medium ("MEM"), Hanks' Balanced Salts, etc.), gels (e.g., hydrogels), and so forth, and in some embodiments may also include additional ingredients as desired.

As used herein, "growth factors" include molecules that promote the regeneration, growth and survival of cells or tissue. Growth factors that are used in some embodiments of the present invention may be those naturally found in keratin extracts, or may be in the form of an additive, added to the keratin extracts or formed keratin substrates or microcarriers. Examples of growth factors include, but are not limited to, nerve growth factor (NGF) and other neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), and granulocyte-macrophage colony stimulating factor (GM-CSF). There are many structurally and evolutionarily related proteins that make up large families of growth factors, and there are numerous growth factor families, e.g., the neurotrophins (NGF, BDNF, and NT3). The neurotrophins are a family of molecules that promote the growth and survival of, inter glia, nervous tissue. Examples of neurotrophins include, but are not limited to, nerve growth factor (NGF), brain-derived neurotrophic factor (BDNF), neurotrophin 3 (NT-3), and neurotrophin 4 (NT-4). See U.S. Pat. No. 5,843,914 to Johnson, Jr. et al.; U.S. Pat. No. 5,488,099 to Persson et al.; U.S. Pat. No. 5,438,121 to Barde et al.; U.S. Pat. No. 5,235,043 to Collins et al.; and U.S. Pat. No. 6,005,081 to Burton et al.

"Substrates" include porous, particulate, and non-porous (i.e., smooth) surfaces. Substrates may be a synthetic or natural material, and include living and non-living substrates. In some embodiments, a "substrate" includes, but is not limited to, a keratin composition (e.g., a microcarrier comprising, consisting of or consisting essentially of a keratin). In other embodiments, a substrate (e.g., glass, plastic such as polystyrene, etc.) may be coated with a keratin composition. As appreciated by those of skill in the art, certain cell types may grown more readily on a substrate having a certain range of pore size and/or porosity, media and/or supplements, pH, etc.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects also include animal subjects, particularly mammalian subjects such as canines, felines, bovines, caprines, equines, ovines, porcines, rodents (e.g., rats and mice), lagomorphs, non-human primates, etc., for, e.g., veterinary medicine, laboratory research and/or pharmaceutical drug development purposes.

In some embodiments, methods of treatment are provided by administering a substrate (e.g., a keratin microcarrier) that further comprises cells. "Treat" refers to any type of treatment that imparts a benefit to a patient, e.g., a patient afflicted with or at risk for developing a disease (e.g., kidney disease). Treating includes actions taken and actions refrained from being taken for the purpose of improving the condition of the patient (e.g., the relief of one or more symptoms), delay in the onset or progression of the disease, etc.

Cells may be syngeneic (i.e., genetically identical or closely related, so as to minimize tissue transplant rejection), allogeneic (i.e., from a non-genetically identical member of the same species) or xenogeneic (i.e., from a member of a different species) with respect to a subject. Syngeneic cells include those that are autogeneic (i.e., from the patient to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

is referred to as the "gamma" keratins and are considered to aid in crosslinking the cortical proteins. These gamma keratins have a molecular weight of approximately 13 kDa and an average cysteine content of 8.7 mole %. Importantly, alpha and gamma proteins can be further sub-fractionated into acidic and basic fractions. Interestingly, peptide binding domains are concentrated in the alpha fraction, in particular the acidic alpha fraction. This group of proteins is relatively simple to isolate by precipitation and chromatographic methods in order to enhance cell attachment. FIG. 1 and Table 1 show the general distribution of peptide binding motifs on the known human hair keratins. These binding sites are likely present on the surface of keratin biomaterials, as demonstrated by the finding of excellent cell adhesion onto processed keratin foams (see Tachibana A et al., J Biotech 2002; 93:165-70; Tachibana A et al., Biomaterials 2005; 26(3):297-302).

TABLE 1

Properties of Keratin Fractions

| Keratin Type | No. of Published Types | Calculated MW (KDa) | Binding Motifs (% of all published) | Mole % Cysteine | Calculated pI |
|---|---|---|---|---|---|
| Acidic Alpha | 35 | 48.8 ± 2.79 | 100% | 5.31 ± 1.27 | 4.83 ± 0.21 |
| Basic Alpha | 20 | 56.7 ± 4.31 | 35.0% | 4.57 ± 1.85 | 6.29 ± 0.92 |
| Acidic Gamma | 3 | 16.3 ± 8.82 | 66.7% | 9.87 ± 2.66 | 5.32 ± 0.88 |
| Basic Gamma | 4 | 10.5 ± 2.72 | 0% | 7.52 ± 3.22 | 6.82 ± 2.39 |

II. Preparation of Keratin Solutions and Substrates.

Extracted keratin solutions are known to spontaneously self-assemble at the micron scale (see, e.g., Thomas et al., Int J Biol Macromol 1986; 8:258-64; van de Löcht, Melliand Textilberichte 1987; 10:780-6). Self-assembly results in a highly regular structure with reproducible architectures, dimensionality, and porosity. When the keratin is processed correctly, this ability to self-assemble can be preserved and used to create regular architectures on a size scale conducive to cellular infiltration and/or attachment. When keratins are hydrolyzed (e.g., with acids or bases), their molecular weight is reduced, and they lose the ability to self-assemble. Therefore, in some embodiments processing conditions that minimize hydrolysis are preferred.

Cellular recognition is an important characteristic of biomaterials that seek to mimic the extracellular matrix (ECM). Such recognition is facilitated by the binding of cell surface integrins to specific amino acid motifs presented by the constituent ECM proteins. Predominant proteins include collagen and fibronectin, both of which have been extensively studied with regard to cell binding. Both proteins contain several regions that support attachment by a wide variety of cell types. It has been shown that in addition to the widely know Arginine-Glycine-Aspartic Acid (RGD) motif, the "X"-Aspartic Acid-"Y" motif on fibronectin is also recognized by the integrin $\alpha 4\beta 1$, where X equals Glycine, Leucine, or Glutamic Acid, and Y equals Serine or Valine.

Keratins derived from human hair also contain these binding motifs. A search of the NCBI protein database revealed sequences for 62 discrete, unique human hair keratin proteins. Of these, 55 are from the high molecular weight, low sulfur, alpha-helical family, and 7 are from the low molecular weight, high sulfur, globular family. The high molecular weight group of proteins is often referred to as the "alpha" keratins and is responsible for imparting toughness to human hair fibers. These alpha keratins have molecular weights greater than 50 kDa and an average cysteine (the main amino acid responsible for inter- and intramolecular protein bonding) content of 4.9 mole percent. The latter group of proteins Other examples of natural polymers that may be utilized in a similar fashion to the disclosed keratin preparations include, but are not limited to, collagen, gelatin, fibronectin, vitronectin, laminin, fibrin, mucin, elastin, nidogen (entactin), proteoglycans, etc. (See, e.g., U.S. Pat. No. 5,691,203 to Katsuen et al.).

Growth factors are known to be present in developing hair follicles (Jones C M et al., Development 1991; 111:531-42; Lyons K M et al., Development 1990; 109:833-44; Blessings M et al., Genes and Develop 1993; 7:204-15). In fact, more than 30 growth factors and cytokines are involved in the growth of a cycling hair follicle (Hardy M H, Trends Genet 1992; 8(2):55-61; Stenn K S et al., J Dermato Sci 1994; 7S:S109-24; Rogers G E, Int J Dev Biol 2004; 48(2-3):163-70). Many of these molecules have a pivotal role in the regeneration of a variety of tissues and stimulation of numerous cell types. It is highly probable that a number of growth factors become entrained within human hair when cytokines bind to stem cells residing in the bulge region of the hair follicle (Panteleyev A A et al., J Cell Sci 2001; 114:3419-31). Without wishing to be bound to any particular theory, it is thought that these growth factors are extracted along with the keratins from end-cut human hair. This is consistent with previous reports that many different types of growth factors are present in the extracts of various tissues, and that their activity is maintained even after chemical extraction. Observations such as these show mounting evidence that a number of growth factors may be present in end-cut human hair, and that the keratins may be acting as a highly effective delivery matrix of, inter alia, these growth factors.

Keratins can be extracted from human hair fibers by oxidation or reduction using known methods (see, e.g., Crewther W G et al. The chemistry of keratins, in Advances in protein chemistry 1965; 20:191-346). These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Preferred methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines" (See Scheme 1).

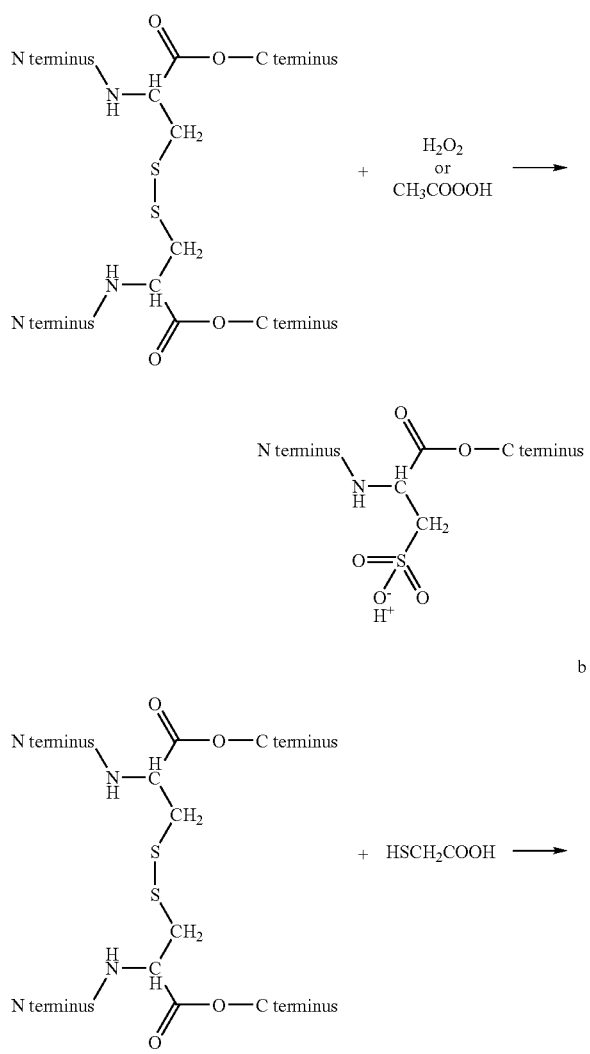

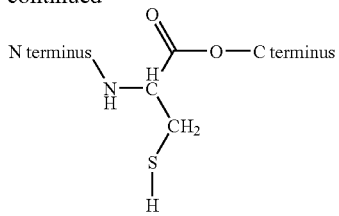

General representations of (a) oxidation and (b) reduction of disulfide crosslinks in keratin. These reactions cleave the sulfur-sulfur bond in cystine residues, thereby destroying the superstructure and rendering the keratins soluble in the reaction media. The resultant fractions are keratose (a) and kerateine (b).

Crude extracts of keratins, regardless of redox state, can be further refined into "gamma" and "alpha" fractions, e.g., by isoelectric precipitation. High molecular weight keratins, or "alpha keratins," (alpha helical), are thought to originate from the microfibrillar regions of the hair follicle, and typically range in molecular weight from about 40-85 kiloDaltons. Low molecular weight keratins, or "gamma keratins," (globular), are thought to originate from the matrix regions of the hair follicle, and typically range in molecular weight from about 10-15 kiloDaltons. (See Crewther W G et al. The chemistry of keratins, in Advances in Protein Chemistry 1965; 20:191-346.)

For example, in some embodiments, the keratin derivative comprises, consists of or consists essentially of unfractionated alpha+gamma keratose. In some embodiments, the keratin derivative comprises, consists of or consists essentially of acidic alpha+gamma kerateines. In some embodiments, the keratin derivative comprises, consists of or consists essentially of basic alpha+gamma keratose.

In some embodiments, the keratin derivative comprises, consists of or consists essentially of unfractionated alpha+gamma kerateines. In some embodiments, the keratin derivative comprises, consists of or consists essentially of acidic alpha+gamma kerateines. In some embodiments, the keratin derivative comprises, consists of or consists essentially of basic alpha+gamma kerateines.

Even though alpha and gamma keratins possess unique properties, the properties of subfamilies of both alpha and gamma keratins can only be revealed through more sophisticated means of purification and separation. Additional properties that are beneficial to cell culture and cell delivery emerge and can be optimized upon further separation and purification of crude keratin extracts. Many protein purification techniques are known in the art, and range from the most simplistic, such as fractional precipitation, to the more complex, such as immunoaffinity chromatography. For extensive treatment of this subject, see Scopes R K (editor) Protein Purification: Principles and Practice (3rd ed. Springer, New York 1993); Roe S, Protein Purification Techniques: A Practical Approach (2nd ed. Oxford University Press, New York 2001); Hatti-Kaul R and Mattiasson B, Isomation and Purification of Proteins (Marcel Dekker AG, New York 2003). For example, sub-families of acidic and basic keratin are separable by moving boundary electrophoresis. A preferred method of fractionation is ion exchange chromatography. We have discovered that these fractions possess unique properties, such as their differential effects on blood cell aggregation (see, e.g., U.S. Pat. No. 7,439,012 to Van Dyke).

In some embodiments, the keratin derivative comprises, consists or consists essentially of a particular fraction or subfraction of keratin. The derivative in some embodiments may comprise, consist or consist essentially of at least 80, 90, 95 or 99 percent by weight of said fraction or subfraction (or more).

In some embodiments, the keratin derivative comprises, consists of, or consists essentially of acidic and/or basic, alpha and/or gamma keratose, where the keratose comprises, consists of or consists essentially of at least 80, 90, 95 or 99 percent by weight of acidic and/or basic, alpha and/or gamma keratose (or more).

In some embodiments, the keratin derivative comprises, consists of, or consists essentially of acidic and/or basic, alpha and/or gamma kerateine, where the kerateine comprises, consists of or consists essentially of at least 80, 90, 95 or 99 percent by weight of acidic and/or basic, alpha and/or gamma kerateine (or more). The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose is preferably produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses (e.g., gamma keratose) can be prepared in like manner as described above for basic and acidic alpha keratose.

Basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100 or 200 kiloDaltons. More preferably, the average molecular weight is from 30 or 40 to 90 or 100 kiloDaltons. Optionally, but preferably, the process further includes the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated by those of skill in the art that the composition preferably contains not more than 5, 2, 1, or 0.1 percent by weight of acidic alpha kerateine, or less.

The acidic alpha kerateine is preferably produced by a reciprocal of the foregoing technique; that is, by separating and retaining acidic alpha kerateine from a mixture of acidic and basic alpha kerateine, e.g., by ion exchange chromatography, and optionally the acidic alpha kerateine has an average molecular weight of from 5 or 10 to 100 or 200 kiloDaltons. Optionally, but preferably, the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines (e.g., gamma kerateine) can be prepared in like manner as described above for basic and acidic alpha kerateine. Gamma keratins are typically precipitated in a non-solvent such as ethanol.

Keratin materials are derived from any suitable source, including, but not limited to, wool and human hair. In one embodiment keratin is derived from end-cut human hair, obtained from barbershops and salons. Keratins from wool have also demonstrated good biocompatibility (see Ito et al., *Kobunshi Ronbunshu* 39(4):249-56 (1982)). The hair or wool is typically washed in warm or hot water and mild detergent, dried, and extracted with a nonpolar organic solvent (e.g., hexane, ether, ethanol, acetone, etc.) to remove residual oil prior to use.

Preparation of Keratoses. Keratose fractions are obtained by any suitable technique. In one embodiment they are obtained using the method of Alexander and coworkers (P. Alexander et al., *Biochem. J.* 46, 27-32 (1950)). Basically, the hair is reacted with an aqueous solution of peracetic acid at concentrations of less than ten percent at room temperature for 12 hours. Keratins are removed from the oxidized hair fibers by subsequent extraction with a denaturing solution such as tris base. The extract solution is filtered and the alpha-keratose fraction precipitated by addition of mineral acid to a pH of approximately 4. The alpha-keratose is separated by filtration, washed with additional acid, followed by dehydration with alcohol, and then freeze dried. Increased purity can be achieved by redissolving the keratose in a denaturing solution such as 7M urea, aqueous ammonium hydroxide solution, or 20 mM tris base buffer solution (e.g., Trizma® base), re-precipitating, re-dissolving, dialyzing against deionized water, and re-precipitating at pH 4.

A preferred method for the production of keratoses is by oxidation with hydrogen peroxide, peracetic acid, or performic acid. A most preferred oxidant is peracetic acid. Preferred concentrations range from 1 to 10 weight/volume percent (w/v %), the most preferred being approximately 2 w/v %. Those skilled in the art will recognize that slight modifications to the concentration can be made to effect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. A preferred oxidation temperature is between 0 and 100 degrees Celsius (° C.). A most preferred oxidation temperature is 37° C. A preferred oxidation time is between 0.5 and 24 hours. A most preferred oxidation time is 12 hours. A preferred liquid to solid ratio is from 5 to 100:1. A most preferred ratio is 20:1. After oxidation, the hair is rinsed free of residual oxidant using a copious amount of distilled water.

The keratoses can be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and 2-Amino-2-(hydroxymethyl)-1,3-propanediol (tris base). A preferred solution is Trizma® base in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 2 hours. A preferred liquid to solid ratio is from 5 to 100:1. A most preferred ratio is 40:1. Additional yield can be achieved with subsequent extractions with dilute solutions of tris base or deionized (DI) water. After extraction, the residual solids are removed from solution by centrifugation and/or filtration.

The crude extract can be isolated by first neutralizing the solution to a pH between 7.0 and 7.4. A most preferred pH is 7.4. Residual denaturing agent is removed by dialysis against DI water. Concentration of the dialysis retentate is followed by lyophilization or spray drying, resulting in a dry powder mixture of both gamma- and alpha-keratose. Alternately, alpha-keratose is isolated from the extract solution by dropwise addition of acid until the pH of the solution reaches approximately 4.2. Preferred acids include sulfuric, hydrochloric, and acetic. A most preferred acid is concentrated hydrochloric acid. Precipitation of the alpha fraction begins at around pH 6.0 and continues until approximately 4.2. Fractional precipitation can be utilized to isolate different ranges of protein with different isoelectric properties. Solid alpha-keratose can be recovered by centrifugation or filtration.

The alpha keratose can be further purified by re-dissolving the solids in a denaturing solution. The same denaturing solutions as those utilized for extraction can be used, however a preferred denaturing solution is tris base. Ethylene diamine tetraacetic acid (EDTA) can be added to complex and remove trace metals found in the hair. A preferred denaturing solution is 20 mM tris base with 20 mM EDTA or DI water with 20 mM EDTA. If the presence of trace metals is not detrimental to the intended application, the EDTA can be omitted. The alpha-keratose is re-precipitated from this solution by dropwise addition of hydrochloric acid to a final pH of approximately 4.2. Isolation of the solid is by centrifugation or filtration. This process can be repeated several times to further purify the alpha-keratose, although excessive processing can be detrimental to the proteins.

The gamma keratose fraction remains in solution at pH 4 and is isolated by addition to a water-miscible organic solvent such as alcohol, followed by filtration, dehydrated with additional alcohol, and freeze dried. Increased purity can be achieved by re-dissolving the keratose in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and re-precipitating by addition to alcohol. The amount of alcohol consumed in these steps can be minimized by first concentrating the keratose solution by distillation or ultrafiltration.

After removal of the alpha keratose, the concentration of gamma keratose from a typical extraction solution is approximately 1-2%. The gamma keratose fraction can be isolated by addition to a water-miscible non-solvent. To effect precipitation, the gamma-keratose solution can be concentrated by evaporation of excess water. This solution can be concentrated to approximately 10-20% by removal of 90% of the water. Evaporation can be done using vacuum distillation or by falling film evaporation. After concentration, the gamma-keratose solution is added dropwise to an excess of cold non-solvent. Suitable non-solvents include ethanol, methanol, acetone, and the like. A most preferred non-solvent is ethanol. A most preferred method is to concentrate the gamma keratose solution to approximately 10 w/v % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying. Alternate methods for the isolation of gamma-keratose that do not involve the use of alcohol precipitation include freeze drying and spray drying.

Preparation of Kerateines. Kerateine fractions can be obtained using a combination of the methods of Bradbury and Chapman (J. Bradbury et al., *Aust. J. Biol. Sci.* 17, 960-72 (1964)) and Goddard and Michaelis (D. Goddard et al., *J. Biol. Chem.* 106, 605-14 (1934)). Essentially, the cuticle of the hair fibers is removed ultrasonically in order to avoid excessive hydrolysis and allow efficient reduction of cortical disulfide bonds in a second step. The hair is placed in a solution of dichloroacetic acid and subjected to treatment with an ultrasonic probe. Further refinements of this method indicate that conditions using 80% dichloroacetic acid, solid to liquid of 1:16, and an ultrasonic power of 180 Watts are optimal (Ando et al., (1975) Sen'i Gakkaishi 31(3), T81-85). Solid fragments are removed from solution by filtration, rinsed and air dried, followed by sieving to isolate the hair fibers from removed cuticle cells.

In some embodiments, following ultrasonic removal of the cuticle, alpha and gamma kerateines are obtained by reaction of the denuded fibers with mercaptoethanol. Specifically, a low hydrolysis method is used at acidic pH (Thompson et al., Aust. J. Biol. Sci. 15, 757-68 (1962)). In a typical reaction, hair is extracted for 24 hours with 4M mercaptoethanol that has been adjusted to pH 5 by addition of a small amount of potassium hydroxide in deoxygenated water containing 0.02M acetate buffer and 0.001M surfactant.

The solution is filtered and the alpha kerateine fraction precipitated by addition of mineral acid to a pH of approximately 4. The alpha kerateine is separated by filtration, washed with additional acid, followed by dehydration with alcohol, and then dried under vacuum. Increased purity is achieved by re-dissolving the kerateine in a denaturing solution such as urea solutions between 0.1 and 10M (e.g., 7M urea), aqueous ammonium hydroxide solution, or 20 mM tris buffer solution, re-precipitating, re-dissolving, dialyzing against deionized water, and re-precipitating at pH 4.

The gamma kerateine fraction remains in solution at pH 4 and is isolated by addition to a water-miscible organic solvent such as alcohol, followed by filtration, dehydrated with additional alcohol, and dried under vacuum. Increased purity can be achieved by re-dissolving the kerateine in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratin solution by distillation.

In an alternate method, the kerateine fractions are obtained by reacting the hair with an aqueous solution of sodium thioglycolate. A preferred method for the production of kerateines is by reduction of the hair with thioglycolic acid or beta-mercaptoethanol. A most preferred reductant is thioglycolic acid (TGA). Preferred concentrations range from 0.5M to 10M, the most preferred being approximately 1.0M or 0.5M. Those skilled in the art will recognize that slight modifications to the concentration can be made to effect varying degrees of reduction, with concomitant alterations in pH, reaction time, temperature, and liquid to solid ratio. A preferred pH is from 8 to 12, or from 9 to 11.5, or from 10 to 11. A most preferred pH is 10, 10.2, or 11. The pH of the reduction solution is altered by addition of base. Preferred bases include transition metal hydroxides, sodium hydroxide, and ammonium hydroxide. A most preferred base is sodium hydroxide. The pH adjustment is effected by dropwise addition of a saturated solution of sodium hydroxide in water to the reductant solution. A preferred reduction temperature is between 0 and 100° C. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution is therefore combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of kerateines. The relative solubility rankings in water is gamma-keratose>alpha-keratose>gamma-kerateine>alpha-kerateine from most to least soluble. Consequently, extraction yields from reduced hair fibers are not as high. This being the case, subsequent extractions are conducted with additional reductant plus denaturing agent solutions. Preferred solutions for subsequent extractions include TGA plus urea, TGA plus tris base, or TGA plus sodium hydroxide. After extraction, crude fractions of alpha- and gamma-kerateine can be isolated using the procedures described for keratoses. However, precipitates of gamma- and alpha-kerateine re-form their cystine crosslinks upon exposure to oxygen. Precipitates must therefore be re-dissolved quickly to avoid insolubility during the purification stages, or precipitated in the absence of oxygen.

Residual reductant and denaturing agents can be removed from solution by dialysis. Typical dialysis conditions are 1 to 2% solution of kerateines dialyzed against DI water for 1 to 72 hours. Those skilled in the art will recognize that other methods exist for the removal of low molecular weight contaminants in addition to dialysis (e.g. microfiltration, chromatography, and the like). The use of tris base is only required for initial solubilization of the kerateines. Once dissolved, the kerateines are stable in solution without the denaturing agent and at pH>7. Therefore, the denaturing agent can be removed without the resultant precipitation of kerateines, so long as the pH remains at or above neutrality. The final concentration of kerateines in these purified solutions can be adjusted by the addition/removal of water.

Regardless of the form of the keratin (i.e. keratoses or kerateines), several different approaches to further purification can be employed to keratin solutions. Care must be taken, however, to choose techniques that lend themselves to keratin's unique solubility characteristics. One of the most simple separation technologies is isoelectric precipitation. In this method, proteins of differing isoelectric point can be isolated by adjusting the pH of the solution and removing the precipitated material. In the case of keratins, both gamma- and alpha-forms are soluble at pH >6.0. As the pH falls below 6, however, alpha-keratins begin to precipitate. Keratin fractions can be isolated by stopping the precipitation at a given pH and separating the precipitate by centrifugation and/or filtration. At a pH of approximately 4.2, essentially all of the alpha-keratin will have been precipitated. These separate fractions can be re-dissolved in buffer solution, dialyzed, concentrated, and reduced to powders by lyophilization or spray drying. However, kerateine fractions must be stored in the absence of oxygen or in dilute solution to avoid crosslinking.

Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to effect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 7 and above, both gamma- and alpha-keratins are soluble and the solution pH is above their isoelectric points. As such, they are anionic and can be bound to an anionic exchange resin. However, it has been discovered that a sub-fraction of keratins does not bind to a weakly anionic exchange resin and instead passes through a column packed with such resin. A preferred solution for AIEx chromatography is purified or fractionated keratin, isolated as described previously, in purified water at a concentration between 0 and 5 weight/volume %. A preferred concentration is between 0 and 4 w/v %. A most preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 5 and 7. A most preferred pH is 5.3 for keratoses and 6 for kerateines. This solution can be loaded onto an AIEx column such as DEAE-Sepharose® resin or Q-Sepharose® resin columns. A preferred column resin is DEAE-Sepharose® resin. The solution that passes through the column can be collected and further processed as described previously to isolate a fraction of acidic keratin powder.

As used herein, "acidic" keratins are those keratins that are protonated at a predetermined pH such that they carry a net positive charge; "basic" keratins are those keratins that are de-protonated at a predetermined pH such that they carry a net negative charge. In some embodiments, the predetermined pH is between 5 and 7. In some embodiments, the pH is 6. For example, in some embodiments, keratose or kerateine is separated into acidic and basic fractions (e.g., by ion exchange chromatography) performed at a solution pH of 6, with the resulting acidic fraction including those keratins having a net positive charge at pH 6, and the basic fraction including those keratins having a net negative charge at pH 6. Likewise, for separation at a predetermined pH of 5.3, the acidic fraction will include those keratins having a net positive charge at pH 5.3 and the basic fraction will include those keratins having a net negative charge at pH 5.3.

Those skilled in the art will recognize that the predetermined pH is selected to effect the best separation between acidic and basic proteins based upon their isoelectric points (see, e.g., Table 1), though solubility at that pH should also be considered. When the pH of the solution is between the isoelectric point of these acidic and basic keratin fractions, basic keratin proteins will be de-protonated to have a net negative charge and bind to a cationic media (e.g., DEAE-Sepharose or Q-Sepharose (anion exchange)), while the acidic proteins will be protonated to have a net positive charge and pass through the column, thereby effecting separation.

In some embodiments the activity of the keratin matrix is enhanced by using an AIEx column to produce the keratin that may be useful for, inter alia, promoting cell adhesion. Without wishing to be bound to any particular theory, it is thought that charged substrates promotes cell attachment. Though many cells have a negative surface charge, they attach to surfaces that are negatively as well as positively charged (see, e.g., van der Velden-de Groot "Microcarrier technology, present status and perspective" (1995) Cytotechnology 18:51-56).

Another fraction binds readily, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 8. In order to maintain stable pH during the elution process, a buffer salt can be added. A preferred buffer salt is Trizma® base. Those skilled in the art will recognize that slight modifications to the salt concentration and pH can be made to effect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate fractions of basic keratin powders.

A complimentary procedure is also feasible using CIEx techniques. Namely, the keratin solution can be added to a cation exchange resin such as SP Sepharose® resin (strongly cationic) or CM Sepharose® resin (weakly cationic), and the basic fraction collected with the pass through. The retained acid keratin fraction can be isolated by salting as previously described.

Meta kerateines. Kerateines have labile sulfur residues. During the creation of the kerateines, cystine is converted to cysteine, which can be a source of further chemical modifications. One such useful reaction is oxidative sulfur-sulfur coupling. This reaction simply converts the cysteine back to cystine and reforms the crosslinks between proteins. Crosslinking gamma or alpha kerateine fractions, or a combination of both, produces meta-kerateines. This is a useful reaction to increase the molecular weight of kerateines, which in turn will modify their bulk properties. Increasing molecular weight influences material properties such a viscosity, dry film strength, gel strength, etc. Additionally, water solubility can be modified through the production of meta kerateines. The high crosslink density of meta kerateines renders these biomaterials essentially insoluble in aqueous media, making them amenable to applications where preservation of material integrity in such media is preferred.

Meta keratins can be derived from the gamma or alpha fractions, or a combination of both. Oxidative re-crosslinking of the kerateines is affected by addition of an oxidizing agent such as peracetic acid or hydrogen peroxide to initiate oxidative coupling reactions of cysteine groups. A preferred oxidizing agent is oxygen. This reaction can be accomplished simply by bubbling oxygen through the kerateine solution or by otherwise exposing the sample to air. Optimizing the molecular weight through the use of meta keratins allows formulations to be optimized for a variety of properties including viscosity, film strength and elasticity, fiber strength, and hydrolytic susceptibility. Crosslinking in air works to improve biocompatibility by providing biomaterial with a minimum of foreign ingredients.

Basically, in some embodiments the kerateine is dissolved in a denaturing solution such as 7M urea, aqueous ammonium hydroxide solution, or 20 mM tris buffer solution. The progress of the reaction is monitored by an increase in molecular weight as measured using SDS-PAGE. Oxygen is continually bubbled through the reaction solution until a doubling or tripling of molecular weight is achieved. The pH of the denaturing solution can be adjusted to neutrality to avoid hydrolysis of the proteins by addition of mineral acid.

Optimizing the molecular weight through the use of meta-keratins allows formulations to be optimized for a variety of properties including viscosity, film strength and elasticity, fiber strength, and hydrolytic susceptibility. In some embodiments, crosslinking in air may improve biocompatibility by providing biomaterials with a minimum of foreign ingredients.

Keratin intermediate filaments. IFs of human hair fibers are obtained using the method of Thomas and coworkers (H. Thomas et al., *Int. J. Biol. Macromol.* 8, 258-64 (1986)). This is essentially a chemical etching method that reacts away the keratin matrix that serves to "glue" the IFs in place, thereby leaving the IFs behind. In a typical extraction process, swelling of the cuticle and sulfitolysis of matrix proteins is achieved using $0.2M\ Na_2SO_3$, $0.1M\ Na_2O_6S_4$ in 8M urea and 0.1M Tris-HCl buffer at pH 9. The extraction proceeds at room temperature for 24 hours. After concentrating, the dissolved matrix keratins and IFs are precipitated by addition of zinc acetate solution to a pH of approximately 6. The IFs are then separated from the matrix keratins by dialysis against 0.05M tetraborate solution. Increased purity is obtained by precipitating the dialyzed solution with zinc acetate, redissolving the IFs in sodium citrate, dialyzing against distilled water, and then freeze drying the sample.

Further discussion of keratin preparations are found in U.S. Patent Application Publication 2009/0004242 (Van Dyke), which is incorporated by reference herein.

Formulations. Dry powders may be formed of keratin preparations as described above in accordance with known techniques such as freeze drying (lyophilization). In some embodiments, compositions of the invention may be produced by mixing such a dry powder composition form with an aqueous solution to produce a composition having an electrolyte solution with a keratin solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution is contained in the dry powder.

The formation of a substrate or microcarrier including keratin materials such as described above can be carried out in accordance with techniques long established in the field or variations thereof that will be apparent to those skilled in the art. In some embodiments, the keratin preparation is dried and rehydrated prior to use. See, e.g., U.S. Pat. No. 2,413,983 to Lustig et al., U.S. Pat. No. 2,236,921 to Schollkipf et al., and U.S. Pat. No. 3,464,825 to Anker. In some embodiments, lyophilized material is rehydrated with a suitable solvent, such as water or phosphate buffered saline (PBS). The material can be sterilized, e.g., by γ-irradiation (800 krad) using a ⁶⁰Co source. Other suitable methods of forming keratin matrices include, but are not limited to, those found in U.S. Pat. No. 6,270,793 (Van Dyke et al.), U.S. Pat. No. 6,274,155 (Van Dyke et al.), U.S. Pat. No. 6,316,598 (Van Dyke et al.), U.S. Pat. No. 6,461,628 (Blanchard et al.), U.S. Pat. No. 6,544,548 (Siller-Jackson et al.), and U.S. Pat. No. 7,01,987 (Van Dyke).

In some composition embodiments, the keratin preparations (particularly alpha and/or gamma kerateine and alpha and/or gamma keratose) have an average molecular weight of from about 10 to 70 or 85 or 100 kiloDaltons. Other keratin derivatives, particularly meta-keratins, may have higher average molecular weights, e.g., up to 200 or 300 kiloDaltons.

The keratin derivative composition or formulation may optionally contain one or more active ingredients such as one or more growth factors (e.g., in an amount ranging from 0.000000001, 0.000000005, or 0.00000001, to 0.00000001, 0.00000005, or 0.0000001 percent by weight of the composition that comprises the keratin) to facilitate cell or tissue adhesion and/or proliferation, etc. Examples of suitable active ingredients include, but are not limited to, nerve growth factor, vascular endothelial growth factor, fibronectin, fibrin, laminin, acidic and basic fibroblast growth factors, testosterone, ganglioside GM-1, catalase, insulin-like growth factor-I (IGF-I), platelet-derived growth factor (PDGF), neuronal growth factor galectin-1, and combinations thereof. See, e.g., U.S. Pat. No. 6,506,727 to Hansson et al. and U.S. Pat. No. 6,890,531 to Horie et al.

For example, nerve growth factor (NGF) can be added to the keratin composition in an amount effective to promote the regeneration, growth and survival of various tissues. The NGF is provided in concentrations ranging from 0.1 ng/mL to 1000 ng/mL. More preferably, NGF is provided in concentrations ranging from 1 ng/mL to 100 ng/mL, and most preferably 10 ng/mL to 100 ng/mL. See U.S. Pat. No. 6,063,757 to Urso.

The compositions, substrates and/or microcarriers are preferably sterile. In some embodiments, microcarrier precursor solutions are sterile filtered and processed aseptically, or terminally sterilized using ethylene oxide, e-beam, gamma, or other low temperature method (i.e. <50° C.).

The composition may be provided preformed and aseptically packaged in a suitable container, such as a flexible polymeric bag or bottle, or a foil container, or may be provided as a kit of sterile dry powder in one container and sterile aqueous solution in a separate container for mixing just prior to use. When provided pre-formed and packaged in a sterile container the composition preferably has a shelf life of at least 4 or 6 months (up to 2 or 3 years or more) at room temperature, prior to substantial loss of viscosity (e.g., more than 10 or 20 percent) and/or structural integrity of the keratin substrate or microcarrier.

The composition may be provided in a precursor solution aseptically packaged in a suitable container. For example, a coating or gel precursor solution can be provided in a glass ampule ready to use directly or after dilution by the user. In the case of kerateine compositions, which can re-crosslink in the presence of oxygen in air, a sterile precursor solution in a sealed ampule under an inert atmosphere (e.g. nitrogen) can be provided. A user would simple break open the ampule and use the solution directly or after dilution for producing coatings or gels in cultureware.

Applications for the cell culture substrates and microcarriers include, but are not limited to, culturing bacteria, yeast, insect cells and animal (e.g., human) cells, e.g., for production of cells for therapy, vaccines and vectors, natural and recombinant proteins, antibodies, expansion and differentiation of stem cells, etc.

Microcarrier preparations. Kerateine (e.g., alpha, gamma or meta) solutions can be formed into microcarriers using a variety of techniques. Particles of kerateine can be produced in a variety of sizes and shapes, with varying degrees of porosity, hardness, surface chemistry, size and shape by changing the relative amounts of alpha and gamma fractions. Microparticle production techniques include spray drying, emulsion polymerization, and lyophilization followed by grinding. Specific sizes of microcarriers can be obtained by a number of sorting techniques known in the art such as sieving.

"Microcarriers" are small, discrete particles employed to expand two-dimensional cell culture to three dimensions. See, e.g., U.S. Pat. No. 3,717,551 to Bizzini et al., U.S. Pat. No. 4,036,693 to Levine et al., U.S. Pat. No. 4,153,510 to Messing et al., U.S. Pat. No. 4,189,534 to Levine et al., U.S. Pat. No. 4,237,033 to Scattergood, U.S. Pat. No. 4,266,032 to Miller et al., U.S. Pat. No. 4,293,654 to Levine et al., U.S. Pat. No. 4,335,215 to Tolbert et al., U.S. Pat. No. 4,824,946 to Schwengers et al., U.S. Pat. No. 5,006,467 to Kusano et al., and U.S. Pat. No. 5,512,474 to Clapper et al. Microcarriers provide high surface area and can be utilized in stirred bioreactors, fluidized beds, packed columns, etc., to support high cell densities in liquid media.

Microcarriers can be ionic or non-ionic. Examples of ionic microcarriers include, but are not limited to, DEAE-Sephadex A50, low charge Sephadex, DEAE-cellulose, DEAE-cellulose fibers, polyacrylamide, polystyrene, derivatized polyacrylein microspheres in agarose, glass, glass-coated plastics, etc. Examples of non-ionic microcarriers include, but are not limited to, dextran beads with denatured collagen, gelatin (e.g., crosslinked with gluttaraldehyde, macroporous gelatin microcarriers, etc.), cellulose, polystyrene coated with collagen, polyethylene, polystyrol, polyurethane binder (e.g., with fibronectine factors), polyester fiber with collagen, etc. Ionic materials are generally used to manufacture smooth microcarriers, while non-ionic materials are generally used for macroporous carriers (see van der Velden-de Groot, Cytotechnology (1995) 18:51-56). For cells growing in suspension (e.g., attachment-independent), cells may be encapsulated in a microporous gel (e.g., agarose, gelatin, etc.).

In some embodiments, the keratin substrates or microcarriers have a pore size and/or porosity that is ideal for the infiltration and attachment of cells of interest (e.g., attachment-dependent cells). "Pore size" refers to the two-dimensional measurement of empty or void space present in the substrate, while porosity refers to the three-dimensional measurement of empty space or void volume per total volume. As a general guide, eukaryotic animal cells and plant cells are typically from 10 to 100 μm, and prokaryotic cells are typically from 0.1 to 10 μm in diameter. Upon enzymatic treatment (e.g., trypsinization), the cells typically to shrink to smaller spheres. As a general guide, after enzymatic treatment animal cells are typically from several micrometers to 30 micrometers.

In some embodiments, average pore sizes are large enough to accommodate an intact cell. For example, in some embodiments the resulting pore sizes are greater than 1 micron, and more preferably greater than 50 microns. In other embodiments, the pore size may be 100 microns or more. In some embodiments, the average pore size of keratin substrates or microcarriers developed using the processes described herein on bone tissue is from 400-1000 microns. In some embodiments, the ideal pore size of ligament, tendon, and meniscus tissues is from 100-1000 microns. In some embodiments, the average pore size is approximately 1.5 to 3 times the cell diameter of the cells of interest. In some embodiments, the average pore size is approximately three times a cell diameter of 1 to 30, 40, or 50 or more microns (i.e., 3 to 90, 120, or 150 or more microns).

In other embodiments, average pore sizes are not large enough to accommodate intact cells, and cells can attach only to the surface of the substrate. For example, the average pore size in some embodiments is less than 100, 70, 50, 20, 10, 1.0, or 0.5 microns.

In some embodiments, bulk porosity (void fraction) ranges from 50 to 99%. A preferred porosity is greater than 80%. A most preferred porosity is greater than 90%.

In some embodiments, keratin substrates or microcarriers are not water soluble. In other embodiments, they are "biostable," meaning they are not broken down by typical cell secreted enzymes (e.g., matrix metalloproteases), making them suitable as substrates for long-term microcarrier cell cultures (e.g., from 3 or 6 months to a year or more).

In addition to microcarriers formed from kerateine, microcarriers may be formed from ionic or non-ionic microcarriers (e.g., as listed above) and coated with keratin. Alternatively, microcarriers may be formed from kerateine and coated with, e.g., collagen, gelatin, amino acids, etc.

In some embodiments, microcarriers have an average diameter greater than 10 μm are preferred, and those between 10 μm and 500 μm are most preferred (measured by, e.g., scanning electronic microscopy, light scattering techniques, etc.). In some embodiments, microcarriers have a relative density such that they can be maintained in suspension in a desired liquid (e.g., water, media, etc.) with gentle stirring, e.g., suspendable without shear that would harm or alter the cells.

Smaller sizes can be obtained using spray drying (e.g., 10-50 μm), while larger sizes can be produced using emulsion polymerization or grinding/sorting. Smaller particles are more easily suspended in media because they have a slower sedimentation rate, making them better suited for stirred bioreactor applications. Larger particles have higher sedimentation rates and are better suited for fluidized bed and packed column applications. In some embodiments, crosslinked kerateines are not water soluble, nor can they be broken down by typical cell secreted enzymes (e.g., matrix metalloproteases), making them suitable as substrates for long-term microcarrier cell cultures.

In some embodiments, physical properties of the keratin microcarriers are controlled by composition (e.g., alpha:gamma keratin ratio) and/or processing (e.g., spray drying, emulsion) techniques. Physical properties include, but are not limited to, pore size, porosity, hardness, size and shape of the microcarriers.

In some embodiments, biological properties (e.g., cell attachment) are controlled by composition and/or processing techniques. For example, microcarriers made with kerateine particles provide a surrogate extracellular matrix environment. Keratins possess many peptide binding motifs that are specific to the integrin receptors found on many cell types. Unlike conventional microcarriers, in some embodiments kerateines contain numerous regulatory molecules that are essential for cell function. As such they are useful to grow cells in high density. Applications include, but are not limited to, production of cells for therapy, vaccines and vectors, natural and recombinant proteins, antibodies, and expansion and differentiation of stem cells.

In further embodiments, the microcarriers may be weighted to achieve the desired specific gravity (see U.S. Pat. No. 4,861,714 to Dean, Jr. et al.). In other embodiments, keratin substrates or microcarriers are modified to produce the desired charge capacity (see U.S. Pat. Nos. 4,293,654 and 4,189,534 to Levine et al.).

Methods of treatment. Because keratins are biocompatible, in some embodiments colonized microcarriers can be used directly for therapy such as an injectable (e.g., for cardiac regeneration) or as a surface treatment (e.g., for skin wounds). Keratin substrates or microcarriers may be administered to a subject in need thereof, with or without prior seeding or attachment of cultured cells. Formulations of the invention include those for parenteral administration (e.g., subcutaneous, intramuscular, intradermal, intravenous, intra-arterial, intraperitoneal injection) or implantation. In one embodiment, administration is carried out intravascularly, either by simple injection, or by injection through a catheter positioned in a suitable blood vessel, such as a renal artery. In some embodiments, administration of keratin substrates or microcarriers is carried out by "infusion," whereby compositions are introduced into the body through a vein (e.g., the portal vein). In another embodiment, administration is carried out as a graft to an organ or tissue to be augmented as discussed above, e.g., kidney and/or liver.

Substrates or microcarriers may also be delivered systemically. In further embodiments, cells are delivered to certain tissues (e.g., the liver), but the outcome of the functional effects of the delivery will be systemic (e.g., microcarriers seeded with cells producing hormones). See, e.g., the "Edmonton protocol," an established delivery method, where cells are infused into a patient's portal vein (Shapiro et al. (2000) N Engl J Med 343:230-238).

According to some embodiments, the cells administered to the subject may be syngeneic (i.e., genetically identical or closely related, so as to minimize tissue transplant rejection), allogeneic (i.e., from a non-genetically identical member of the same species) or xenogeneic (i.e., from a member of a different species), as above, with respect to the subject being treated, depending upon other steps such as the presence or absence of encapsulation or the administration of immune suppression therapy of the cells. Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. As an example of a method that can be used to obtain cells from a donor (e.g., a potential recipient of a bioscaffold graft), standard biopsy techniques known in the art may be employed. Alternatively, cells may be harvested from the subject, expanded/selected in vitro, and reintroduced into the same subject (i.e., autogeneic).

In some embodiments, cells are administered in a therapeutically effective amount. The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments a dosage of between $1\text{-}100\times10^8$ cells per kilogram subject body weight can be given, administered together at a single time or given as several subdivided administration. Of course, follow-up administrations may be given if necessary.

In further embodiments, if desired or necessary, the subject may be administered an agent for inhibiting transplant rejection of the administered cells, such as rapamycin, azathioprine, corticosteroids, cyclosporin and/or FK506, in accordance with known techniques. See, e.g., R. Caine, U.S. Pat. Nos. 5,461,058, 5,403,833 and 5,100,899; see also U.S. Pat. Nos. 6,455,518, 6,346,243 and 5,321,043. Some embodiments use a combination of implantation and immunosuppression, which minimizes rejection.

Kits are also provided, where the microcarriers described herein are provided in a suitable container (e.g. a plastic or glass bottle, sterile ampule, etc.), optionally packaged in sterile form. The microcarriers may be provided as a powder, or in an aqueous liquid, and may be provided in different volumes for specific cell densities. For example, microcarriers in some embodiments are packaged in alcohol (e.g., ethanol, propanol, etc.) for long-term sterility.

Keratin coatings and additives. In addition, any suitable substrate (e.g., cultureware such as petri dishes, 2-6-, 12-, 24-, 96-, or 384-well plates, etc.) may be coated or treated with keratin materials or keratin derivatives as described herein to promote the adhesion, proliferation and/or function of cells for cell culture.

The substrate may be formed from any suitable material, including, but not limited to, organic polymers (including stable polymers and biodegradable or bioerodable polymers), natural materials (e.g., collagen), metals (e.g., platinum, gold, stainless steel, etc.) inorganic materials such as plastic, silicon, glass, etc., and composites thereof, e.g., styrene, polypropylene, polystyrene, etc.

Coating of the substrate may be carried out by any suitable means, such as spray coating, dip coating, or the like. In some embodiments, steps may be taken to couple or covalently couple the keratin to the substrate such as with a silane coupling agent, if so desired. The keratin derivative may be subsequently coated with another material, and/or other materials may be co-deposited with the keratin derivative, such as one or more additional active agents, stabilizers, coatings, etc.

Keratin derivatives taught herein that are useful as coatings for cell culture include, but are not limited to: α+γ-keratose, α-keratose, γ-keratose, basic α-keratose, acidic α-keratose, basic γ-keratose, acidic γ-keratose, α+γ-kerateine, α-kerateine, γ-kerateine, basic α-kerateine, acidic α-kerateine, basic γ-kerateine, acidic γ-kerateine, and combinations thereof. Composition of the keratin coatings may be optimized according to cell type, e.g., using the assays described hereinbelow or assays generally known to those of skill in the art.

Some keratins as taught herein may also be used in gel form for three-dimensional cell culture, similar to products such as collagen gels or Matrigel™. Keratoses are water soluble, and in some embodiments may not be suitable for long-term culture, but keratose gels according to some embodiments can be used for short-term culture (e.g., less than 14, 20, or 30 days). Suitable keratose gels may be formed from the powdered precursors described above by, e.g., addition of a balanced salt solution. A preferred keratose concentration in the gel is between 5 and 30 percent, or between 15 and 25 percent.

Kerateines are, likewise, suitable for three-dimensional cell culture as they, too, form gels. These gels can be re-crosslinked so that they are not water soluble, which may render them suitable for both short- and long-term culture. Suitable kerateine gels are formed from precursor solutions by removing excess water to achieve the desired protein concentration. Preferred concentration of kerateine in the gel is between 5 and 30 percent, or between 10 and 20 percent.

Both keratose and kerateine gels can be formed from acid or basic alpha-keratin, or combinations thereof, with and without the addition of gamma-keratins (whether acidic or basic) or combinations thereof. These gels may also be freeze dried to provide a dry product or scaffold that can be used in a similar fashion as the gels by addition or "seeding" with a suitable cell suspension.

These keratin derivatives may also be used as an additive to media or other liquid carrier of the cells to promote growth and proliferation. "Media" as used herein refers to a composition (e.g., liquid, gel, etc.) that is capable of supporting the growth and proliferation of cells, as is known in the art. Examples include, but are not limited to, "basic" media such as Basal Salts, MEM, DMEM, Medium 199, etc. See, e.g., PCT Publication No. WO 2007/002762. Basic media may typically include amino acids (e.g., essential, nonessential, etc.), vitamins (e.g., water soluble, fat soluble), salts (e.g., $Na^+$, $K^+$, $Mg^{++}$, $Cl^-$, $SO_4^{2-}$, $PO_4^{3-}$, etc.), trace metals (e.g., $Cu^{2+}$, $Fe^{3+}$, $Zn^{2+}$, etc.), nucleosides, energy metabolism source (e.g., flusoe, pyruvate, etc.), and/or lipids/precursors. Media may or may not include serum (basic media with serum added is called "complete" media), and in some embodiments serum-free media is preferred.

The present invention is explained in greater detail in the following non-limiting Examples. As disclosed herein, these fractions of keratin have demonstrated remarkable cell contacting properties, and promote cell binding, growth, and functionality. Using the different fractions of keratoses and kerateines purified as described herein, or combinations thereof, substrates for cell growth can be fabricated and optimized for a particular cell of interest.

Example 1

Crude Kerateine Samples

Kerateine fractions were obtained using a modification of the method described by Goddard and Michaelis. Briefly, the hair was reacted with an aqueous solution of 1M TGA at 37° C. for 24 hours. The pH of the TGA solution had been adjusted to pH 11 by dropwise addition of saturated NaOH solution. The extract solution was filtered to remove the reduced hair fibers and retained. Additional keratin was extracted from the fibers by sequential extractions with 2000 mL of 100 mM TGA for 2 hours, followed by 2000 mL of deionized (DI) water for 2 hours, both at 37° C. After each extraction, the solution was centrifuged and filtered. This entire process (i.e. reduction, tris extraction, DI water extraction) was repeated one additional time, although the extraction solution volumes were reduced by half. Eventually, all the extracts were combined and the alpha-kerateine fraction separated by isolectric precipitation using the same method as that described below for keratose. However, after dialysis of the fractions, they were titrated to pH 8.0 and stored at 4° C.

Eventually, all the extracts were combined and dialyzed against DI water with a 1 KDa nominal low molecular weight cutoff membrane. The solution was concentrated, titrated to pH 7, and stored at approximately 5% total protein concentration at 4° C. Alternately, the concentrated solution could be lyophilized and stored frozen and under nitrogen.

Example 2

Ion Exchange Chromatography of Kerateine

Kerateines have a propensity to crosslink in air, so oxygen free processing is used. Just prior to fractionation, kerateine samples are titrated to pH 6 by careful addition of dilute HCl solution. The samples are loaded onto a 200 mL flash chromatography column containing either DEAE-Sepharose®

(weakly anionic) or Q-Sepharose® (strongly anionic) exchange resin (50-100 mesh; Sigma-Aldrich, Milwaukee, Wis.) with gentle pressure and the flow through collected (acidic keratin). A small volume of 10 mM Trizma® base (approximately 200 mL) at pH 6 is used to completely wash through the sample. Basic kerateine is eluted from the column with 100 mM tris base plus 2M NaCl at pH 12. Each sample is separately neutralized and dialyzed against DI water using tangential flow dialysis with a LMWCO of 1 KDa, concentrated by rotary evaporation, and freeze dried.

Example 3

Cell Culture with Kerateine-Coated Tissue Culture Dishes

To test the feasibility of using keratin protein as coating material for functional cell growth, polystyrene tissue culture dishes were coated using a keratin solution of unfractionated alpha+gamma kerateine (100 µg/ml), and compared to dished coated with collagen (100 µg/ml) and a non-coated dish.

Figure 3:
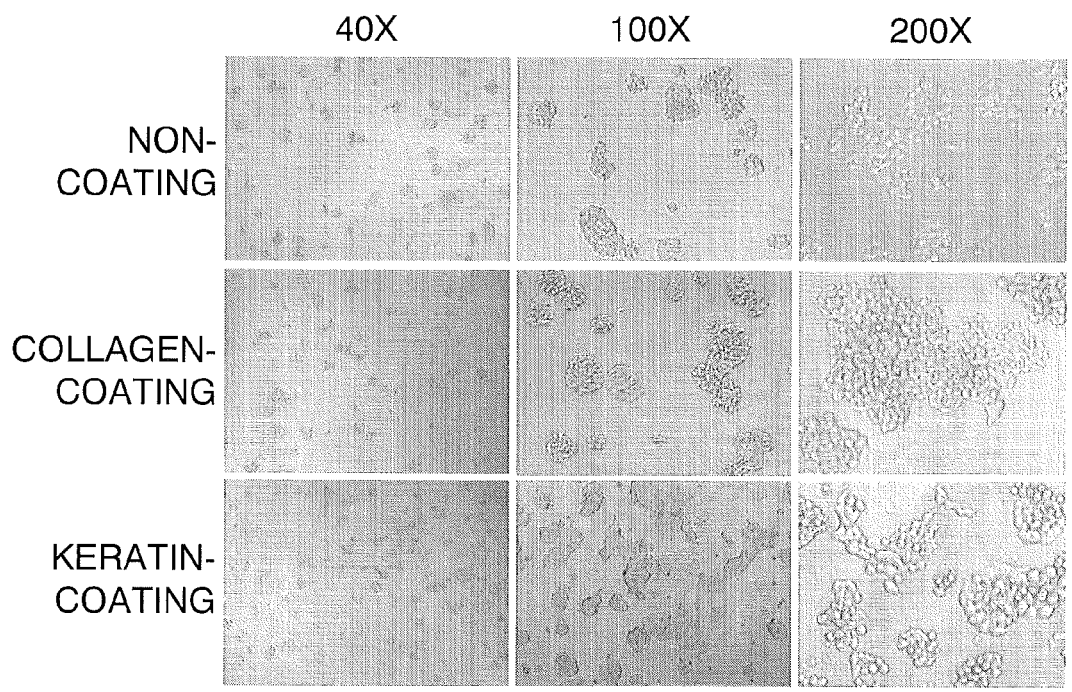
FIG. 3. Microscopy images at Day 7 of non-coated, collagen-coated and keratin-coated cell culture surfaces at 40×, 100× and 200×.
Figure 4:
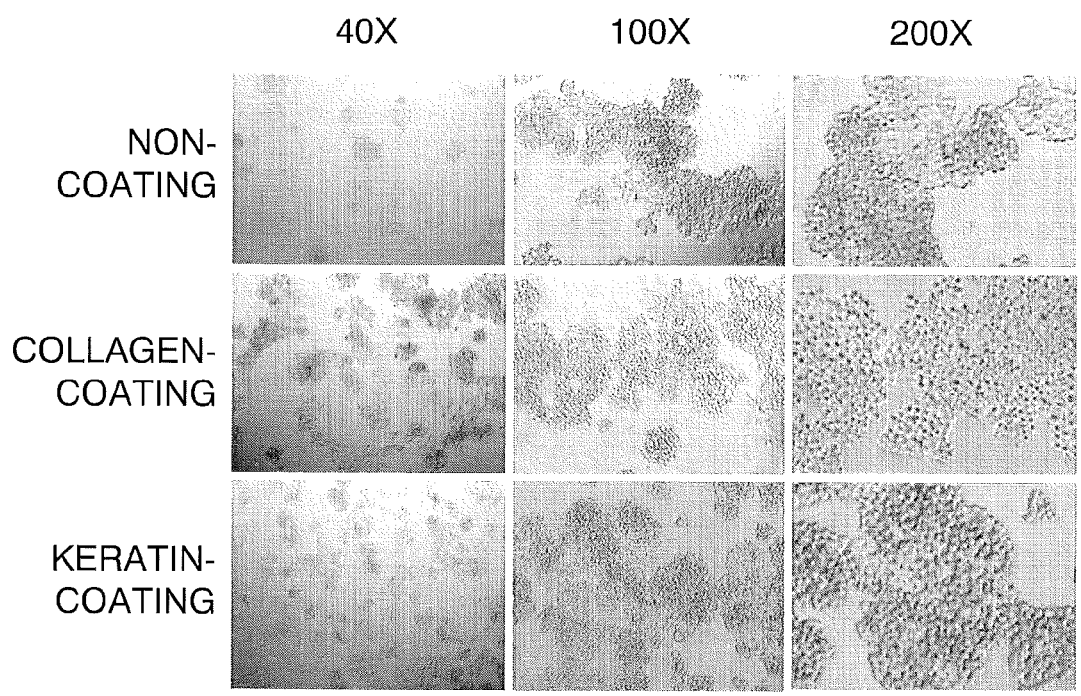
FIG. 4. Microscopy images at Day 14 of non-coated, collagen-coated and keratin-coated cell culture surfaces at 40×, 100× and 200×.

A 100 µg/ml kerateine solution was prepared by diluting 0.5 ml of a 10 mg/ml kerateine stock solution 100× by addition of 50 ml of deionized water to make 50 ml of a 100 µg/ml working solution. The working solution was filtered through a 0.4 µm filter, and then filtered through a 0.22 µm filter. The solution was then used to coat the wells of a 96-well plate (30 µl solution) or a 24-well plate (200 µl solution). Plates were incubated for 48 hours at 37° C., during which time the kerateine adhered to the well. Excess coating solution was removed, and the wells were washed with phosphate buffered saline (PBS) twice. Plates were covered to keep the wells from drying and stored at 4° C. Wells were washed with PBS before seeding with cells. An acidic collagen coating was similarly prepared. Beta TC-6 cells (insulin-producing cells from mouse with insulinoma) were used to measure cell adhesion and proliferation (FIGS. 3-4).

Figure 5:
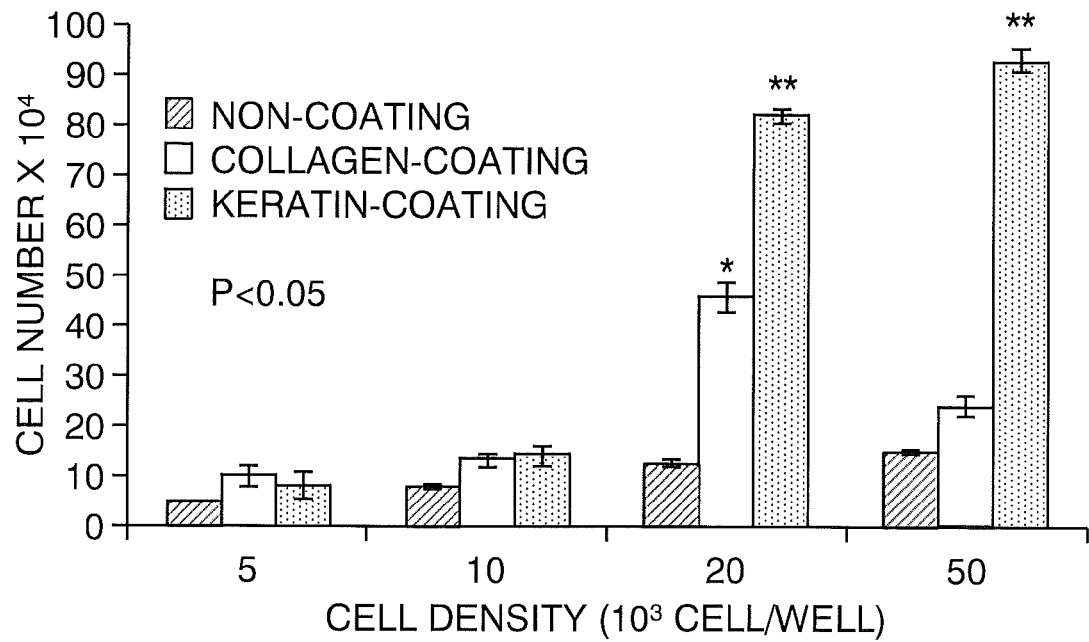
FIG. 5. Effect of cell density on cell growth (measured by cell number) in vitro at Day 7 of non-coated, collagen-coated and keratin-coated cell culture surfaces. Collagen and keratin were dissolved in PBS.

Results: Beta TC-6 cells were able to attain a higher density with the keratin-coated plates than the collagen-coated and non-coated plates (FIG. 5). Different solutions—PBS, acetic acid and distilled water—were used to make the dilution from the stock into the working solution for coating. Observations are summarized in Table 1.

Figure 6:
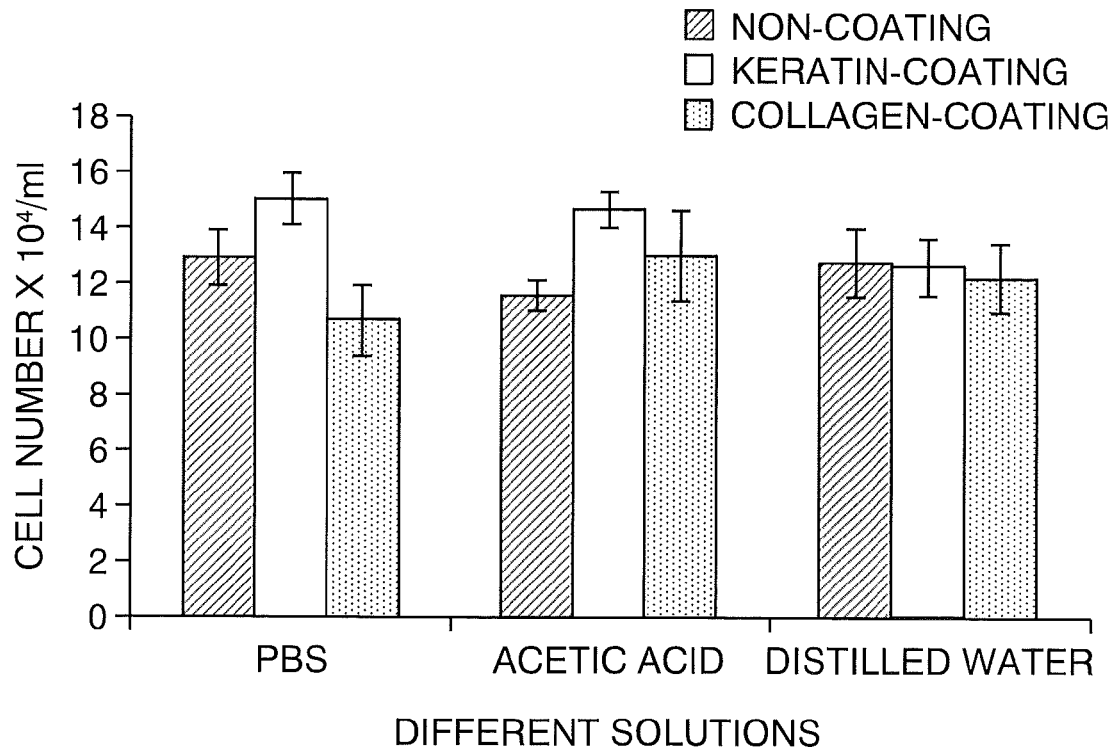
FIG. 6. Beta TC-6 cell growth at Day 7 in coatings prepared with different solutions.

This variation in solution had no significant effect on cell density (FIG. 6). (Note, however, that in some instances acetic acid should not be used because it may fractionate the material during coating.)

Figure 7:
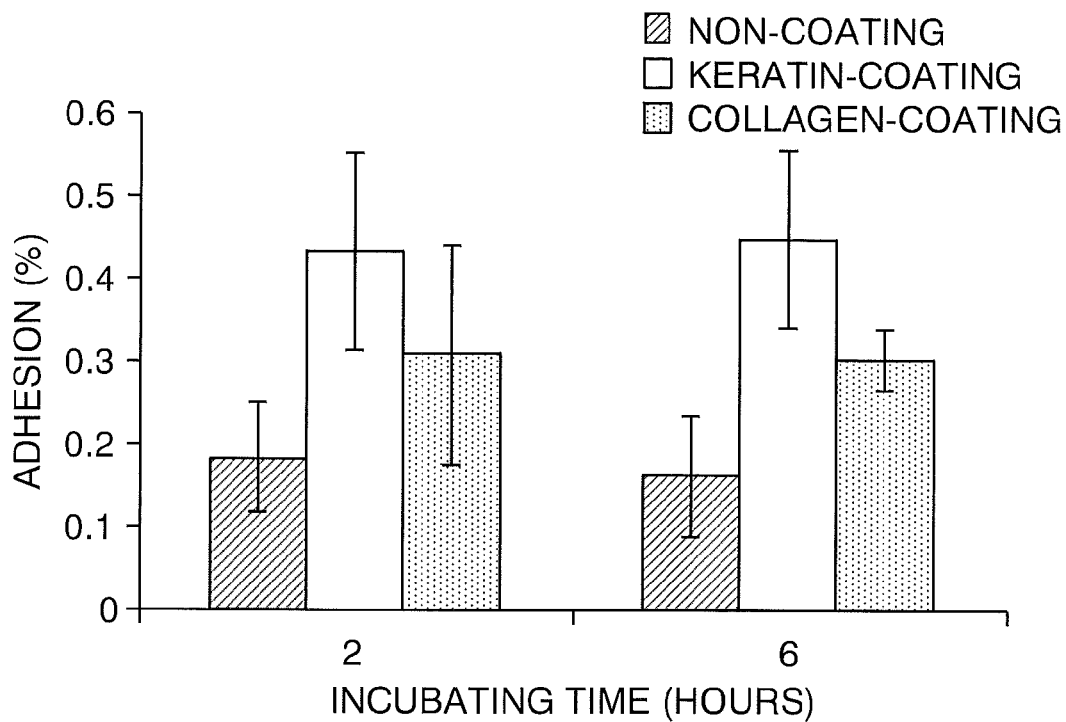
FIG. 7. Percent adhesion of Beta TC-6 cells upon incubation for 2 and 6 hours in non-coated, collagen-coated and keratin-coated cell culture surfaces. Keratin was dissolved in distilled water, and collagen was dissolved in acetic acid.
Figure 8A:
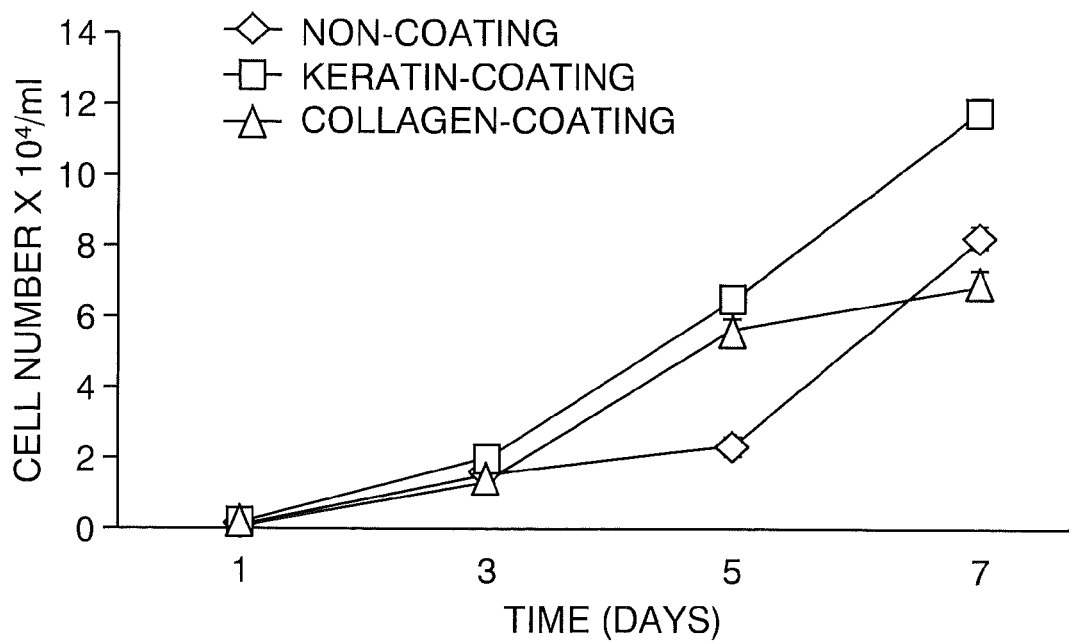
FIGS. 8A-8B. Cell growth curves (wet-coating) over 7 days with non-coated, keratin-coated and collagen-coated cell culture surfaces. 8A: keratin and collagen were dissolved in PBS (initial cell density $20\times10^3$/ml). 8B: keratin was dissolved in distilled water, and collagen was dissolved in acetic acid.
Figure 8B:
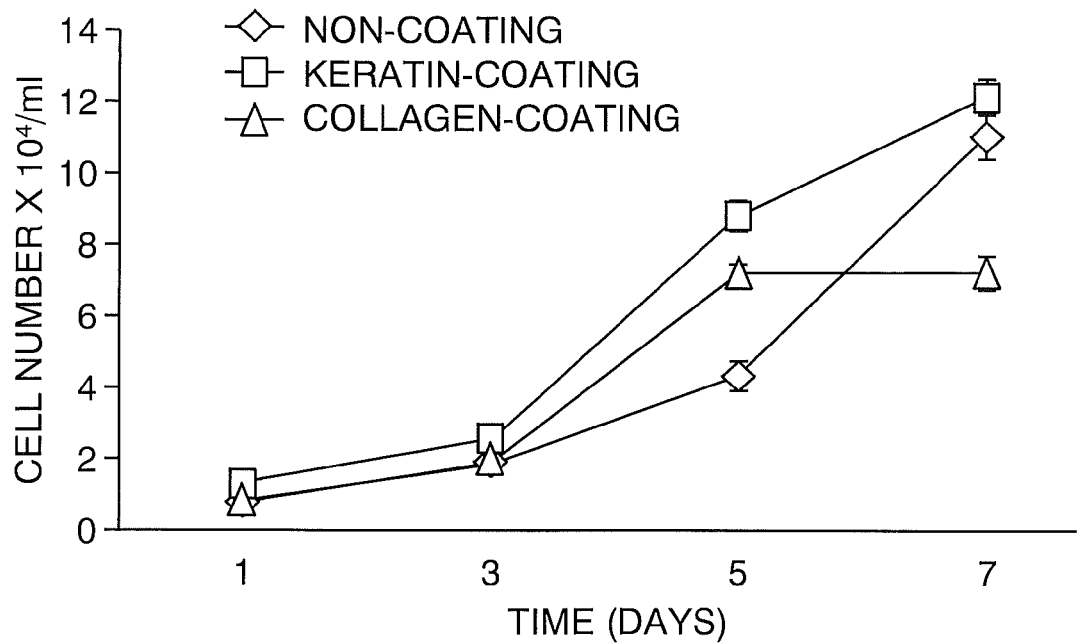
Figure 9:
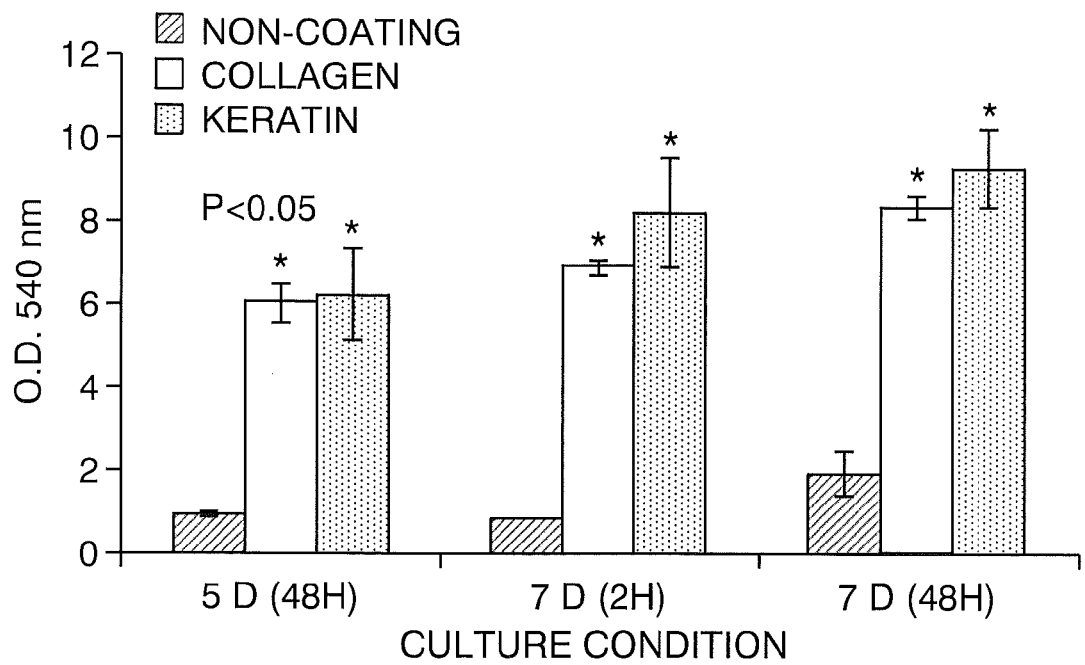
FIG. 9. Effect of keratin coating on insulin secretion of Beta TC-6 cells.

Cell adhesion in the keratin-coated plates was significantly higher than the non-coated plates, but not significantly different from the collagen-coated plates (FIG. 7). Insulin secretion by the Beta TC-6 cells grown on both keratin-coated and collagen-coated plates was significantly higher than non-coated plates (FIG. 9).

Example 4

Cell Culture with Keratin Microparticles

1. Remove media from the source culture flask or dish.
2. Rinse with 5 mL of Dulbecco's Phosphate-Buffered Saline (D-PBS) and remove.
3. Add 1 mL of pre-warmed 0.05% Trypsin-EDTA to the flask.
4. Incubate until the cells have detached (about 5 to 10 minutes at room temperature).
5. Add 5 mL of growth medium containing 500 µg/mL Soybean Trypsin Inhibitor to the flask and gently triturate. Transfer the cell suspension to a 15 mL centrifuge tube.
6. Determine viable and total cell counts.
7. Centrifuge the cells for 10 minutes at 100×g.
8. Aspirate the supernatant and gently resuspend the cell pellet in the desired volume of pre-warmed, complete growth medium.
9. Transfer the cells to a spinner flask containing the desired amount of microparticles (cells should be seeded at a sub-confluent density so as not to induce contact inhibition, if desired). Put the flask in an incubator with caps loosened to allow for oxygenation/aeration and gently agitate.
10. Alternately, microparticles can be spread on the bottom of a culture flask and cells seeded statically on top or some combination of 9 and 10.
11. Replace media with fresh, complete growth media every 2 to 3 days by first allowing the microparticles to settle and then aspirating and replacing the majority of the supernatant.

Example 5

Keratose Samples

Keratose fractions were obtained using a method based on that of Alexander and coworkers. However, the method was substantially modified to minimize hydrolysis of peptide bonds. Briefly, 50 grams of clean, dry hair that was collected from a local barber shop was reacted with 1000 mL of an aqueous solution of 2 w/v % peracetic acid (PAA) at room temperature for 12 hr. The oxidized hair was recovered using a 500 micron sieve, rinsed with copious amounts of deionized water, and the excess water removed. Keratoses were extracted from the oxidized hair fibers with 2000 mL of 100 mM Trizma® base. After 2 hr, the hair was separated by sieve and the liquid neutralized by dropwise addition of hydrochlo-

TABLE 1

Beta TC-6 Cell Growth at Day 7 in Different Solutions.

| Solution | PBS | PBS | | ddw | ddw | | Acetic acid | Acetic acid | |
|---|---|---|---|---|---|---|---|---|---|
| Coating materials | Keratin | Collagen | Non | Keratin | Collagen | Non | Keratin | Collagen | Non |
| Dish background | Brown fragment | Brown fragment | Clear | Brown fragment | Brown fragment | Clear | Clear | Clear | Clear |
| Cell growth pattern | small | large | small | large | large | small | large | large | small |
| Cell number ×10$^4$/ml | 15.03 | 10.67 | 12.95 | 12.63 | 12.25 | 12.76 | 14.62 | 13.05 | 11.57 | ric acid (HCl). Additional keratoses were extracted from the remaining hair with 2000 mL of DI water. Each time the hair was separated by sieve and the liquid neutralized with HCl. Both extracts were combined, centrifuged, and any residual solid material removed by filtration.

Alpha-keratose was removed from the crude extract by dropwise addition of concentrated HCl to a pH of 4.2. The alpha keratose was isolated by centrifugation, re-dissolved in a minimal amount of 0.1M NaOH, reprecipitated with concentrated HCl at pH 4.2, redissolved in a minimal amount of 0.1M NaOH, neutralized to pH 7.4, and purified by dialysis against DI water using 3.5 KDa nominal low molecular weight cutoff (NLMWCO) tubing. The dialyzed alpha-keratose was neutralized to pH 7.4, freeze dried and ground into a fine powder.

The gamma-keratose remaining dissolved in the supernatant of the first precipitation was clarified by filtration and neutralized to pH 7.4. The gamma-keratose was purified using a tangential flow dialysis system with a pump and 1.0 kDa NLMWCO cartridge. The gamma keratose solution was concentrated using the same system, neutralized to pH 7.4, lyophilized, and ground into a fine powder.

Alpha- and gamma-keratose samples were dissolved separately in DI water at a concentration of 2 wt/vol % and the pH adjusted to 6.0 using 1M HCl. Each sample was fractionated separately on an ion exchange chromatography column packed with Q-Sepharose media. The column was pre-conditioned with 10 mM tris at pH 6.0. After loading the keratin solution, the column was rinsed with 10 mM tris at pH 6.0. Both the loading and rinse solutions were retained as labeled as acidic alpha- or gamma-keratose, respectively. Basic alpha- or gamma-keratose was eluted from the column using 2M NaCl in 100 mM tris at pH 11. The alpha-keratose solutions were neutralized to pH 7.4 and dialyzed against DI water in 12.4 KDa NLMWCO tubing. The gamma-keratose solutions were neutralized to pH 7.4 and dialyzed against 3.5 KDa NLMWCO tubing. Most of the gamma-keratose bound to the column; a small amount was eluted in the 10 mM pH 6 wash solution and was considered weakly basic. The majority of the sample was recovered in the NaCl eluent and was considered basic. After dialysis, the solutions were neutralized to pH 7.4, lyophilized, and ground into fine powders. This process produced purified acidic and basic fractions of alpha-keratose, and weakly basic and basic gamma-keratose.

Figure 10:
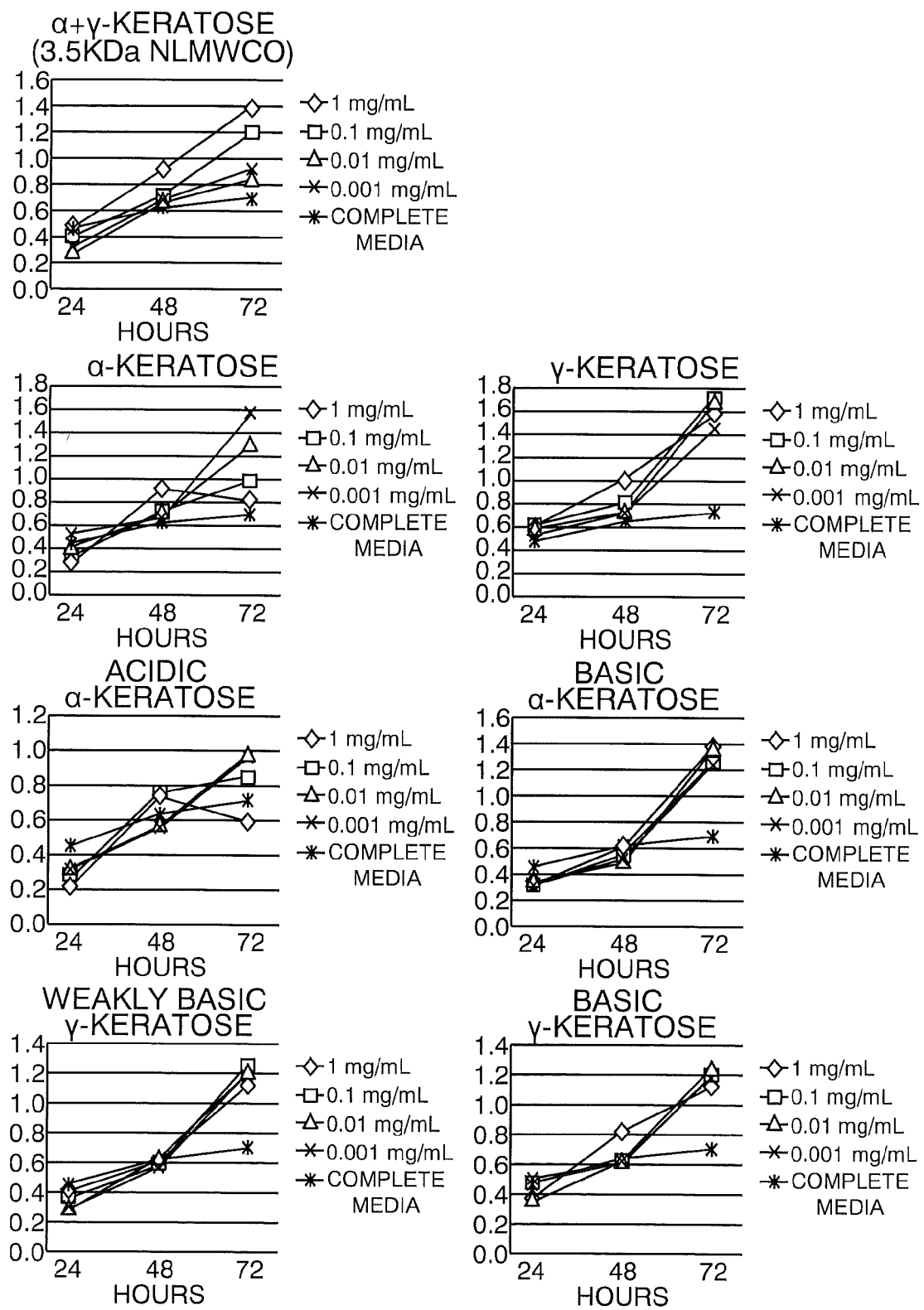
FIG. 10. Results of addition of keratose fractions to media used to grow Schwann cells. Cell proliferation was measured using the MTS assay at 24, 48 and 72 hours.

Keratose fractions were added to media (low glucose DMEM with 10% serum) at concentrations ranging from 0.001 to 1 mg/mL and used to grow Schwann cells. At 24, 48, and 72 hours, proliferation of the cells was measured using an MTS assay. Results are shown in FIG. 10.

Figure 11:
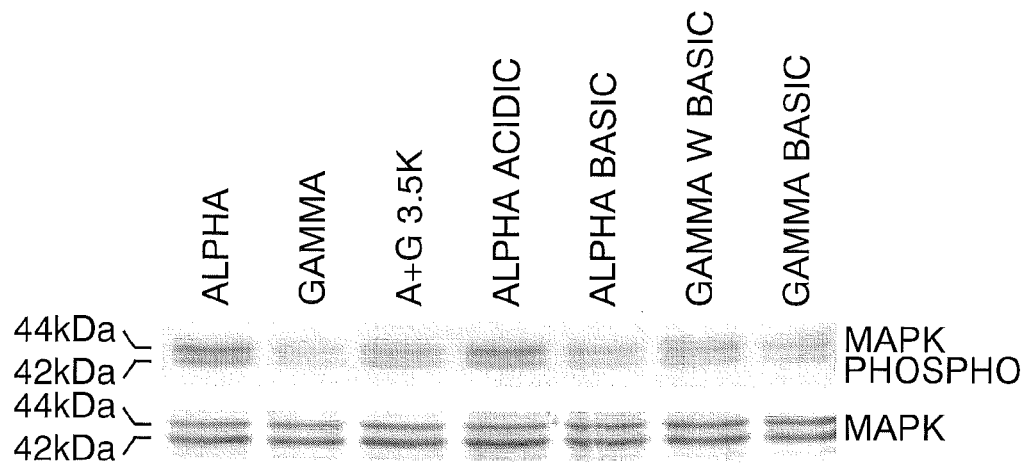
FIG. 11. Western blot of protein expression following 72 hours of Schwann cell culture on keratin coated cultureware.

Keratose fractions were also used to coat standard tissue culture dishes by overnight incubation with 100 µg/mL solutions, prepared as described above in Example 3. The coatings were gently rinsed with phosphate buffered saline (PBS) and Schwann cells seeded. After 72 hours of culture, the cells were lysed and protein expression investigated by western blot. Results are shown in FIG. 11.

These data demonstrate the utility of employing keratin fractions as both substrates and a media additive to facilitate the growth and function of these cells.

Example 6

Ion Exchange Chromatography of Keratose

Just prior to fractionation, keratose samples were re-dissolved in ultrapure water and titrated to pH 6 by addition of dilute HCl solution. The samples were loaded onto a 200 mL flash chromatography column containing either DEAE-Sepharose (weakly anionic) or Q-Sepharose (strongly anionic) exchange resin (50-100 mesh; Sigma-Aldrich, Milwaukee, Wis.) with gentle pressure and the flow through collected (acidic keratin). A small volume of 10 mM Trizma® base (approximately 200 mL) at pH 6 was used to completely wash through the sample. Basic keratin was eluted from the column with 100 mM tris base plus 2M NaCl at pH 12. Each sample was separately neutralized and dialyzed against DI water using tangential flow dialysis with a LMWCO of 1 KDa, concentrated by rotary evaporation, and freeze dried.

Example 7

Comparison of Keratin Fractions in Cell Culture

Figure 12:
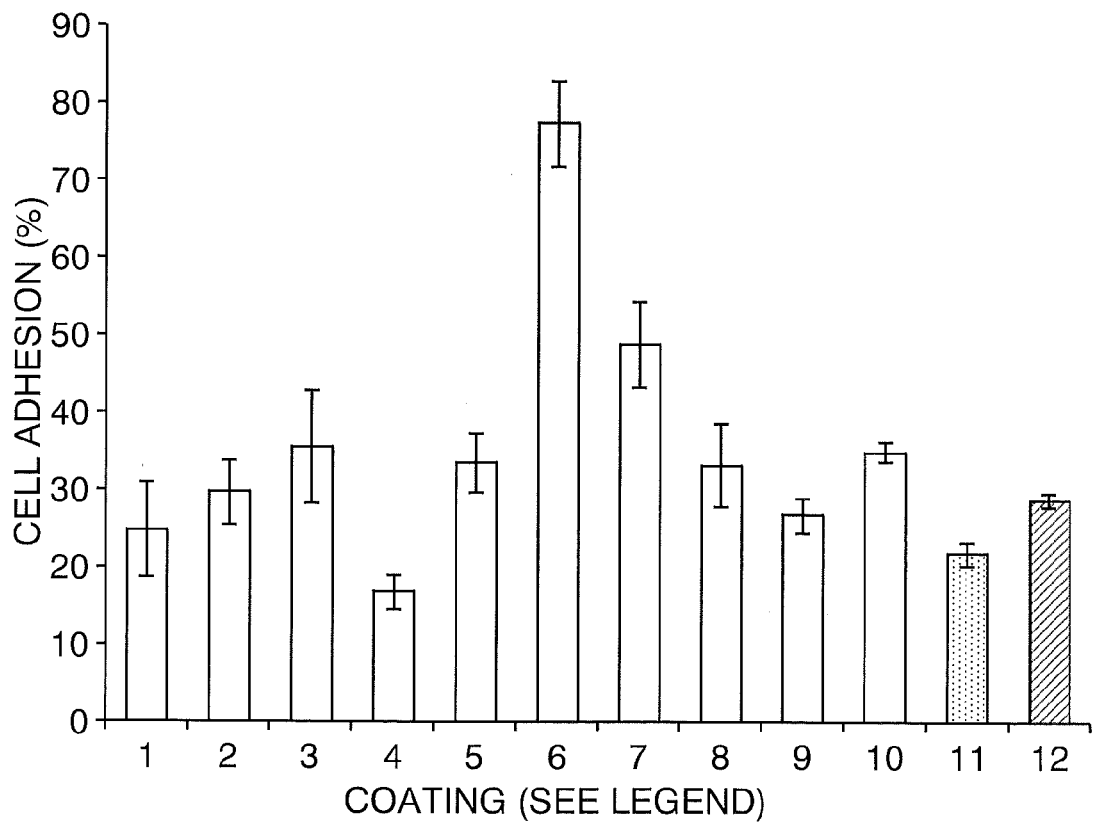
FIG. 12. β-TC6 Cell Adhesion on Keratin Coatings. Coating numbers correspond to: (1) keratose; (2) α-keratose, (3) γ-keratose, (4) basic α-keratose, (4) acidic α-keratose, (6) basic γ-keratose, (7) acidic γ-keratose, (8) kerateine, (9) α-kerateine, (10) γ-kerateine, (11) uncoated, and (12) collagen. Several keratin fractions demonstrate better adhesion of the cells than does collagen, including the basic γ-keratose to which more than twice the number of cells adhered.

Human hair from a local barber shop was used to derive several keratin biomaterials. Hair was washed with mild detergent, rinsed, and dried. The clean hair was either oxidized or reduced to produce α+γ-keratose or α+γ-kerateine crude fractions, respectively. The α-keratins were precipitated by dropwise addition of HCl. The α-keratins were separated by centrifugation and the supernatant containing the γ-keratins was filtered, neutralized and dialyzed against deionized (DI) water. The α-keratins were re-dissolved in 0.1M NaOH, neutralized, and dialyzed against DI water. After three days of dialysis, the keratose solutions were titrated to pH 6.0 and loaded onto an anionic exchange column and separated in to acidic and basic fractions. The kerateine fractions were not further separated but stored for further use. This resulted in the creation of the following keratin fractions:

1. α+γ-keratose
2. α-keratose
3. γ-keratose
4. Basic α-keratose
5. Acidic α-keratose
6. Basic γ-keratose
7. Acidic γ-keratose
8. α+γ-kerateine
9. α-kerateine
10. γ-kerateine Coatings of each of these fractions, as well as collagen I, were created on standard tissue culture microwell plates by overnight incubation of 100 µg/mL solutions at 37° C. Each well was rinsed twice with phosphate-buffered saline (PBS) before use. Uncoated wells were also used as a control. Cell adhesion with β-TC6 cells on the various keratose/kerateine coatings was measured using the Vybrant™ Cell Adhesion Assay Kit. Briefly, cells were seeded at $1 \times 10^5$ cells per well and allowed to adhere for 4 hours in an incubator. Non-adherent cells were rinsed off with PBS and adherent cells labeled with 20 mM of calcein AM for 30 min at 37° C. incubation to incorporate the fluorescent dye. Fluorescence was measured using a Millipore Cytofluor 2350 reader to obtain total fluorescence, after which, the cells were removed following the procedures described in the kit and the background fluorescence measured. The percentage of adhesion was calculated using the formula: % cell adhesion=(fluorescence in adherent cells/total fluorescence)×100. These data are shown in FIG. 12.

Figure 13:
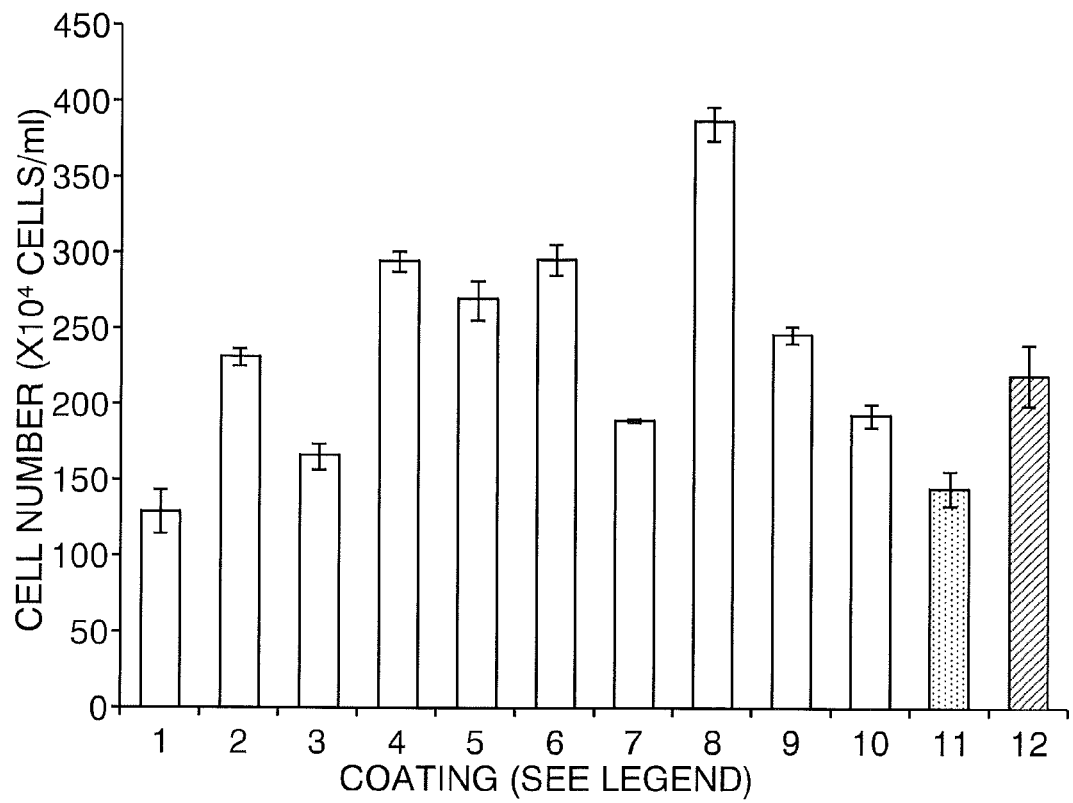
FIG. 13. β-TC6 Cell Proliferation on Keratin Coatings. Coating numbers correspond to: (1) keratose; (2) α-keratose, (3) γ-keratose, (4) basic α-keratose, (4) acidic α-keratose, (6) basic γ-keratose, (7) acidic γ-keratose, (8) kerateine, (9) α-kerateine, (10) γ-kerateine, (11) uncoated, and (12) collagen. Several keratin fractions demonstrate better cell proliferation after seven days of culture than collagen. Cells grew particularly well on the kerateine substrate.

To evaluate the effect of keratin coatings on cell proliferation, β-TC6 cells were seeded at $1 \times 10^5$ cells per well onto coated microwell plates. Cells were grown at 37° C., 5% $CO_2$ and 95% relative humidity (RH) with media changes every three days. At seven days, the cells were trypsinized, resuspended in saline, and counted using a Coulter counter. These data are shown in FIG. 13.

Figure 14:
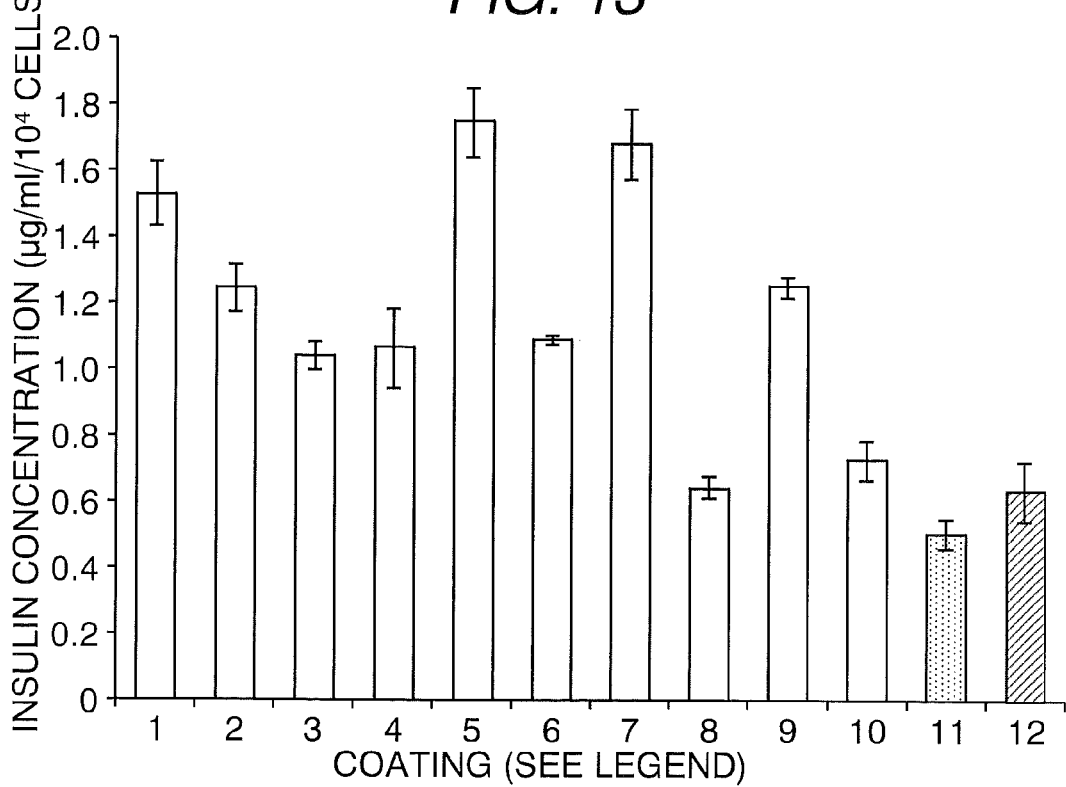
FIG. 14. β-TC6 Insulin Secretion on Keratin Coatings. Coating numbers correspond to: (1) keratose; (2) α-keratose, (3) γ-keratose, (4) basic α-keratose, (4) acidic α-keratose, (6) basic γ-keratose, (7) acidic γ-keratose, (8) kerateine, (9) α-kerateine, (10) γ-kerateine, (11) uncoated, and (12) collagen. Several keratin fractions demonstrate better maintenance of insulin secretion activity than collagen.

Functionality of the βTC-6 cells was determined by analyzing insulin production of cells grown on keratin coatings. Cells were seeded at a density of $1 \times 10^4$ and grown in DMEM media containing 25 mM glucose and 10% serum, 37° C., 5% $CO_2$, and 95% RH. After 1 week of culture, the cells were washed twice with PBS and incubated with DMEM containing 5.5 mM glucose without serum. This step was performed to keep insulin secretion at a basal level. After 12 hours of incubation in low glucose/no serum, cells were washed two times with PBS and incubated in pre-warmed DMEM media containing 25 mM glucose and 10% serum for 2 hours. The higher concentration of glucose in the media served as an inducer for insulin secretion. Cell culture media (total of 1 ml) was collected prior to induction for baseline insulin secretion determination and after 2 hours of induction. The media was centrifuged at 3000 g for 10 min to pellet free floating cells/debris and used immediately for insulin ELISA assay (Mercodia, Winston Salem, N.C.), or stored at −80° C. until assayed, according to the manufacturer's instructions. The amount of secreted insulin is given in μg/l above baseline normalized to the number of cells and is shown in FIG. 14.

When cultured on treated polystyrene or a collagen I coating, the cultures were not able to propagate, cells lost their phenotype and stopped producing insulin, and eventually apoptosed. This was not the case for keratin fractions, as the cells continued to produce insulin and remained glucose responsive for up to 14 days. However, this was true only for certain types of keratins, thus demonstrating the benefits of fractionation and the methodologies taught herein.

These keratin fractions are also compared upon culture thereon of primary cultures, e.g., primary islet cells, compared upon culture thereon of stem cells (e.g., embryonic stem cells, amniotic fluid stem cells, hematopoietic stem cells, etc.).

Example 8

Comparison of Keratin Fractions in Culture of Dermal Fibroblasts

Figure 15:
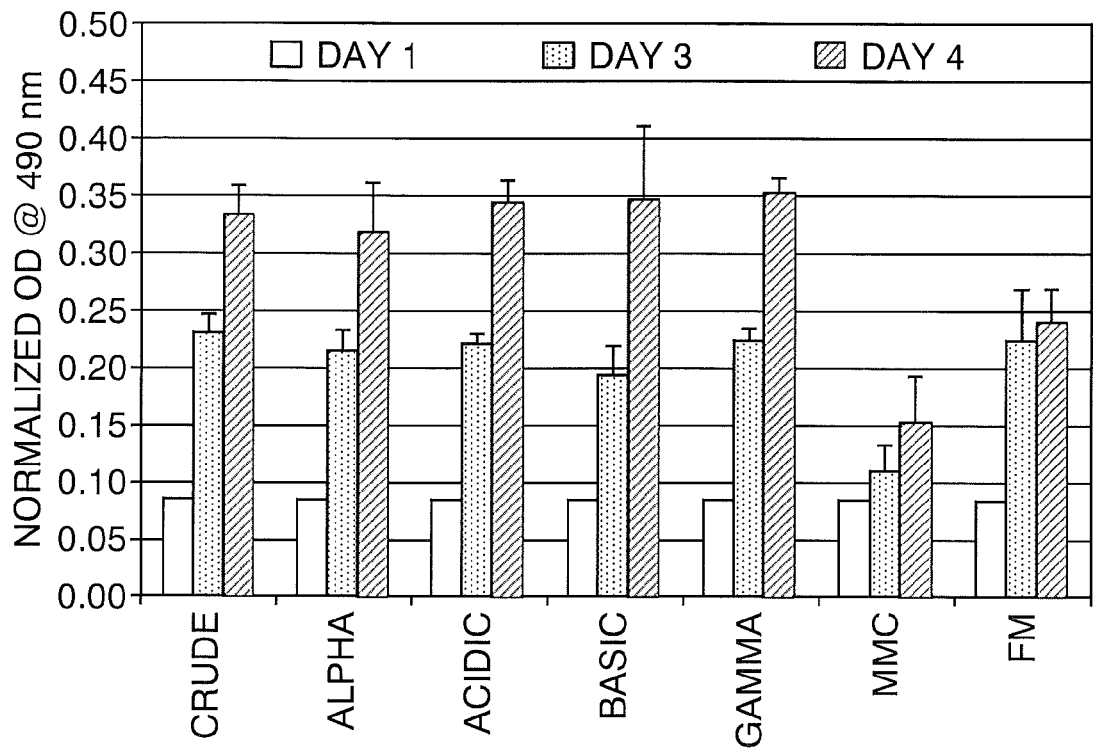
FIG. 15. Density of mouse dermal fibroblast cells at days 1, 3 and 4, grown in test media containing keratose (fibroblast growth media+keratin fractions at a concentration of 10 mg/mL). Negative control cultures were treated with 16 mg/mL mitomycin C (MMC) for 30 minutes to inhibit proliferation. The positive control was normal fibroblast growth media (FM).

The growth of dermal fibroblasts in the presence of soluble keratin biomaterials was tested in culture. Mouse dermal fibroblast cells were seeded at 5,000 cells per well and allowed to attach and grow in normal fibroblast growth media (DMEM+1% antibiotics+1% fetal bovine serum). After 24 hours, the media was changed to the test media containing keratose (fibroblast growth media+keratin fractions at a concentration of 10 mg/mL). Negative control cultures were treated with 16 mg/mL mitomycin C (MMC) for 30 minutes to inhibit proliferation. The positive control was normal fibroblast growth media (FM). Cells numbers were determined using an MTS assay at days 1, 3, and 4. The results are shown in FIG. 15.

Example 9

Promotion of Cell Adhesion

Figure 16:
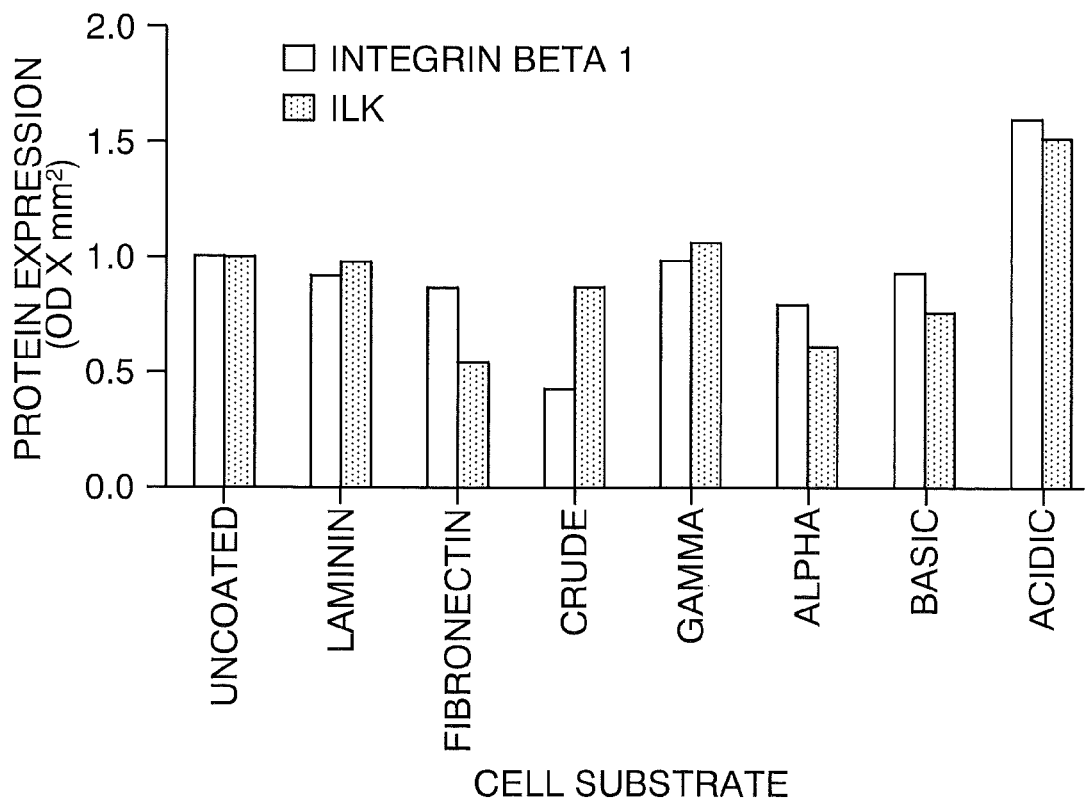
FIG. 16. Western blot comparison of keratin coatings for ability to up-regulate integrin β1 and integrin linked kinase (ILK). The cells cultured on the alpha keratins (type 1+2) had the highest expression of the integrin β1 receptor subunit as well as integrin linked kinase which phosphorylates the intracellular domain of integrin β1.

To analyze keratin's ability to up-regulate cell adhesion and signaling molecules as a surrogate extra-cellular matrix, phosphate-buffered saline (PBS) solutions of equal concentrations were prepared with laminin, fibronectin, crude, alpha and gamma keratose and 8 mls of each solution was used as a plate coating in 10 cm tissue culture plates by incubation for one hour at room temperature. The plates were then rinsed 3 times with sterile PBS. RT4 cells in complete media were plated at a density of 20,000 cells per $cm^2$ and allowed to reach 90% confluency after 72 hours. Protein was harvested from the cells and quantified with a Lowry assay. The proteins were then resolved by gel electrophoresis and transferred to a western blot membrane. The membrane was probed with antibodies for integrin β1, integrin linked kinase (ILK) using GAPDH as a loading control and the band intensity was analyzed by densitometry. The cells cultured on the alpha keratins (type 1+2) had the highest expression of the integrin β1 receptor subunit as well as integrin linked kinase which phosphorylates the intracellular domain of integrin β1. These data are shown in FIG. 16.

Figure 17:
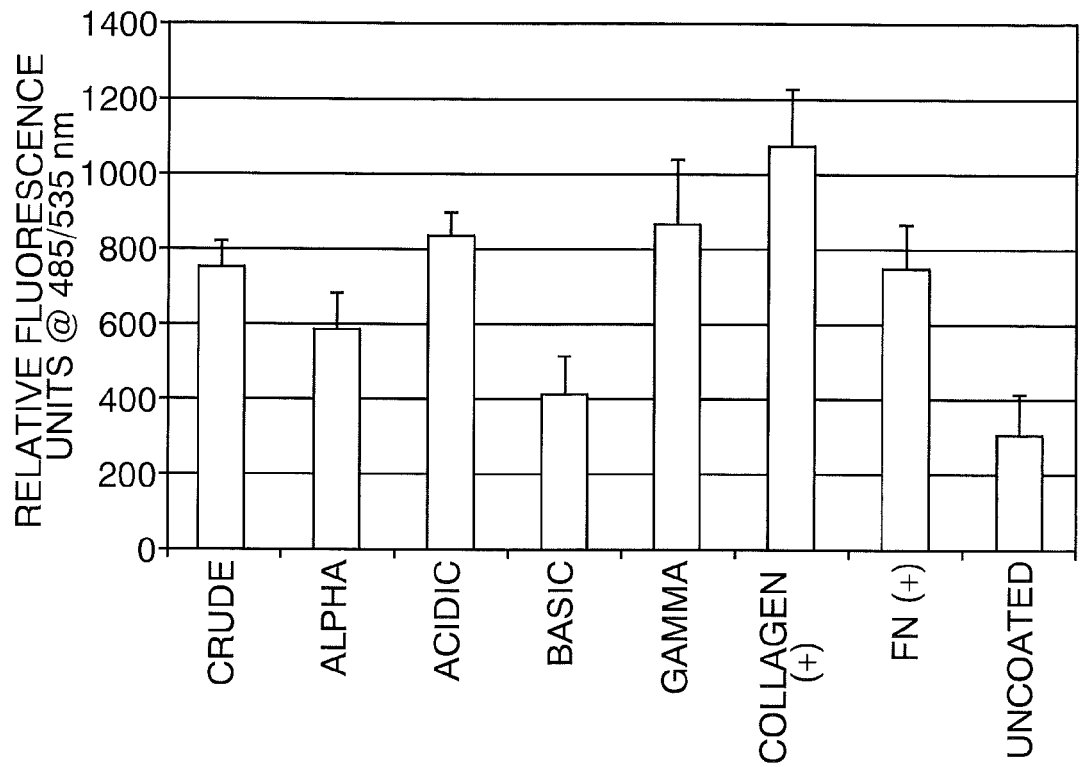
FIG. 17. Comparison of keratin coatings on dermal fibroblast cell adhesion.

The effect of keratin coatings on dermal fibroblast cell adhesion was tested. Fractions of keratose were coated using 200 mg/mL solutions by overnight incubation, after which, excess solution was removed and the coating rinsed twice with phosphate-buffered saline (PBS). Neonatal mouse dermal fibroblasts were seeded at 5,000 cells per well and allowed to adhere for 2 hours. Non-adherent cells were removed by gentle rinsing with PBS and a solution containing Calcein AM added. The cells were incubated for 30 minutes and the excess solution aspirated. The cells were rinsed with PBS and fluorescence read at 485/530 nm (excitation/emission). The results are shown in FIG. 17.

Example 10

Osteogenic Differentiation of Adipose Derived Stem Cells

Figure 18A:
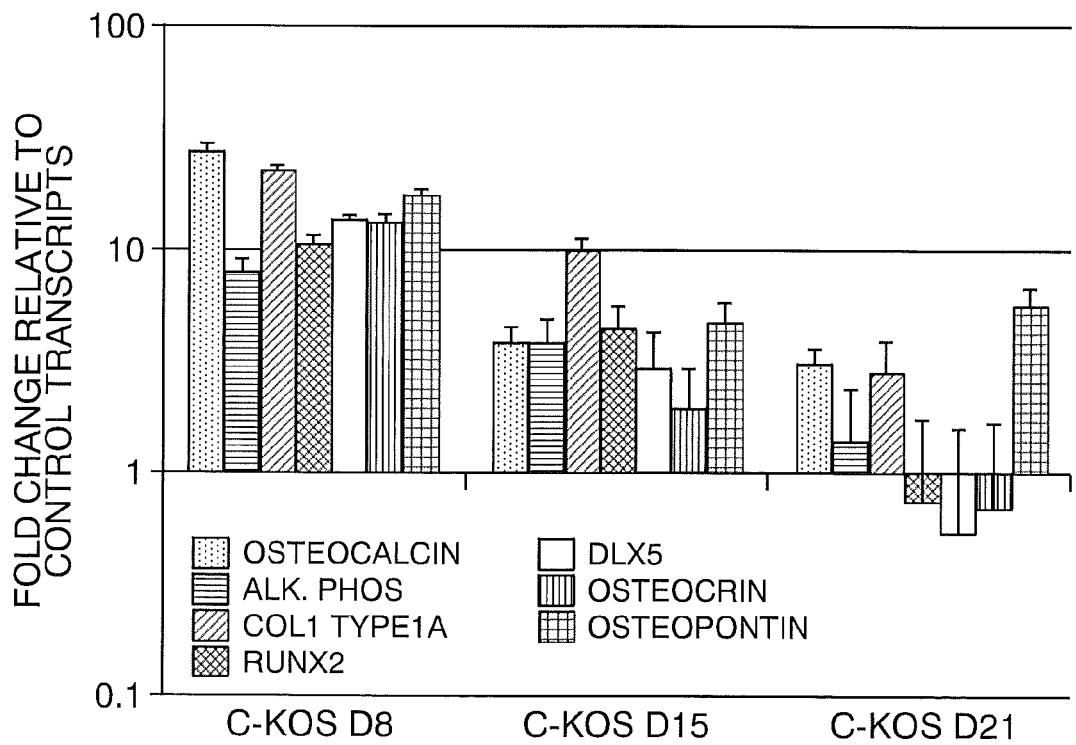
FIG. 18A-18C. Osteogenic differentiation of human adipose derived stem cells (ADSC) in the presence of keratin biomaterial coatings. Quantitative PCR was performed using primers for specific markers which are correlated with osteoblastic phenotype: runt-related transcription factor 2 (RUNX2), DLX-5 (positive regulator of Runx2), collagen type I alpha 1 (COL1A1), alkaline phosphatase (ALPL), and bone gamma-carboxyglutamate (BGLAP) (coding for the osteocalcin protein), osteocrin and osteopontin. Results were normalized to an internal GAPDH gene control and gene expression related to control cultures containing no keratose as shown below (Legend: C-KOS=crude keratose, A-KOS=alpha-keratose, G-KOS=gamma-keratose, DX=days of treatment).
Figure 18B:
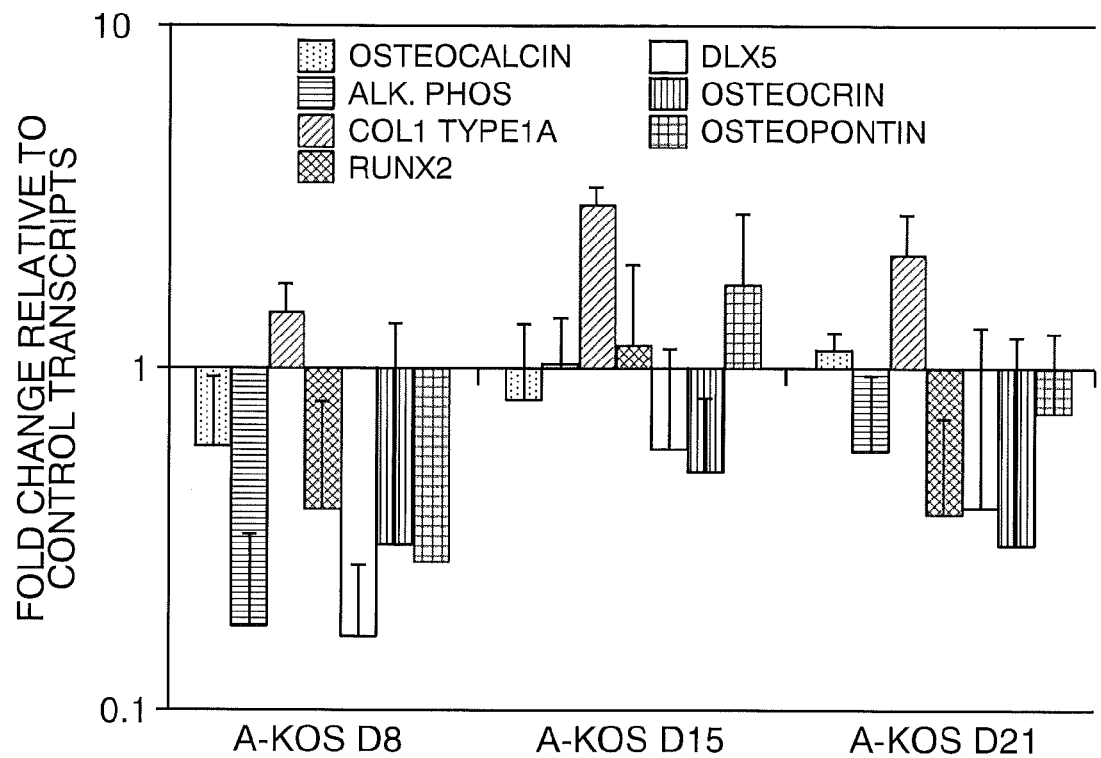
Figure 18C:
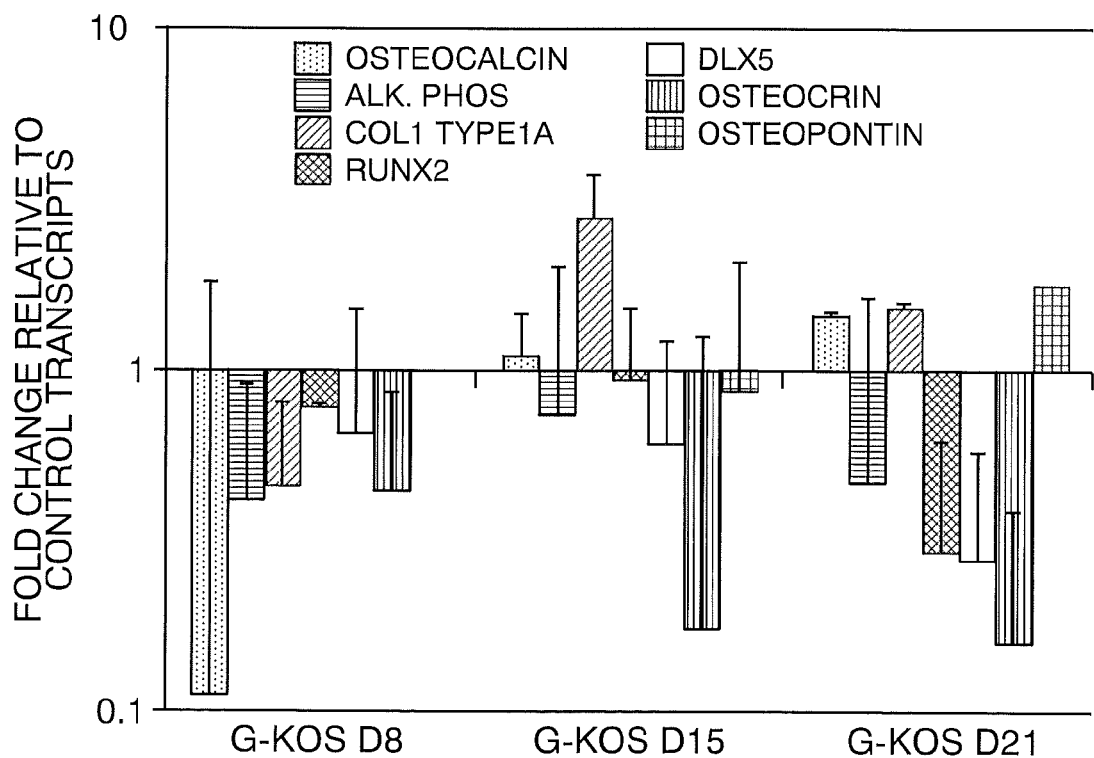

Human adipose derived stem cells (ADSC) were used to study osteogenic differentiation in the presence of keratin biomaterial coatings. The ADSC were isolated by centrifugal force following collagenase treatment from subcutaneous adipose tissue collected from donors undergoing elective surgery. At passage 2, ADSC expressed stem cell-related surface antigens (CD13, CD29, CD44, CD73, CD105 and CD166) and were subsequently induced to differentiate towards the osteogenic lineage for 3 weeks of culture in DMEM low glucose culture media supplemented with 100 nM dexamethasone, 50 mM ascorbic acid, 10 mM β-glycerophosphate disodium salt pentahydrate and 0.03 mg/ml keratose (crude, alpha or gamma fraction). Quantitative PCR was performed using primers for specific markers which are correlated with osteoblastic phenotype: runt-related transcription factor 2 (RUNX2), DLX-5 (positive regulator of Runx2), collagen type I alpha 1 (COL1A1), alkaline phosphatase (ALPL), and bone gamma-carboxyglutamate (BGLAP) (coding for the osteocalcin protein), osteocrin and osteopontin. Results were normalized to an internal GAPDH gene control and gene expression related to control cultures containing no keratose as shown below (Legend: C-KOS=crude keratose, A-KOS=alpha-keratose, G-KOS=gamma-keratose, DX=days of treatment). Results are shown in FIG. 18.

The foregoing is illustrative of the present invention, and is not to be construed as limiting thereof. The invention is defined by the following claims, with equivalents of the claims to be included therein.

That which is claimed is:
1. A cell culture substrate comprising a keratin coating, said keratin coating in the form of a gel or a freeze dried gel, wherein said keratin is obtained by isolating a fraction of keratin selected from the group consisting of: acidic keratose, basic keratose, acidic kerateine and basic kerateine.

2. The substrate of claim 1, wherein said fraction of keratin is selected from the group consisting of: basic α-keratose, acidic α-keratose, basic γ-keratose, acidic γ-keratose, basic α-kerateine, acidic α-kerateine, basic γ-kerateine and acidic γ-kerateine.

3. The substrate of claim 1, wherein said fraction of keratin is selected from the group consisting of: acidic keratose and basic keratose.

4. The substrate of claim 1, wherein said fraction of keratin is selected from the group consisting of: basic γ-keratose and acidic γ-keratose.

5. The substrate of claim 1, wherein said fraction of keratin is selected from the group consisting of: acidic α-keratose, basic γ-keratose, acidic γ-keratose.

6. The substrate of claim 1, wherein said fraction of keratin is acidic kerateine or basic kerateine.

7. The substrate of claim 1, wherein said keratin is in the form of a gel, said gel comprising between 5 and 30 percent of said keratin by weight.

8. The substrate of claim 1, wherein said substrate comprises polystyrene or polypropylene.

9. The substrate of claim 1, wherein said substrate is a petri dish, a 2-well plate, 6-well plate, a 12-well plate, a 24-well plate, or a 96-well plate.

10. The substrate of claim 1, wherein said substrate is an insert configured to be placed into a cell culture dish.

11. The substrate of claim 10, wherein said substrate comprises polycarbonate or polyester.

12. The substrate of claim 10, wherein said cell culture dish is a petri dish, a 6-well plate, a 12-well plate, or a 24-well plate.

13. A method for growing cells in vitro comprising the steps of:
   contacting said cells to a cell culture substrate comprising a keratin coating, said keratin coating in the form of a gel or a freeze dried gel, wherein said keratin is obtained by isolating a fraction of keratin selected from the group consisting of: acidic keratose, basic keratose, acidic kerateine and basic kerateine, wherein said cells adhere to said keratin coating; and
   growing said cells in vitro under conditions conducive to the proliferation of said cells.

14. The method of claim 13, wherein said fraction of keratin is selected from the group consisting of: basic α-keratose, acidic α-keratose, basic γ-keratose, acidic γ-keratose, basic α-kerateine, acidic α-kerateine, basic γ-kerateine, basic γ-kerateine and acidic γ-kerateine.

15. The method of claim 13, wherein said cells are stem cells and said growing is performed under conditions conducive to the differentiation of said stem cells.

16. The method of claim 13, wherein said cells are stem cells.

17. The method of claim 13, wherein said cells are embryonic stem cells, amniotic fluid stem cells, or multipotent stem cells.

18. The method of claim 13, wherein said cells are a cell strain or cell line.

19. The method of claim 13, wherein said cells are primary cells isolated from tissue.

20. The method of claim 13, wherein said cells are pancreatic islet cells.

* * * * *

UNITED STATES PATENT AND TRADEMARK OFFICE
CERTIFICATE OF CORRECTION

PATENT NO.        : 9,068,162 B2                                    Page 1 of 1
APPLICATION NO.   : 12/704839
DATED             : June 30, 2015
INVENTOR(S)       : Van Dyke It is certified that error appears in the above-identified patent and that said Letters Patent is hereby corrected as shown below:

In the Claims:
Column 33, Claim 5, Line 14: Please correct "basic γ-keratose, acidic γ-keratose."
to read -- basic γ-keratose and acidic γ-keratose. --

Column 34, Claim 14, Lines 15-16:
Please correct "basic γ-kerateine, basic γ-kerateine"
to read -- basic γ-kerateine --

Signed and Sealed this
Twelfth Day of April, 2016

Michelle K. Lee
*Director of the United States Patent and Trademark Office*